United States Patent
Arrigo et al.

(10) Patent No.: US 9,278,936 B2
(45) Date of Patent: Mar. 8, 2016

(54) CRYSTALLINE FORMS OF 1-(3-TERT-BUTYL-1-P-TOLYL-1H-PYRAZOL-5-YL)-3-(5-FLUORO-2-(1-(2-HYDROXYETHYL)-1H-INDAZOL-5-YLOXY)BENZYL)UREA HYDROCHLORIDE

(71) Applicant: Array BioPharma Inc., Boulder, CO (US)

(72) Inventors: Alisha B. Arrigo, Boulder, CO (US); Donald T. Corson, Boulder, CO (US); Coralee G. Mannila, Boulder, CO (US)

(73) Assignee: ARRAY BIOPHARMA INC., Boulder, CO (US)

( * ) Notice: Subject to any disclaimer, the term of this patent is extended or adjusted under 35 U.S.C. 154(b) by 0 days.

(21) Appl. No.: 14/382,178

(22) PCT Filed: Feb. 27, 2013

(86) PCT No.: PCT/US2013/027979
§ 371 (c)(1),
(2) Date: Aug. 29, 2014

(87) PCT Pub. No.: WO2013/130573
PCT Pub. Date: Sep. 6, 2013

(65) Prior Publication Data
US 2015/0030673 A1    Jan. 29, 2015

Related U.S. Application Data

(60) Provisional application No. 61/605,572, filed on Mar. 1, 2012.

(51) Int. Cl.
*C07D 231/56* (2006.01)
*A61K 31/4155* (2006.01)

(52) U.S. Cl.
CPC .......... *C07D 231/56* (2013.01); *A61K 31/4155* (2013.01)

(58) Field of Classification Search
CPC .......................... C07D 231/56; A61K 31/4155
See application file for complete search history.

(56) References Cited

U.S. PATENT DOCUMENTS

2004/0052824 A1    3/2004    Abou Chacra-Vernet

FOREIGN PATENT DOCUMENTS

| CA | 2432362 A1 | 7/2002 |
|---|---|---|
| EP | 1170003 B1 | 4/2006 |
| WO | 2007089646 A1 | 8/2007 |

OTHER PUBLICATIONS

Opposition to Patent of Invention, filed Jan. 19, 2015 in Costa Rican patent application No. 2014-0408 (which corresponds to U.S. Appl. No. 14/382,178), provided as the original Spanish version (12 pages) together with English translation (9 pages).
Antonio Llinas and Jonathan M. Goodman, "Polymorph control: past, present and future", Drug Discovery Today, vol. 13, No. 5/6, Mar. 2008, 198-210.
Jie Lu and Sohrab Rohani, "Polymorphism and crystallization of active pharmaceutical ingredients (APIs)", Current Medicinal Chemistry, 2009, 16, 884-905.
Carlos Correa,"Guidelines for Examination of Pharmaceutical Patents" published by the WHO, ICTSD and UNCTAD, Mar. 2008, together with the English working version dated Jan. 2007 and Certificate of translation (total of 129 pages).
Ahn, J. S., et al., Bull. Korean Chem. Soc. 2011, vol. 32, No. 5, 1587-1592.
Cuine, J. F., et al., Pharmaceutical Research, vol. 24, No. 4, Apr. 2007, pp. 748-757.
Eastman Chemical Company, Oct. 2005, 24 pages, publication PCI-102B.
Fahr, A. and Liu, X., Expert Opinion Drug Delivery (2007) 4(4), pp. 403-416.
Fatouros, D. G., et al., Therapeutics and Clinical Risk Management 2007:3(4) 591-604.
Hancock, B. C. and M. Parks, Pharmaceutical Research, 2000, 17(4), pp. 397-404.
Kapetanovic, I. M., et al., Cancer Chemother. Pharmacol (2010) 65:1109-1116.
Kaukonen, A. M. et al., Pharmaceutical Research, vol. 21, No. 2, Feb. 2004, pp. 254-260.
Kohli, K., et al., Drug Discovery Today, vol. 15, Nos. 21/22, Nov. 2010, pp. 958-965.

(Continued)

*Primary Examiner* — Samantha Shterengarts
(74) *Attorney, Agent, or Firm* — Sarah S. Mastous; Viksnins Harris & Padys PLLP

(57) ABSTRACT

Provided herein is a hydrogen chloride salt of 1-(3-/t?r/-butyl-1-p-tolyl-1H-pyrazol-5-yl)-3-(5-fluoro-2-(1-(2-hydroxyethyl)-1H-indazol-5-yloxy)benzyl)urea, crystalline forms of 1-(3-½^butyl-1^-tolyl-1H-pyrazol-5-yl)-3-(5-fluoro-2-(1-(2-hydroxyethyl)-1H-indazol-5-yloxy)benzyl)urea hydrochloride, processes for the preparation of said crystalline forms, pharmaceutical compositions containing a crystalline form of 1-(3-r<i/-r-butyl-1-p-tolyl-1H-pyrazol-5-yl)-3-(5-fluoro-2-(1-(2-hydroxyethyl)-1H-indazol-5-yloxy)benzyl)urea hydrochloride Form B, processes for the preparation of said compositions, pharmaceutical compositions prepared by said methods, and the use of said compositions in the treatment of various diseases and disorders.

(I)

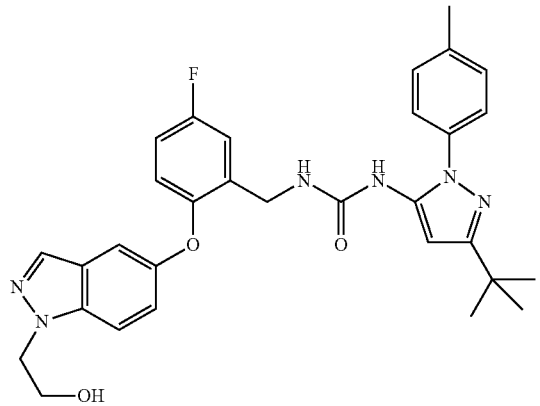

98 Claims, 7 Drawing Sheets

(56) References Cited

OTHER PUBLICATIONS

Komrokji, R. et al., "Phase 1 Dose-Escalation/Expansion Study of the p38/Tie2 Inhibitor ARRY-614 in Patients with IPSS Low/Int-1 Risk Myelodysplastic Syndromes", 2011 Annual Meeting of the American Society of Hematology, Abstract 118, Dec. 11, 2011.
Konno T., Chem. Pharm. Bull., 38(7), 2003-2007 (1990).
Nielsen, F. et al., Journal of Pharmaceutical Sciences, vol. 96, No. 4, Apr. 2007, pp. 876-892.
Patel, A. R. and Vavia, P.R., The AAPS Journal 2007; 9(3) Article 41, pp. E344-E352.
Patel, M. J., et al., Intl. J. Pharm. Sci. Review and Research, vol. 4, Issue 3, Sep.-Oct. 2010; Article 005, pp. 29-35.
Patent Cooperation Treaty, International Searching Authority, Search Report and Written Opinion for PCT/US2013/027979, 10 pages, May 22, 2013.
Pouton, C. W., Advanced Drug Delivery Reviews, 25 (1997) pp. 47-58.
Roop, G. N., et al., Int. J. Drug Dev. & Res., Sep.-Dec. 2009, vol. 1, Issue 1, pp. 10-18.
Shukla, J. B., et al., Pharma Science Monitor, vol. 1, Issue 2, 2010, pp. 13-33.
Strickley, R.G., Pharmaceutical Research, vol. 21, No. 2, Feb. 2004, pp. 201-230.
Talegaonkar, S., Recent Patents on Drug Delivery & Formulation 2008, vol. 2, pp. 238-257.
Tang, J.-L., et al., Current Drug Therapy, 2007, vol. 2, pp. 85-93.
van Hoogevest, P., et al., Expert Opinion Drug Delivery, 2011 8(11): 1481-1500.
Wilson, A. G. E., Future Med. Chem. (2010) 2(1), 1-5.
Koch, K., The Design and Early Development of the P38/Tie-2 inhibitor, ARRY-614 in Hematologic Cancers, American Association for Cancer Research Annual Meeting, Apr. 6, 2013 (40 pages).
Winski, S.L., et al., Role of p38 MAPK and Tie2 in the Pathogenesis of MDS and Their Inhibition by Dual Inhibitor ARRY-614, American Society of Hematology Annual Meeting, Dec. 9, 2012.
Garcia-Manero, et al., Clinical Evaluation of ARRY-614, a Dual p38/Tie2 Inhibitor for Patients with Myelodysplastic Syndromes, Identifies Unique Disease-Related and Drug-Related Biomarkers, European Hematology Association Annual Congress, Jun. 16, 2012.
Winski, S.L., et al., ARRY-614, a Dual p38/Tie2 Inhibitor for Myelodysplastic syndromes: Overview of the Phase 1 Experience, International congress on Targeted Anticancer Therapies, Mar. 9, 2012 (21 pages).
Garcia-Manero, G., et al., Phase 1 Dose-Escalation/Expansion Study of ARRY-614 in Patients with IPSS Low/Int-1 Risk Myelodysplastic Syndromes, American Society of Hematology Annual Meeting, Dec. 11, 2011 (17 pages).

CRYSTALLINE FORMS OF 1-(3-TERT-BUTYL-1-P-TOLYL-1H-PYRAZOL-5-YL)-3-(5-FLUORO-2-(1-(2-HYDROXYETHYL)-1H-INDAZOL-5-YLOXY)BENZYL)UREA HYDROCHLORIDE

RELATED APPLICATIONS

This application is a 371 filing of PCT Application No. PCT/US2013/027979, filed Feb. 27, 2013, which claims priority to U.S. Provisional Application No. 61/605,572 filed Mar. 1, 2012, each of which is incorporated herein by reference in its entirety.

BACKGROUND OF THE INVENTION

1. Field of the Invention

Provided herein is a hydrogen chloride salt of 1-(3-tert-butyl-1-p-tolyl-1H-pyrazol-5-yl)-3-(5-fluoro-2-(1-(2-hydroxyethyl)-1H-indazol-5-yloxy)benzyl)urea, crystalline forms of 1-(3-tert-butyl-1-p-tolyl-1H-pyrazol-5-yl)-3-(5-fluoro-2-(1-(2-hydroxyethyl)-1H-indazol-5-yloxy)benzyl) urea hydrochloride, processes for the preparation of said crystalline forms, pharmaceutical compositions containing crystalline forms of 1-(3-tert-butyl-1-p-tolyl-1H-pyrazol-5-yl)-3-(5-fluoro-2-(1-(2-hydroxyethyl)-1H-indazol-5-yloxy) benzyl)urea hydrochloride Form B, processes for the preparation of said compositions, pharmaceutical compositions prepared by said methods, and the use of said compositions in the treatment of various diseases and disorders.

2. Description of the State of the Art

The myelodysplastic syndromes (MDS, formerly known as pre-leukemia) are a diverse collection of hematological (blood-related) medical conditions that involve ineffective production (or dysplasia) of the myeloid class of blood cells. Patients with MDS often develop severe anemia and require frequent blood transfusions. In most cases, the disease worsens and the patient develops cytopenias (low blood counts) due to progressive bone marrow failure. In about one third of patients with MDS, the disease transforms into acute myelogenous leukemia (AML), usually within months to a few years. The myelodysplastic syndromes include all disorders of the stem cell in the bone marrow. In MDS, hematopoiesis (blood production) is disorderly and ineffective. The number and quality of blood-forming cells decline irreversibly, further impairing blood production The goals of therapy for patients with MDS are to control symptoms, improve quality of life, improve overall survival, and decrease progression to AML. Treatment options for patients with myelodysplastic syndromes range from supportive care that helps relieve symptoms to aggressive treatment that may slow or prevent progression of the disease. Problems caused by low blood cell counts, such as fatigue and infections, may be treated with transfusions of blood products or the use of growth factors. Chemotherapy may be used to delay progression of the disease. Other drug therapy may be used to lessen the need for transfusions. Certain patients may benefit from aggressive treatment with chemotherapy followed by stem cell transplant using stem cells from a donor. For patients with transfusion-dependent anemia due to low or intermediate-1 risk MDS associated with a deletion 5q cytogenetic abnormality, lenalidomide (Revlimid®) is an approved therapy in the United States. Other treatment options include immunosuppressive agents, low/intermediate intensity chemotherapy (e.g., azacitidine, decitabine, cytarabine), and finally high intensity antileukemic chemotherapy and hematopoietic cell transplantation. Accordingly, there remains a need for new pharmaceutical compositions and methods for treating MDS.

1-(3-Tert-butyl-1-p-tolyl-1H-pyrazol-5-yl)-3-(5-fluoro-2-(1-(2-hydroxyethyl)-1H-indazol-5-yloxy)benzyl)urea (also known as "ARRY-614") is exemplified in WO 2007/089646 and possesses the following structural formula:

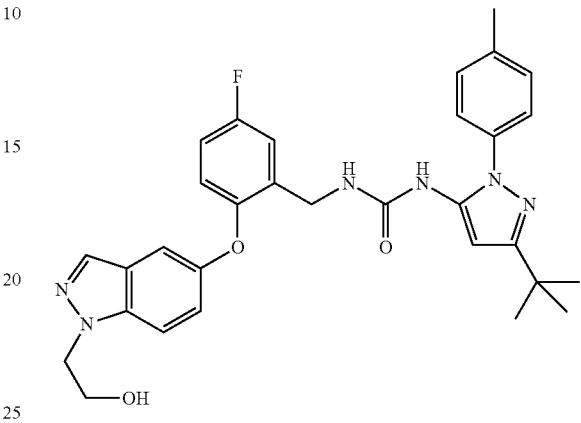

1-(3-Tert-butyl-1-p-tolyl-1H-pyrazol-5-yl)-3-(5-fluoro-2-(1-(2-hydroxyethyl)-1H-indazol-5-yloxy)benzyl)urea has been shown to possess potent inhibitory activity against the p38 MAPK and Tie2 protein kinases and therefore could be useful in the treatment of kinase-mediated conditions including proliferative disorders (such as myelodysplastic syndromes), inflammatory diseases, autoimmune diseases, destructive bone disorders, infectious diseases, viral disease, fibrotic disease and neurodegenerative diseases.

1-(3-Tert-butyl-1-p-tolyl-1H-pyrazol-5-yl)-3-(5-fluoro-2-(1-(2-hydroxyethyl)-1H-indazol-5-yloxy)benzyl)urea has been tested in a Phase 1 human clinical trial for myelodysplastic syndromes (MDS) (see R. Komrokji, et al., "Phase 1 Dose-Escalation/Expansion Study of the p38/Tie2 Inhibitor ARRY-614 in Patients with IPSS Low/Int-1 Risk Myelodysplastic Syndromes", 2011 Annual Meeting of the American Society of Hematology, Dec. 11, 2011; which can also be found at: http://www.arraybiopharma.com/_documents/Publication). In this study, a powder in capsule ("PIC") composition of amorphous ARRY-614 was prepared and administered to patients with myelodysplastic syndrome, and inter-patient variability in exposure profiles (concentration/time profiles) and exposure PK parameters (AUC and $C_{max}$) was high. In addition, the clinical study protocol required administration of 12×100 mg capsules per dose (i.e., once daily administration of 12×100 mg capsules), which arose from the inability to achieve a higher drug load per capsule of the amorphous form of the compound. This imposed an undesirably large pill burden on the patients. Due to the limitations of drug load per capsule, only a maximal administrable dose was reached but not a true maximum tolerated dose. A new formulation may provide greater dosing potential if needed.

In order to formulate a pharmaceutically active compound such as 1-(3-tert-butyl-1-p-tolyl-1H-pyrazol-5-yl)-3-(5-fluoro-2-(1-(2-hydroxyethyl)-1H-indazol-5-yloxy)benzyl) urea into a suitably acceptable dosage form, it is desirable that the active compound possess acceptable stability and handling properties in addition to possessing acceptable biopharmaceutical properties such as solubility and dissolution. 1-(3-Tert-butyl-1-p-tolyl-1H-pyrazol-5-yl)-3-(5-fluoro-2-(1-(2-hydroxyethyl)-1H-indazol-5-yloxy)benzyl)urea exists in an amorphous form. It is a BCS Class II molecule with low aqueous solubility (<10 μg/mL) across the typical physiological pH range of 2-8, with a ClogP 6.8 and a calculated $pK_a$ less than 3.

Bioavailability is one of the key parameters for many therapeutic indications and can be dependent on the form of the substance to be used in the pharmaceutical composition. Potential pharmaceutical solids of active drugs include crystalline solids and amorphous solids. It is known that the amorphous forms of many pharmaceutical substances exhibit different dissolution characteristics and bioavailability patterns compared to the crystalline forms (Konno T., Chem. Pharm. Bull., 1990, 38:2003-2007). There is often a decrease in solubility of 12-1600 fold in going from an amorphous form to crystalline form (B. C. Hancock and M. Parks, Pharmaceutical Research, 2000, 17(4) 397-404). The identification and selection of a solid form of a pharmaceutical compound is complex, given that a change in solid form may affect a variety of physical and chemical properties, which may provide benefits or drawbacks in processing, formulation, stability and bioavailability, among other important pharmaceutical characteristics. Drawbacks of using the amorphous form of a drug can include the potential of the amorphous solids to lack chemical and physical stability, as well as the risk of form conversion from amorphous to crystalline material at any time during manufacturing and/or storage. In addition, in some cases crystalline salts of the active drug do not form easily and/or are not stable, which is probably due to low $pK_a$ values. The $pK_a$ value expresses the strength of acids and base, i.e., the tendency for an acid to lose a proton or a base to add a proton (Bronsted J. N., Rec. Trav. Chim. (1923) 47:718).

There remains a need for a pharmaceutical composition suitable for treating proliferative diseases such as MDS.

There also remains a need for a pharmaceutical composition containing a form of 1-(3-tert-butyl-1-p-tolyl-1H-pyrazol-5-yl)-3-(5-fluoro-2-(1-(2-hydroxyethyl)-1H-indazol-5-yloxy)benzyl)urea having increased exposure and increased relative bioavailability.

There also remains a need for a pharmaceutical composition containing a form of 1-(3-tert-butyl-1-p-tolyl-1H-pyrazol-5-yl)-3-(5-fluoro-2-(1-(2-hydroxyethyl)-1H-indazol-5-yloxy)benzyl)urea having reduced inter-patient variability in pharmacokinetic profiles.

There also remains a need for a pharmaceutical composition containing a form of 1-(3-tert-butyl-1-p-tolyl-1H-pyrazol-5-yl)-3-(5-fluoro-2-(1-(2-hydroxyethyl)-1H-indazol-5-yloxy)benzyl)urea having substantially similar pharmacokinetic profiles when administered to a mammal in the fed versus the fasted state.

There also remains a need for a pharmaceutical composition containing a form of 1-(3-tert-butyl-1-p-tolyl-1H-pyrazol-5-yl)-3-(5-fluoro-2-(1-(2-hydroxyethyl)-1H-indazol-5-yloxy)benzyl)urea wherein smaller doses of the composition are required to obtain the same pharmacological effect.

There also remains a need for a pharmaceutical composition containing a form of 1-(3-tert-butyl-1-p-tolyl-1H-pyrazol-5-yl)-3-(5-fluoro-2-(1-(2-hydroxyethyl)-1H-indazol-5-yloxy)benzyl)urea having acceptable pharmacokinetic properties at higher doses.

There also remains a need for a pharmaceutical composition containing a form of 1-(3-tert-butyl-1-p-tolyl-1H-pyrazol-5-yl)-3-(5-fluoro-2-(1-(2-hydroxyethyl)-1H-indazol-5-yloxy)benzyl)urea having an increased rate of dissolution.

There also remains a need for a pharmaceutical composition containing a form of 1-(3-tert-butyl-1-p-tolyl-1H-pyrazol-5-yl)-3-(5-fluoro-2-(1-(2-hydroxyethyl)-1H-indazol-5-yloxy)benzyl)urea that is chemically and physically stable under the conditions in which it is processed, handled and stored.

SUMMARY OF THE INVENTION

Novel compositions comprising a novel physical form of 1-(3-tert-butyl-1-p-tolyl-1H-pyrazol-5-yl)-3-(5-fluoro-2-(1-(2-hydroxyethyl)-1H-indazol-5-yloxy)benzyl)urea, specifically crystalline polymorph 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B, which are suitable for treating proliferative disorders such as myelodysplastic syndromes have been discovered having the following unexpected properties:

Pharmaceutical compositions described herein comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B have increased exposure and increased relative bioavailability.

Pharmaceutical compositions described herein comprising a 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B provide reduced inter-patient variability in pharmacokinetic profiles.

Pharmaceutical compositions described herein comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B have substantially similar pharmacokinetic profiles when administered to a mammal in the fed versus the fasted state.

Pharmaceutical compositions described herein comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B provide for administration of smaller doses to obtain the same pharmacological effect.

Pharmaceutical composition described herein comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B have acceptable pharmacokinetic properties at higher doses.

Pharmaceutical composition comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B have an increased rate of dissolution.

Pharmaceutical composition comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B are chemically and physically stable under the conditions in which they are processed, handled and stored.

In particular, compositions comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B have been discovered which provide one or more of the above-described advantages when compared to a powder in capsule form of the amorphous free base of 1-(3-tert-butyl-1-p-tolyl-1H-pyrazol-5-yl)-3-(5-fluoro-2-(1-(2-hydroxyethyl)-1H-indazol-5-yloxy)benzyl)urea.

Also provided herein is a crystalline polymorph of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B.

Also provided herein are methods of preparing 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B.

Also provided herein is a pharmaceutical composition comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix, wherein said carrier matrix comprises at least one oil and at least one surfactant.

Also provided herein is a pharmaceutical composition comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix, wherein said carrier matrix comprises at least one oil, at least one surfactant, and at least one release modifier.

Also provided herein is a pharmaceutical composition comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in at least one surfactant.

Also provided herein is a pharmaceutical composition comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in at least one surfactant, wherein said composition further comprises at least one release modifier.

Also provided herein is a pharmaceutical composition comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in at least one oil.

Also provided herein is a pharmaceutical composition comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in at least one oil, wherein said composition further comprises at least one release modifier.

Also provided herein methods of treating proliferative disorders, such as myelodysplastic syndromes, comprising administering to a patient in need thereof a pharmaceutical composition described herein.

Also provided herein methods of treating inflammation, osteoarthritis, rheumatoid arthritis, autoimmune diseases, and other cytokine-mediated diseases comprising administering to a patient in need thereof a pharmaceutical composition described herein.

Also provided herein are pharmaceutical compositions for use in treating proliferative disorders, such as myelodysplastic syndromes, in a mammal.

Also provided herein are pharmaceutical compositions for use in treating inflammation, osteoarthritis, rheumatoid arthritis, autoimmune diseases, and other cytokine-mediated diseases.

Also provided herein is a use of a pharmaceutical composition described herein in the manufacture of a medicament for the treatment of proliferative disorders, such as myelodysplastic syndromes, in a mammal.

Also provided herein is a use of a pharmaceutical composition described herein in the manufacture of a medicament for the treatment of inflammation, osteoarthritis, rheumatoid arthritis, autoimmune diseases, and other cytokine-mediated diseases.

Also provided herein are processes for preparing pharmaceutical compositions described herein.

Also provided herein are pharmaceutical compositions prepared by the methods described herein.

Also provided herein is a crystalline polymorph of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form A.

Also provided herein are methods for preparing 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form A.

BRIEF DESCRIPTION OF THE FIGURES

The accompanying drawings, which are incorporated herein and form a part of the specification, illustrate non-limiting embodiments of this invention, and together with the description, serve to explain the principles of the invention.

DETAILED DESCRIPTION OF THE INVENTION

Definitions

Figure 1:
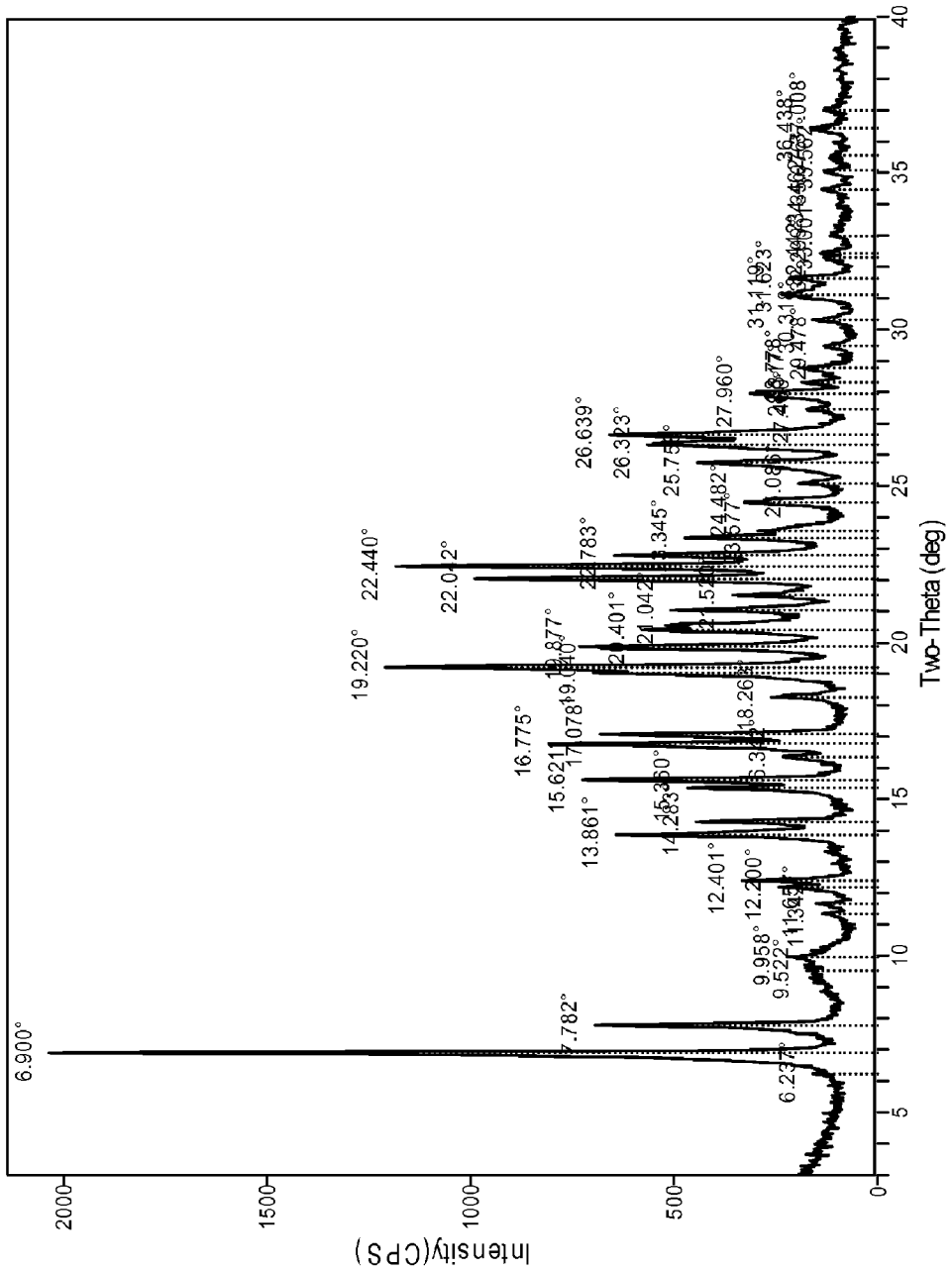
FIG. 1 shows an X-ray powder diffraction pattern for unmicronized crystalline polymorph 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form A.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable that is inherently discrete, the variable can be equal to any integer value of the numerical range, including the end-points of the range. Similarly, for a variable that is inherently continuous, the variable can be equal to any real value of the numerical range, including the end-points of the range. As an example, a variable that is described as having values between 0 and 2, can be 0, 1 or 2 for variables that are inherently discrete, and can be 0.0, 0.1, 0.01, 0.001, or any other real value for variables that are inherently continuous.

The term "about" preceding one or more peak positions in an X-ray powder diffraction pattern means that all of the peaks of the group which it precedes are reported in terms of angular positions (two theta) with an allowable variability of ±0.3°. The variability of ±0.3° is intended to be used when comparing two powder X-ray diffraction patterns. In practice, if a diffraction pattern peak from one pattern is assigned a range of angular positions (two theta) which is the measured peak position±0.3° and if those ranges of peak positions overlap, then the two peaks are considered to have the same angular position. For example, if a peak from one pattern is determined to have a position of 11.0°, for comparison purposes the allowable variability allows the peak to be assigned a position in the range of 10.7°-11.3°.

The term "amorphous" means a solid in a solid state that is a non-crystalline state. Amorphous solids are disordered arrangements of molecules and therefore possess no distinguishable crystal lattice or unit cell and consequently have no definable long range ordering. The solid state form of a solid may be determined by polarized light microscopy, X-ray powder diffraction ("XRPD"), differential scanning calorimetry ("DSC"), or other standard techniques known to those of skill in the art.

The term "AUC" refers to the area under the plasma concentration-time curve.

The term "$AUC_{inf}$" refers to the area under the concentration time curve from time 0 extrapolated to infinity.

The term "$AUC_{last}$" refers to the area under the plasma concentration-time curve from time 0 to the time of the last quantifiable concentration.

The term "bioavailability" refers to a measurement of the rate and extent to which an active ingredient is absorbed from a drug product and becomes available at the site of action. From a pharmacokinetic perspective, bioavailability data for a given formulation provides an estimate of the relative fraction of the orally administered dose that is absorbed into the systemic circulation when compared to the bioavailability data for an intravenous dosage form.

The term "$C_{max}$" refers to the maximum observed plasma concentration.

The term "Form A" when used alone is meant to be interchangeable with 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form A.

The term "Form B" when used alone is meant to be interchangeable with 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B.

The term "dose" or "dosage" as used herein refers to a specified quantity of a pharmaceutical agent provided in a single administration. In certain embodiments, a dose may be administered as a single capsule, a single tablet or a single liquid volume. In certain embodiments, a dose may be administered, for example, in two or more capsules, tablets or liquid volumes. For example, in certain embodiments where oral administration is desired, the desired dose requires an amount of a compound that is not easily accommodated by a single capsule. In such embodiments, two or more capsules may be used to achieve the desired dose.

The term "mammal" means a warm-blooded animal that has or is at risk of developing a disease described herein and includes, but is not limited to, guinea pigs, dogs, cats, rats, mice, hamsters, and primates, including humans.

The term "micronizing" is used to describe methods of particle size reduction where the resulting particles have a Dv90 less than 10 μM. Dv is a measurement used in the art to define distribution of particle sizes (i.e., volume distribution). For example, a Dv50 is the size in microns that splits the distribution with half above and half below a particular diameter of a sphere, i.e., the Dv50 is the median for a volume distribution. A Dv90 of 10 μM means that 90% of the particles have a particle size less than 10 μM. Monitoring of particle size reduction can be performed using methods known to persons skilled in the art, for example using laser diffraction.

The term "micronized" refers to particles having a Dv90 less than or equal to 10 μM.

The phrase "pharmaceutically acceptable" is used herein to refer to those compounds, materials, compositions, and/or dosage forms which are, within the scope of sound medical judgment, suitable for use in contact with the tissues of a mammal such as a human (e.g., does not produce an adverse, allergic or other unwanted reaction when administered to a mammal).

The terms "polymorph" and "polymorphic form" refer to different crystalline forms of a single compound. That is, polymorphs are distinct solids sharing the same molecular formula, yet each polymorph may have distinct solid state physical properties. Therefore, a single compound may give rise to a variety of polymorphic forms where each form has different and distinct solid state physical properties, such as different solubility profiles, dissolution rates, melting point temperatures, flowability, and/or different X-ray diffraction peaks. The differences in physical properties may affect pharmaceutical parameters such as storage stability, compressibility and density (which can be important in formulation and product manufacturing), and dissolution rate (which can be an important factor in bioavailability). Techniques for characterizing polymorphic forms include, but are not limited to, X-ray powder diffractometry (XRPD), differential scanning calorimetry (DSC), thermal gravimetric analysis (TGA), single-crystal X-ray diffractometry (XRD), vibrational spectroscopy, e.g., infrared (IR) and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility measurements, dissolution measurements, elemental analysis and Karl Fischer analysis.

As used herein, the term "release modifier" refers to an excipient that slows or delays the rate of release of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B from the pharmaceutical composition or carrier matrix relative to the rate of release of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B from a pharmaceutical composition or carrier matrix that does not comprise said excipient.

As used herein, the term "solvate" refers to a crystalline form of a substance which contains solvent. The term "hydrate" refers to a solvate wherein the solvent comprises water.

The phrase "substantially pure" means the polymorphic form includes less than about 15% by weight of impurities, including other polymorphic and amorphous forms. In certain embodiments, the substantially pure polymorphic form includes less than about 10% by weight of impurities, including other polymorphic and amorphous forms. In certain embodiments, the substantially pure polymorphic form includes less than about 5% by weight of impurities, including other polymorphic and amorphous forms. In certain embodiments, the substantially pure polymorphic form includes less than about 1% by weight of impurities, including other polymorphic and amorphous forms.

The phrase "substantially in the form of" when referring to a particular polymorphic form means the polymorphic form includes less than about 15% by weight of other forms, including other polymorphic forms and amorphous forms. In certain embodiments, the substantially pure polymorphic form includes less than about 10% by weight of other forms, including other polymorphic forms and amorphous forms. In certain embodiments, the substantially pure polymorphic form includes less than about 5% by weight of other forms, including other polymorphic forms and amorphous forms. In certain embodiments, the substantially pure polymorphic form includes less than about 1% by weight of other forms, including other polymorphic forms and amorphous forms.

The term "suspension" as used herein refers to a heterogeneous or homogenous mixture of solid particles in a fluid or carrier matrix in which the particles are dispersed but not dissolved in the fluid or carrier matrix, and wherein the solid particles are likely to settle out of the fluid or carrier matrix at some point in time if the mixture is left undisturbed. For suspensions containing micronized particles, the rate of settling is typically delayed relative to unmicronized particles. For example, for pharmaceutical compositions described herein comprising micronized 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B, settling can be delayed for at least 1 day for liquid suspensions and at least one year for suspensions in the semi-solid or solid form. The carrier matrix may be a liquid, semi-solid or solid, depending on the temperature and the composition of the carrier.

The phrases "therapeutically effective amount" or "effective amount" mean an amount of a compound or composition described herein that, when administered to a mammal in need of such treatment, is sufficient to (i) treat the particular disease, condition, or disorder, (ii) attenuate, ameliorate, or eliminate one or more symptoms of the particular disease, condition, or disorder, or (iii) delay the onset of one or more symptoms of the particular disease, condition, or disorder described herein. The amount of a compound that will correspond to such an amount will vary depending upon factors such as the particular compound or composition, disease condition and its severity, and the identity (e.g., weight) of the mammal in need of treatment, but can nevertheless be routinely determined by one skilled in the art.

The terms "treat" or "treatment" refer to therapeutic or palliative measures. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

The term "$T_{max}$" refers to the time to maximum observed plasma concentration.

Hydrochloride Salts

Provided herein is a hydrogen chloride salt of 1-(3-tert-butyl-1-p-tolyl-1H-pyrazol-5-yl)-3-(5-fluoro-2-(1-(2-hydroxyethyl)-1H-indazol-5-yloxy)benzyl)urea. The salt may be in various forms, all of which are included within the scope of the invention. These forms include anhydrous forms as well as solvates. A further form may be produced by desolvating solvates. In a particular embodiment, the salt is an anhydrous hydrogen chloride salt of 1-(3-tert-butyl-1-p-tolyl-1H-pyrazol-5-yl)-3-(5-fluoro-2-(1-(2-hydroxyethyl)-1H-indazol-5-yloxy)benzyl)urea.

In certain embodiments, 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride is crystalline. Crystalline salts typically have improved handling properties from a manufacturing point of view compared to the amorphous free base form. The preparation of a crystalline form of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride also provide a means of purification, as process impurities can be purged during isolation of the salt.

In one embodiment, provided herein are polymorphic forms of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride, which are designated as polymorph Forms A and B. In one embodiment, the polymorphs described herein exist as anhydrous forms. In another embodiment, the polymorphs described herein are solvates, including hydrates.

Form A

In one embodiment, provided herein is crystalline polymorph of 1-(3-tert-butyl-1-p-tolyl-1H-pyrazol-5-yl)-3-(5-fluoro-2-(1-(2-hydroxyethyl)-1H-indazol-5H-indazol-5-yloxy)benzyl)urea hydrochloride Form A. In one embodiment, said crystalline polymorph Form A is in an anhydrous form. In one embodiment, said Form A is a solvate. Form A can be distinguished by the X-ray Powder Diffraction (XRPD) pattern in FIG. 1 and/or peak assignments of the XRPD pattern of FIG. 1 as provided in Table 1 (Example 1-C).

In certain embodiments, 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form A has an XRPD pattern with at least one characteristic peak (2θ degrees±0.3) at about 6.9.

In certain embodiments, 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form A has an XRPD pattern with at least five characteristic peaks (2θ degrees±0.3) at about 6.9, 7.8, 13.9, 15.6 and 19.2.

In certain embodiments, 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form A has an XRPD pattern with at least ten characteristic peaks (2θ degrees±0.3) at about 6.9, 7.8, 13.9, 15.6, 16.7, 17.1, 19.2, 22.4, 22.8 and 26.6.

In certain embodiments, 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form A has an XRPD pattern that is substantially the same XRPD pattern as shown in FIG. 1.

In certain embodiments, 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form A has an XRPD pattern that substantially includes the peaks in Table 1.

It will be understood that the 2-theta values of the X-ray powder diffraction patterns for 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form A may vary slightly from one instrument to another and also depending on variations in sample preparation and batch to batch variation, and so the values quoted are not to be construed as absolute. It will also be understood that the relative intensities of peaks may vary depending on orientation effects so that the intensities shown in the XRPD trace included herein are illustrative and not intended to be used for absolute comparison. Accordingly, it is to be understood that the phrase "substantially the same XRPD pattern as shown in FIG. 1" means that for comparison purposes, at least 90% of the peaks shown in FIG. 1 are present. It is to be understood that the relative peak positions may vary ±0.3 degrees from the peak positions shown in FIG. 1. It is to be further understood that for comparison purposes some variability in peak intensities from those shown in FIG. 1 is allowed.

In a like manner, the phrase "substantially includes the peaks of Table 1" is understood to mean that those X-ray powder diffraction patterns having diffraction peaks with 2 theta values within plus or minus ±0.3 degrees of Table 1 are within the scope of the diffraction pattern referenced in Table 1.

Figure 2:
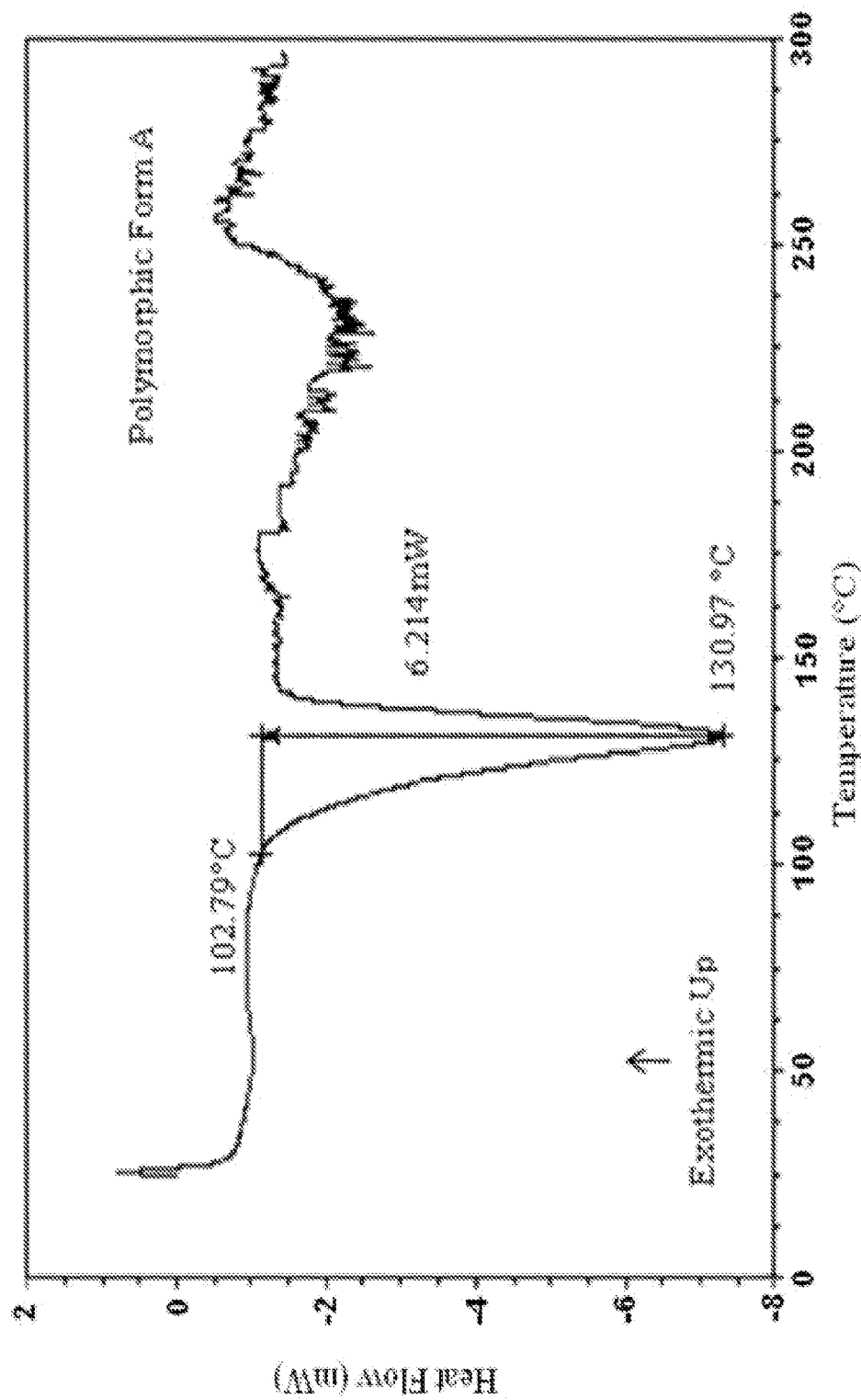
FIG. 2 shows a DSC thermogram of unmicronized crystalline polymorph 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form A.

1-(3-Tert-butyl-1-p-tolyl-1H-pyrazol-5-yl)-3-(5-fluoro-2-(1-(2-hydroxyethyl)-1H-indazol-5-yloxy)benzyl)urea hydrochloride Form A can also be distinguished by the representative DSC thermogram substantially as shown in FIG. 2, having a melt maxima temperature of about 131±5° C. As used herein, "substantially as shown in FIG. 2" means that the temperatures of the endothermic event shown in FIG. 2 can vary by about ±5° C.

In one embodiment, provided herein is a process for preparing 1-(3-tert-butyl-1-p-tolyl-1H-pyrazol-5-yl)-3-(5-fluoro-2-(1-(2-hydroxyethyl)-1H-indazol-5-yloxy)benzyl) urea hydrochloride Form A, comprising:

(a) combining a solution of amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea in THF with at least 1.5 equivalents of hydrochloric acid in 1,4-dioxane for a sufficient time to convert 1-(3-tert-butyl-1-p-tolyl-1H-pyrazol-5-yl)-3-(5-fluoro-2-(1-(2-hydroxyethyl)-1H-indazol-5-yloxy)benzyl)urea to 1-(3-tert-butyl-1-p-tolyl-1H-pyrazol-5-yl)-3-(5-fluoro-2-(1-(2-hydroxyethyl)-1H-indazol-5-yloxy) benzyl)urea hydrochloride Form A;

(b) allowing said Form A to crystallize from said solution; and (c) isolating said Form A.

Form B

In one embodiment, provided herein is crystalline polymorph 1-(3-tert-butyl-1-p-tolyl-1H-pyrazol-5-yl)-3-(5-fluoro-2-(1-(2-hydroxyethyl)-1H-indazol-5-yloxy)benzyl) urea hydrochloride Form B. In one embodiment, said Form B is in an anhydrous form. In one embodiment, said Form B is a solvate. 1-(3-Tert-butyl-1-p-tolyl-1H-pyrazol-5-yl)-3-(5-fluoro-2-(1-(2-hydroxyethyl)-1H-indazol-5-yloxy)benzyl) urea hydrochloride Form B can be distinguished by the XRPD pattern in FIG. 3 and/or peak assignments of the XRPD pattern of FIG. 3 as provided in Table 2 (Example 2-F).

In certain embodiments, 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B has an XRPD pattern with at least one characteristic peak (2θ degrees±0.3) at about 15.9.

In certain embodiments, 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B has an XRPD pattern with at least five characteristic peaks (2θ degrees±0.3) at about 12.3, 13.0, 15.9, 16.9 and 17.6.

In certain embodiments, 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B has an XRPD pattern with at least ten characteristic peaks (2θ degrees±0.3) at about 10.0, 12.3, 13.0, 15.9, 16.9, 17.6, 18.5, 23.4, 27.0 and 27.3.

In certain embodiments, 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B has an XRPD pattern with at least fifteen characteristic peaks (2θ degrees±0.3) at about 10.0, 12.3, 13.0, 15.9, 16.9, 17.6, 18.5, 20.4, 21.5, 21.9, 22.4, 23.4, 25.9, 27.0 and 27.3.

In certain embodiments, 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B has an XRPD pattern with at least twenty characteristic peaks (2θ degrees±0.3) at about 10.0, 12.3, 13.0, 15.9, 16.9, 17.6, 18.5, 19.8, 20.4, 20.8, 21.5, 21.9, 22.4, 23.4, 23.9, 24.6, 25.2, 25.9, 27.0 and 27.3.

Figure 3:
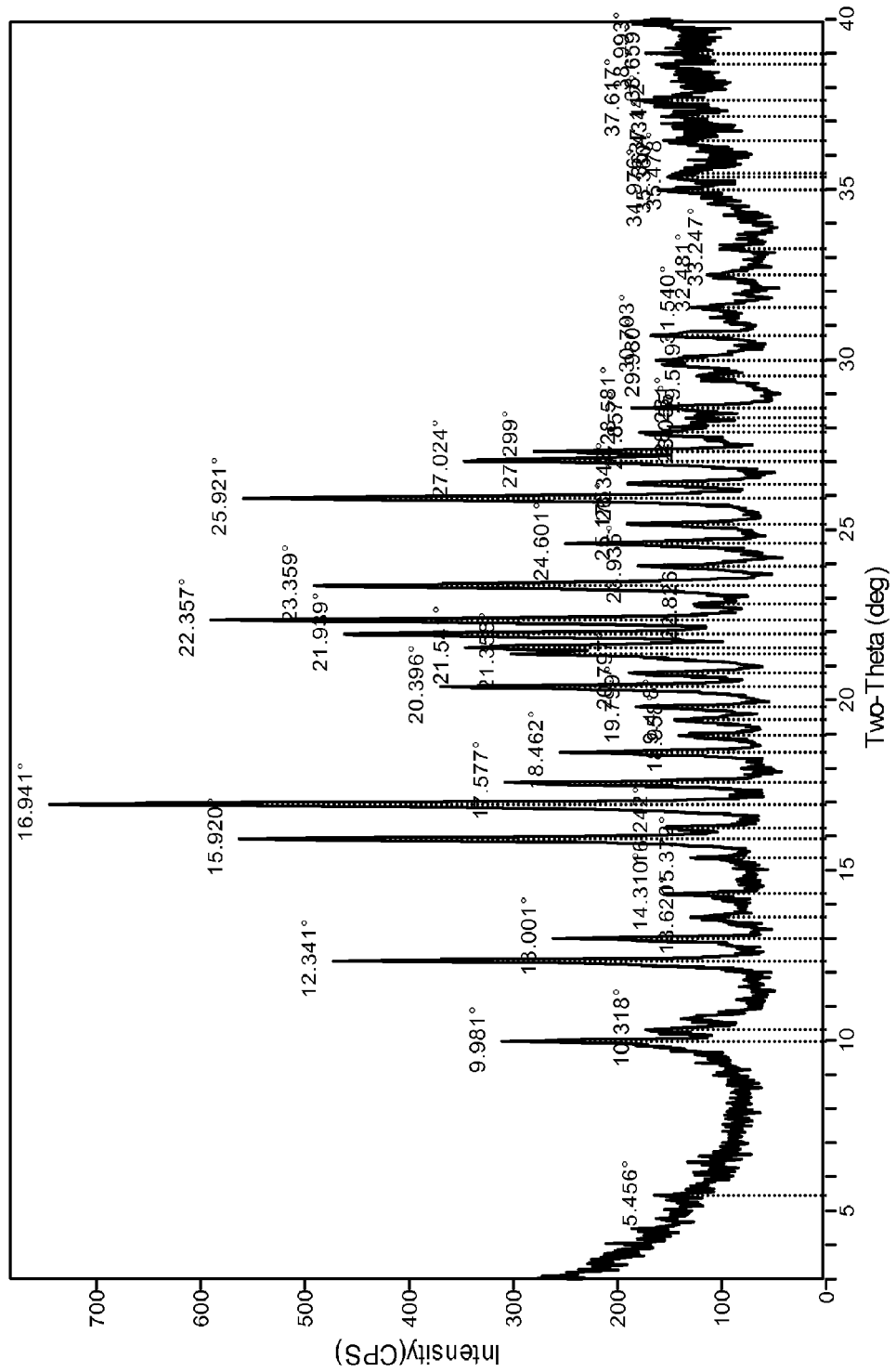
FIG. 3 shows an X-ray powder diffraction pattern for unmicronized crystalline polymorph 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B.

In certain embodiments, 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B has an XRPD pattern that is substantially the same XRPD pattern as shown in FIG. 3.

In certain embodiments, 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B has an XRPD pattern that substantially includes the peaks in Table 2.

It will be understood that the degree 2-theta values of the X-ray powder diffraction patterns for Form B may vary slightly from one instrument to another and also depending on variations in sample preparation and batch to batch variation, and so the values quoted are not to be construed as absolute. It will also be understood that the relative intensities of peaks may vary depending on orientation effects so that the intensities shown in the XRPD trace included herein are illustrative and not intended to be used for absolute comparison. Accordingly, it is to be understood that the phrase "substantially the same XRPD pattern as shown in FIG. 3" means that for comparison purposes, at least 90% of the peaks shown in FIG. 3 are present. It is to be understood that the relative peak positions may vary ±0.3 degrees from the peak positions shown in FIG. 3. It is to be further understood that for comparison purposes some variability in peak intensities from those shown in FIG. 3 is allowed.

In a like manner, the phrase "substantially includes the peaks of Table 2" is understood to mean that those X-ray powder diffraction patterns having diffraction peaks with 2 theta values within plus or minus ±0.3 degrees of Table 2 are within the scope of the diffraction pattern referenced in Table 2.

Figure 4:
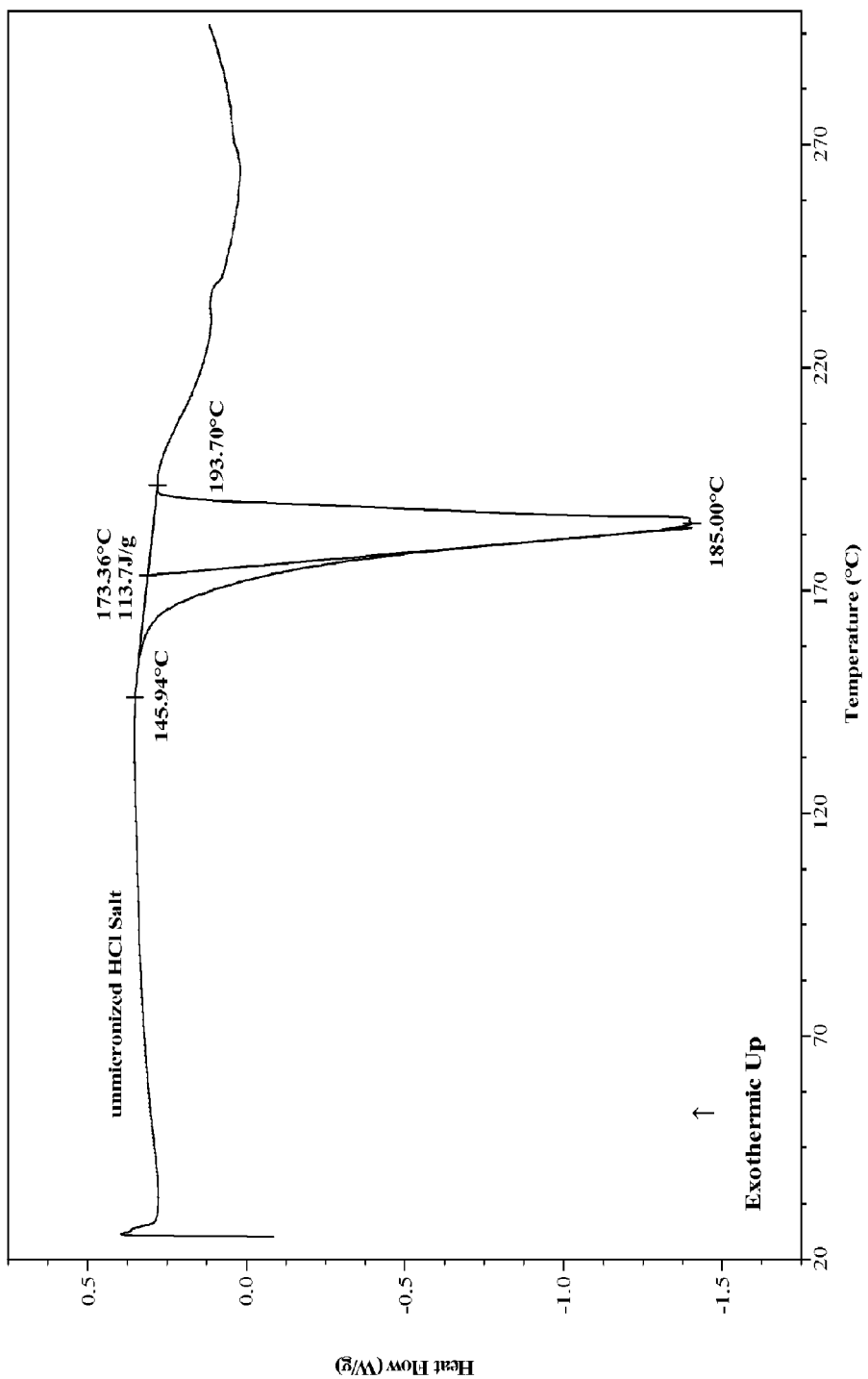
FIG. 4 shows a DSC thermogram for unmicronized crystalline polymorph 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B.

1-(3-Tert-butyl-1-p-tolyl-1H-pyrazol-5-yl)-3-(5-fluoro-2-(1-(2-hydroxyethyl)-1H-indazol-5-yloxy)benzyl)urea hydrochloride Form B can also be distinguished by the representative DSC thermogram presented in FIG. 4, which comprises an endothermic event having a melt maxima temperature at about 185±5° C.

In one embodiment, 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B has a DSC thermogram substantially as shown in FIG. 4. As used herein, "substantially as shown in FIG. 4" means that the temperatures of the endothermic event shown in FIG. 4 can vary by about +5° C.

In one embodiment, provided herein is a Process 1 for preparing 1-(3-tert-butyl-1-p-tolyl-1H-pyrazol-5-yl)-3-(5-fluoro-2-(1-(2-hydroxyethyl)-1H-indazol-5-yloxy)benzyl) urea hydrochloride Form B, comprising:

(a) combining a solution of amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea in MTBE with at least 1.5 equivalents of hydrochloric acid in 1,4-dioxane for a sufficient time to convert 1-(3-tert-butyl-1-p-tolyl-1H-pyrazol-5-yl)-3-(5-fluoro-2-(1-(2-hydroxyethyl)-1H-indazol-5-yloxy)benzyl)urea to 1-(3-tert-butyl-1-p-tolyl-1H-pyrazol-5-yl)-3-(5-fluoro-2-(1-(2-hydroxyethyl)-1H-indazol-5-yloxy) benzyl)urea hydrochloride Form B;

(b) allowing said Form B to crystallize from said solution; and (c) isolating said Form B.

In one embodiment, provided herein is a Process 2 for preparing 1-(3-tert-butyl-1-p-tolyl-1H-pyrazol-5-yl)-3-(5-fluoro-2-(1-(2-hydroxyethyl)-1H-indazol-5-yloxy)benzyl) urea hydrochloride Form B, comprising:

(a) combining a solution of amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea in a solvent selected from ethyl acetate, isopropyl acetate, acetonitrile, acetone, isopropyl alcohol and ethanol, with at least a stoichiometric amount of (i) HCl in 1,4-dioxane, (ii) HCl in acetone, or (iii) concentrated HCl, for a sufficient time to convert 1-(3-tert-butyl-1-p-tolyl-1H-pyrazol-5-yl)-3-(5-fluoro-2-(1-(2-hydroxyethyl)-1H-indazol-5-yloxy)benzyl)urea to 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B;

(b) allowing said Form B to crystallize from said solution; and (c) isolating said Form B.

In one embodiment of Process 2, about 1.05 equivalents of HCl are added.

In one embodiment, provided herein is a Process 3 for preparing 1-(3-tert-butyl-1-p-tolyl-1H-pyrazol-5-yl)-3-(5-fluoro-2-(1-(2-hydroxyethyl)-1H-indazol-5-yloxy)benzyl) urea hydrochloride Form B, comprising:

(a) combining a solution of amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea in isopropanol with at least a stoichiometric amount of an aqueous solution of hydrochloric acid for a sufficient time to convert 1-(3-tert-butyl-1-p-tolyl-1H-pyrazol-5-yl)-3-(5-fluoro-2-(1-(2-hydroxyethyl)-1H-indazol-5-yloxy)benzyl)urea to 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B;

(b) seeding said solution from step (a) with a suspension of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B in isopropanol to allow said 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B to crystallize from said solution; and (c) isolating said Form B.

In one embodiment of Process 3, about 1.05 equivalents of HCl are added.

Processes 1, 2 and 3 for preparing Form B are typically performed at ambient temperature.

In one embodiment, provided herein is a Process 4 for preparing 1-(3-tert-butyl-1-p-tolyl-1H-pyrazol-5-yl)-3-(5-fluoro-2-(1-(2-hydroxyethyl)-1H-indazol-5-yloxy)benzyl) urea hydrochloride Form B according to claim 1, comprising:

(a) heating a mixture of 2-(5-(2-(aminomethyl)-4-fluorophenoxy)-1H-indazol-1-yl)ethanol and phenyl 3-tert-butyl-1-p-tolyl-1H-pyrazol-5-ylcarbamate in an organic solvent at 35-40° C. for 5 hours to form 1-(3-tert-butyl-1-p-tolyl-1H-pyrazol-5-yl)-3-(5-fluoro-2-(1-(2-hydroxyethyl)-1H-indazol-5-yloxy)benzyl)urea;

(b) cooling said mixture to ambient temperature;

(c) filtering said mixture;

(d) adding at least a stoichiometric amount of aqueous HCl to said mixture;

(e) allowing said Form B to crystallize from said solution; and (f) isolating said Form B.

Examples of suitable organic solvents for Step (a) of Process 4 include (i) polar aprotic solvents (for example, acetonitrile, acetone, methyl ethyl ketone, THF, 2-methyltetrahydrofuran, and ethyl acetate), (ii) protic solvents (for example, alcohols such as methanol, ethanol, and isopropanol), and (iii) nonpolar solvents such as toluene. In one embodiment, the solvent used in step (a) is isopropanol.

In one embodiment, Process 4 further comprises: (d1) seeding said mixture in step (d) with 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B either as a solid or as a suspension in the organic solvent used in Step (a). In one embodiment, Step (d1) comprises seeding the mixture of Step (d) with 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B as a solid. In another embodiment, Step (d1) comprises seeding the mixture of Step (d) with 1-(3-tert-butyl-1-p-tolyl-1H-pyrazol-5-yl)-3-(5-fluoro-2-(1-(2-hydroxyethyl)-1H-indazol-5-yloxy) benzyl)urea hydrochloride Form B suspended in the same type of organic solvent that was used in Step (a).

In one embodiment, 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B is micronized. Methods of micronizing particles (i.e., methods of reducing the size of the particles to a Dv90 of 10 µM) are well known in the art and include, but are not limited to, jet-milling, pin-milling and ball-milling. In one embodiment, the polymorph is micronized in a jet mill.

Crystalline polymorph 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B provides advantages over the amorphous free base form. For example, process impurities can be purged during the crystallization procedure. In addition, formation of Form B is generally reproducible. In addition, Form B is suitable for formation of the novel compositions described herein.

Pharmaceutical Compositions

Also provided herein are pharmaceutical compositions comprising 1-(3-tert-butyl-1-p-tolyl-1H-pyrazol-5-yl)-3-(5-fluoro-2-(1-(2-hydroxyethyl)-1H-indazol-5-yloxy)benzyl) urea hydrochloride Form B.

In one embodiment, provided herein is pharmaceutical composition comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix, wherein said carrier matrix comprises at least one surfactant.

The surfactant can be any pharmaceutically acceptable surfactant. Suitable surfactants include non-ionic surfactants, anionic surfactants, cationic surfactants, and phospholipids.

In one embodiment, the surfactant is a non-ionic surfactant.

In one embodiment, the non-ionic surfactant is selected from Vitamin E TPGS (d-α-tocopheryl polyethylene glycol 1000 succinate), Solutol® HS 15 (polyethylene glycol-15-hydroxystearate), Cremophor® ELP (polyoxyl 35 castor oil), Cremophor® RH40 (polyoxyl 40 hydrogenated castor oil), Tween® 60 (polyethylene glycol sorbitan monostearate), Tween® 80 (polyoxyethylene 20 sorbitan monooleate), Labrasol® (caprylocaproyl polyoxylglycerides), Gelucire® 44/14 (lauroyl polyoxylglycerides), Gelucire® 50/13 (stearoyl polyoxylglycerides), Brij® C10 (polyethylene glycol hexadecyl ether), Brij® 98 (polyoxyethylene (20) oleyl ether), Brij® 58 (Polyethylene glycol hexadecyl ether), SPAN™ 20 (sorbitan monolaurate), SPAN™ 40 (sorbitan monopalmitate), SPAN™ 80 (sorbitan monooleate), Lutrol® F 68 (a synthetic copolymer of ethylene and propylene oxides), Lutrol® F 127 (a synthetic copolymer of ethylene and propylene oxides), phospholipids, zwitterionic surfactants such as lecithins, soy lecithin (phosphatidyl choline), phosphatidyl choline, phosphatidyl inositol, phosphatidyl ethanolamine, and cocamidopropyl betaine (CAPB), and mixtures thereof.

In one embodiment, the non-ionic surfactant is selected from Vitamin E TPGS, Solutol® HS 15, Cremophor® RH40, Labrasol® and Gelucire® 44/14.

In one embodiment, the non-ionic surfactant is Vitamin E TPGS.

In one embodiment, the surfactant is an anionic surfactant.

In one embodiment, the anionic surfactant is sodium dodecyl sulfate (also known as sodium lauryl sulfate) or phosphatidic acid.

In one embodiment, the surfactant is a cationic surfactant.

In one embodiment, provided herein is a pharmaceutical composition comprising about 1 to about 50% w/w of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix, wherein said carrier matrix comprises at least one surfactant, wherein the weight percent of said Form B is based on the total weight of the composition.

In another embodiment, provided herein is pharmaceutical composition comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix, wherein said carrier matrix comprises at least one oil.

The oil can be any pharmaceutically acceptable oil.

Examples of oils include long chain and medium chain triglycerides (with different degrees of saturation), synthetic oils, fatty acid esters of propylene glycols, ethers of ethylene glycols, glyceryl oils, cholesteryl oils, vegetable oils, nut oils, essential oils, mineral oil, glycerol monolinoleate (e.g., Maisine™ 35-1), glycerol monooleates (e.g., Piceol™), lipid-soluble compounds such as tocopherols, Vitamin E, Vitamin E succinate, and other lipophilic Vitamin E derivatives, and mixtures thereof.

In one embodiment, the oil is a long chain or medium chain triglyceride.

In one embodiment, the oil is a long chain triglyceride. A "long chain triglyceride" is defined herein as a $>C_{12}$ triglyceride. In one embodiment, the long chain triglyceride is a $C_{13}$-$C_{22}$ triglyceride.

In one embodiment, the long chain triglyceride is selected from Compritol® 888 ATO (glyceryl behenate), peanut oil, cottonseed oil, safflower oil, corn oil, sesame oil, castor oil, olive oil, peppermint oil, soybean oil, hydrogenated soybean oil and hydrogenated vegetable oils.

In one embodiment, the long chain triglyceride is Compritol® 888 ATO.

In one embodiment, the oil is a medium chain triglyceride. A "medium chain triglyceride" is defined herein as a ($C_6$-$C_{12}$) triglyceride. In one embodiment, the medium chain triglyceride is selected from caprylic acid/capric acid triglycerides and medium chain fatty acids.

In one embodiment, the medium chain triglyceride is a caprylic/capric triglyceride selected from Miglyol® 810, Miglyol® 812, Labrafac® Lipohile WL 1349, coconut oil and palm seed oil.

In one embodiment, the medium chain triglyceride is Labrafac® Lipophile WL 1349.

In one embodiment, provided herein is a pharmaceutical composition comprising about 1 to about 50% w/w of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix wherein said carrier matrix comprises at least one oil, wherein the weight percent of said Form B is based on the total weight of the composition. In one embodiment, the oil is Labrafac® Lipophile WL 1349. In one embodiment, the oil is Compritol® 888 ATO.

Further provided herein is a pharmaceutical composition comprising 1-(3-tert-butyl-1-p-tolyl-1H-pyrazol-5-yl)-3-(5-fluoro-2-(1-(2-hydroxyethyl)-1H-indazol-5-yloxy)benzyl) urea hydrochloride Form B suspended in a carrier matrix, wherein said carrier matrix comprises a mixture of at least one surfactant and at least one oil. Suitable surfactants and oils include those described above.

In one embodiment provided herein is a pharmaceutical composition comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix, wherein said carrier matrix comprises mixture of a surfactant and an oil, wherein the ratio of the oil to the surfactant is about 0.5:99.5.

In one embodiment, the carrier matrix comprises an oil and a surfactant in a ratio of about 5:95.

In one embodiment, the carrier matrix comprises an oil and a surfactant in a ratio of about 10:90.

In one embodiment, the carrier matrix comprises an oil and a surfactant in a ratio of about 15:85.

In one embodiment, the carrier matrix comprises an oil and a surfactant in a ratio of about 20:80.

In one embodiment, the carrier matrix comprises an oil and a surfactant in a ratio of about 25:75.

In one embodiment, the carrier matrix comprises an oil and a surfactant in a ratio of about 30:70.

In one embodiment, the carrier matrix comprises an oil and a surfactant in a ratio of about 33:67.

In one embodiment, the carrier matrix comprises an oil and a surfactant in a ratio of about 50:50.

In one embodiment, the carrier matrix comprises an oil and a surfactant in a ratio of about 75:25.

In one embodiment, the carrier matrix comprises an oil and a surfactant in a ratio of about 99:1.

In one embodiment provided herein is a pharmaceutical composition comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix, wherein the carrier matrix comprises an oil and a surfactant in a ratio selected from 0.5:99.5, 10:90, 15:85, 20:80, 25:75 30:70, 33:67, 50:50 and 75:25.

In one embodiment provided herein is a pharmaceutical composition comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix, wherein the carrier matrix comprises an oil and a surfactant in a ratio selected from 10:90, 15:85, 20:80, 25:75, 30:70 and 33:67.

In one embodiment, provided herein is a pharmaceutical composition comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix, wherein said carrier matrix comprises a mixture of a surfactant and an oil, wherein said Form B is present in an amount within the range of from about 1 to 50% w/w (wherein amount of Form B is relative to the total weight of the composition). In one embodiment, the ratio of the oil to the surfactant is about 0.5:99.5. In one embodiment, the ratio of the oil to the surfactant is about 5:95. In one embodiment, the ratio of the oil to the surfactant is about 10:90. In one embodiment, the ratio of the oil to the surfactant is about 15:85. In one embodiment, the ratio of the oil to the surfactant is about 20:80. In one embodiment, the ratio of the oil to the surfactant is about 25:75. In one embodiment, the ratio of the oil to the surfactant is about 30:70. In one embodiment, the ratio of the oil to the surfactant is about 33:67. In one embodiment, the ratio of the oil to the surfactant is about 50:50. In one embodiment, the ratio of the oil to the surfactant is about 75:25. In one embodiment, the ratio of the oil to the surfactant is about 99:1. In one embodiment, the surfactant is a non-ionic surfactant and the oil is a medium chain triglyceride. In one embodiment, the surfactant is Vitamin E TPGS. In one embodiment, the oil is Labrafac® Lipophile WL 1349.

In one embodiment, provided herein is a pharmaceutical composition comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix, wherein said carrier matrix comprises a mixture of a surfactant and an oil, wherein said Form B is present in an amount within the range of from about 1 to 40% w/w. In one embodiment, the ratio of the oil to the surfactant is about 0.5:99.5. In one embodiment, the ratio of the oil to the surfactant is about 5:95. In one embodiment, the ratio of the oil to the surfactant is about 10:90. In one embodiment, the ratio of the oil to the surfactant is about 15:85. In one embodiment, the ratio of the oil to the surfactant is about 20:80. In one embodiment, the ratio of the oil to the surfactant is about 25:75. In one embodiment, the ratio of the oil to the surfactant is about 30:70. In one embodiment, the ratio of the oil to the surfactant is about 33:67. In one embodiment, the ratio of the oil to the surfactant is about 50:50. In one embodiment, the ratio of the oil to the surfactant is about 75:25. In one embodiment, the ratio of the oil to the surfactant is about 99:1. In one embodiment, the surfactant is a non-ionic surfactant and the oil is a medium chain triglyceride. In one embodiment, the surfactant is Vitamin E TPGS. In one embodiment, the oil is Labrafac® Lipophile WL 1349.

In one embodiment, provided herein is a pharmaceutical composition comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix, wherein said carrier matrix comprises a mixture of a surfactant and an oil, wherein said Form B is present in an amount within the range of from about 1 to 30% w/w. In one embodiment, the ratio of the oil to the surfactant is about 0.5:99.5. In one embodiment, the ratio of the oil to the surfactant is about 5:95. In one embodiment, the ratio of the oil to the surfactant is about 10:90. In one embodiment, the ratio of the oil to the surfactant is about 15:85. In one embodiment, the ratio of the oil to the surfactant is about 20:80. In one embodiment, the ratio of the oil to the surfactant is about 25:75. In one embodiment, the ratio of the oil to the surfactant is about 30:70. In one embodiment, the ratio of the oil to the surfactant is about 33:67. In one embodiment, the ratio of the oil to the surfactant is about 50:50. In one embodiment, the ratio of the oil to the surfactant is about 75:25. In one embodiment, the ratio of the oil to the surfactant is about 99:1. In one embodiment, the surfactant is a non-ionic surfactant and the oil is a medium chain triglyceride. In one embodiment, the surfactant is Vitamin E TPGS. In one embodiment, the oil is Labrafac® Lipophile WL 1349.

In one embodiment, provided herein is a pharmaceutical composition comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix, wherein said carrier matrix comprises a mixture of a surfactant and an oil, wherein said Form B is present in an amount within the range of from about 20-50% w/w. In one embodiment, the ratio of the oil to the surfactant is about 0.5:99.5. In one embodiment, the ratio of the oil to the surfactant is about 5:95. In one embodiment, the ratio of the oil to the surfactant is about 10:90. In one embodiment, the ratio of the oil to the surfactant is about 15:85. In one embodiment, the ratio of the oil to the surfactant is about 20:80. In one embodiment, the ratio of the oil to the surfactant is about 25:75. In one embodiment, the ratio of the oil to the surfactant is about 30:70. In one embodiment, the ratio of the oil to the surfactant is about 33:67. In one embodiment, the ratio of the oil to the surfactant is about 50:50. In one embodiment, the ratio of the oil to the surfactant is about 75:25. In one embodiment, the ratio of the oil to the surfactant is about 99:1. In one embodiment, the surfactant is a non-ionic surfactant and the oil is a medium chain triglyceride. In one embodiment, the surfactant is Vitamin E TPGS. In one embodiment, the oil is Labrafac® Lipophile WL 1349.

In one embodiment, provided herein is a pharmaceutical composition comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix, wherein said carrier matrix comprises a mixture of a surfactant and an oil, wherein said Form B is present in an amount within the range of from about 20-40% w/w. In one embodiment, the ratio of the oil to the surfactant is about 0.5:99.5. In one embodiment, the ratio of the oil to the surfactant is about 5:95. In one embodiment, the ratio of the oil to the surfactant is about 10:90. In one embodiment, the ratio of the oil to the surfactant is about 15:85. In one embodiment, the ratio of the oil to the surfactant is about 20:80. In one embodiment, the ratio of the oil to the surfactant is about 25:75. In one embodiment, the ratio of the oil to the surfactant is about 30:70. In one embodiment, the ratio of the oil to the surfactant is about 33:67. In one embodiment, the ratio of the oil to the surfactant is about 50:50. In one embodiment, the ratio of the oil to the surfactant is about 75:25. In one embodiment, the ratio of the oil to the surfactant is about 99:1. In one embodiment, the surfactant is a non-ionic surfactant and the oil is a medium chain triglyceride. In one embodiment, the surfactant is Vitamin E TPGS. In one embodiment, the oil is Labrafac® Lipophile WL 1349.

In one embodiment, provided herein is a pharmaceutical composition comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix, wherein said carrier matrix comprises a mixture of a surfactant and an oil, wherein said Form B is present in about 25% w/w. In one embodiment, the ratio of the oil to the surfactant is about 0.5:99.5. In one embodiment, the ratio of the oil to the surfactant is about 5:95. In one embodiment, the ratio of the oil to the surfactant is about 10:90. In one embodiment, the ratio of the oil to the surfactant is about 15:85. In one embodiment, the ratio of the oil to the surfactant is about 20:80. In one embodiment, the ratio of the oil to the surfactant is about 25:75. In one embodiment, the ratio of the oil to the surfactant is about 30:70. In one embodiment, the ratio of the oil to the surfactant is about 33:67. In one embodiment, the ratio of the oil to the surfactant is about 50:50. In one embodiment, the ratio of the oil to the surfactant is about 75:25. In one embodiment, the ratio of the oil to the surfactant is about 99:1. In one embodiment, the surfactant is a non-ionic surfactant and the oil is a medium chain triglyceride. In one embodiment, the surfactant is Vitamin E TPGS. In one embodiment, the oil is Labrafac® Lipophile WL 1349.

It is to be understood that the term "about" when relating to the proportion of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B present in any of the above compositions refers to +2% by weight of the total composition.

In certain embodiments, any of the above-described pharmaceutical compositions and carrier matrices further comprises one or more release modifiers. Examples of release modifiers include, but are not limited to:

(1) Vitamin E Succinate;

(2) Cellulose derivatives, such as hydroxypropyl methylcelluloses (such as Methocel K4M, E4M, K15M and K100LV), HPMC-AS, methylcelluloses, hydroxypropylcelluloses, carboxymethylcelluloses, and sodium carboxymethylcelluloses;

(3) Polyvinylpyrrolidones [PVP's] having molecular weights greater than 58,000;

(4) Long chain (C12-C28) triglycerides, long chain (C12-C28) diglycerides, long chain (C12-C28) monoglycerides and combinations thereof, such as Compritol 888 ATO ("glyceryl behenate");

(5) Long chain alcohols (e.g., a C9 to C40 alcohols) such as stearyl alcohol, capryl alcohol, pelargonic alcohol, capric alcohol, lauryl alcohol, myristyl alcohol, cetyl alcohol, palmitoleyl alcohol, isostearyl alcohol, elaidyl alcohol, oleyl alcohol, linoleyl alcohol, polyunsaturated linolenyl alcohol, polyunsaturated ricinoleyl alcohol, arachidyl alcohol, behenyl alcohol, and/or myricyl alcohol;

(6) Castor wax;

(7) High molecular weight polyethylene glycols (PEGS) (i.e., PEGs having a molecular weight greater than 1000);

(8) Poloxamers, such as Poloxamer 188 and Poloxamer 407; and (9) Long chain (C12-C28) fatty acids.

In one embodiment, the release modifier is selected from one or more of Vitamin E succinate, Compritol 888 ATO, Methocel K4M, and stearyl alcohol.

In certain embodiments, any of the above-described pharmaceutical compositions comprises from at least 0.5% up to 50% by weight of each of said one or more release modifiers. In certain embodiments, any of the above-described pharmaceutical compositions comprises from at least 0.5% up to 40% by weight of each of said one or more release modifiers. In certain embodiments, any of the above-described pharmaceutical compositions comprises from at least 0.5% up to 30% by weight of each of said one or more release modifiers. In certain embodiments, any of the above-described pharmaceutical compositions comprises from at least 0.5% up to 20% by weight of each of said one or more release modifiers.

Accordingly, in one embodiment, provided herein is a pharmaceutical composition comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix, wherein said carrier matrix comprises at least one oil, at least one surfactant, and at least one release modifier. In one embodiment, the release modifier is selected from one or more of Vitamin E succinate, Compritol 888 ATO, Methocel K4M, and stearyl alcohol.

In one embodiment, provided herein is a pharmaceutical composition comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in at least one surfactant, wherein said composition further comprises at least one release modifier. In one embodiment, the release modifier is selected from one or more of Vitamin E succinate, Compritol 888 ATO, Methocel K4M, and stearyl alcohol.

In one embodiment, provided herein is a pharmaceutical composition comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in at least one oil, wherein said composition further comprises at least one release modifier. In one embodiment, the release modifier is selected from one or more of Vitamin E succinate, Compritol 888 ATO, Methocel K4M, and stearyl alcohol.

In one embodiment, provided herein is a pharmaceutical composition comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix, wherein said carrier matrix comprises a medium chain triglyceride and a non-ionic surfactant in a ratio selected from 10:90, 15:85 30:70 and 33:67 and said Form B is present in a range from about 20-50% w/w relative to the weight of said composition, wherein said composition further comprises one or more release modifiers. In one embodiment, said composition comprises from about 0.5% to about 20% of each of said one or more release modifiers. In one embodiment, said composition comprises from about 0.5% to about 20% of one release modifier. In one embodiment, the release modifier is selected from one or more of Vitamin E succinate, Compritol 888 ATO, Methocel K4M, and stearyl alcohol.

In certain embodiments, any of the above-described pharmaceutical compositions further comprises an antioxidant.

In one embodiment, the antioxidant is selected from d-α-tocopheryl polyethylene glycol 400 succinate, d-α-tocopheryl polyethylene glycol 1000 succinate (also known as Vitamin E TPGS), d-α-tocopheryl polyethylene glycol 2000 succinate, alpha-tocopherol, L(+)-ascorbic acid, ascorbyl palmitate, 2-tert-butyl-4-methyoxyphenol (BHA), 2,6-di-tert-butyl-4-methylphenol (BHT), fumaric acid, malic acid, monothioglycerol, potassium metabisulfite, propionic acid, propyl gallate, sodium ascorbate, sodium bisulfite and sodium metabisulfite.

In one embodiment, the antioxidant is BHT. In one embodiment, any of the above-described pharmaceutical compositions described herein further comprises about 0.001-0.5% BHT. In one embodiment, any of the above-described pharmaceutical compositions described herein further comprises about 0.001-0.15% BHT. In one embodiment, any of the above-described pharmaceutical compositions described herein further comprises about 0.001-0.1% BHT.

In one embodiment, any of the above-described pharmaceutical compositions described herein further comprises about 0.1% BHT.

In one embodiment, the pharmaceutical composition further contains a co-surfactant. Examples of co-surfactants include bis(2-ethylhexyl) sulfosuccinate sodium salt, propylene glycol monocaprylate (Capryol™ 90), glyceryl monooleate, PEG 400, polyethylene glycol 1000 (CARBOWAX™) and stearyl alcohol.

The pharmaceutical compositions may also include one or more additional pharmaceutically acceptable buffers, stabilizing agents, wetting agents, lubricating agents, preservatives, opaquing agents, glidants, processing aids, colorants, sweeteners, perfuming agents, flavoring agents, diluents and other known additives.

Also provided herein is a pharmaceutical composition comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix, wherein said carrier matrix comprises an oil and a surfactant, wherein said Form B is characterized by having at least one specific X-ray diffraction peak (2θ degrees±0.3) at about 15.9. In one embodiment, the surfactant is a non-ionic surfactant. In one embodiment, the surfactant is Vitamin E TPGS. In one embodiment, the oil is a long chain or medium chain triglyceride.

In one embodiment, the oil is Labrafac® Lipophile WL 1349. In one embodiment, the ratio of oil:surfactant is selected from 10:90, 15:85, 30:70 and 33:67. In one embodiment, the ratio of oil:surfactant is 15:85. In one embodiment, the composition further comprises an antioxidant. In one embodiment, the antioxidant is BHT.

Also provided herein is a pharmaceutical composition comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix, wherein said carrier matrix comprises an oil and a surfactant, wherein said Form B is characterized by having at least five specific X-ray diffraction peaks (2θ degrees±0.3) at about 12.3, 13.0, 15.9, 16.9 and 17.6. In one embodiment, the surfactant is a non-ionic surfactant. In one embodiment, the surfactant is Vitamin E TPGS. In one embodiment, the oil is a long chain or medium chain triglyceride. In one embodiment, the oil is Labrafac® Lipophile WL 1349. In one embodiment, the ratio of oil:surfactant is selected from 10:90, 15:85, 30:70 and 33:67. In one embodiment, the ratio of oil:surfactant is 15:85. In one embodiment, the composition further comprises an antioxidant. In one embodiment, the antioxidant is BHT.

Also provided herein is a pharmaceutical composition comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix, wherein said carrier matrix comprises an oil and a surfactant, wherein said Form B is characterized by having at least ten specific X-ray diffraction peaks (2θ degrees±0.3) at about 12.3, 13.0, 15.9, 16.9, 17.6, 20.4, 21.5, 24.6, 25.2 and 25.9. In one embodiment, the surfactant is a non-ionic surfactant. In one embodiment, the surfactant is Vitamin E TPGS. In one embodiment, the oil is a long chain or medium chain triglyceride. In one embodiment, the oil is Labrafac® Lipophile WL 1349. In one embodiment, the ratio of oil:surfactant is selected from 10:90, 15:85, 30:70 and 33:67. In one embodiment, the ratio of oil:surfactant is 15:85. In one embodiment, the composition further comprises an antioxidant. In one embodiment, the antioxidant is BHT.

X-ray diffraction (XRD) analysis of compositions described herein was conducted using a Rigaku X-Ray diffractometer (model Ultima III) operating with a Cu radiation source at 40 kW, 40 mA. Round standard aluminum sample holders with round zero background, and/or quartz plates were used for sample preparation. The scanning parameters were from a range of about 3-40 degree 2θ (±0.3 degrees) and a continuous scan at a rate of about 2 degrees 2θ/minute. 2θ calibration was performed using a Si standard.

The skilled person is aware that there may be interference with the above XRD peaks for 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B listed for the compositions, depending on the particular excipients comprising the carrier matrix and other components in the composition. Further, the skilled person is aware that subtraction of the X-ray diffraction peaks related to the carrier matrix and/or other components in the formulation may be necessary in order to identify the characteristic peaks for Form B.

In addition, the skilled person is aware that an XRD pattern may be obtained which has one or more measurement errors depending on measurement conditions (such as equipment, sample preparation or instrument used). In particular, it is generally known that intensities in an X-ray diffraction pattern may fluctuate depending on measurement conditions and sample preparation. For example, the skilled person will realize that the relative intensity of peaks can be affected by, for example, grains above 30 microns in size and non-unitary aspect ratios, which may affect analysis of samples. The skilled person will also realize that the position of reflections can be affected by the precise height at which the sample sits in the diffractometer and the zero calibration of the diffractometer. The surface planarity of the sample may also have a small effect. Hence a person skilled in the art will appreciate that the diffraction pattern data presented herein is not to be construed as absolute.

Preparation of Compositions

In one embodiment, provided herein are processes for preparing a pharmaceutical composition comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix, wherein said carrier matrix comprises a surfactant and an oil. In one embodiment, the composition further comprises an antioxidant.

Process 1 for Preparing a Pharmaceutical Composition

In one embodiment, a process for preparing a pharmaceutical composition comprises (i) stirring a mixture of a surfactant and an oil at a temperature sufficient to provide a liquefied homogeneous carrier matrix; and (ii) adding 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B to the carrier matrix with stirring at a temperature sufficient to maintain said carrier matrix in a liquefied state to provide a liquefied homogeneous suspension of said Form B in said carrier matrix.

In one embodiment of Process 1, step (i) and/or step (ii) is performed under a stream of nitrogen.

In one embodiment, Process 1 further comprises adding an antioxidant in step (i) or step (ii). In one embodiment, the antioxidant is BHT.

In one embodiment, Process 1 further comprises adding one or more release modifiers in step (ii).

In one embodiment of Process 1, the process further comprises (iii) transferring aliquots of said liquefied homogenous suspension obtained in step (ii) into capsules and allowing said suspension to cool in said capsules to provide a liquid, solid semi-solid or solid form of the suspension within the capsules.

In one embodiment of Process 1, the surfactant is a nonionic surfactant. In one embodiment, the surfactant is Vitamin E TPGS. In one embodiment, the oil is a long chain or medium chain triglyceride. In one embodiment, the oil is Labrafac® Lipophile WL 1349.

In one embodiment of Process 1, the mixture in step (i) is heated to a temperature between about 40 to 60° C. (i.e., 50° C.±10° C.). In one embodiment, the mixture in step (i) is heated to a temperature between about 45 to 50° C. (i.e., 47.5° C.±2.5° C.).

Process 2 for Preparing a Pharmaceutical Composition

In one embodiment, a process for preparing a pharmaceutical composition comprises (i) homogenizing an oil at a temperature sufficient to melt the oil; (ii) homogenizing a surfactant at a temperature sufficient to melt the surfactant; (iii) combining said molten oil and molten surfactant with stirring at a temperature that maintains the combination in a molten state to form a molten homogenous carrier matrix; and (iv) adding 1-(3-tert-butyl-1-p-tolyl-1H-pyrazol-5-yl)-3-(5-fluoro-2-(1-(2-hydroxyethyl)-1H-indazol-5-yloxy)benzyl) urea hydrochloride Form B to said molten homogenous carrier matrix with stirring at a temperature that maintains said carrier matrix in a molten state to provide a molten homogeneous suspension of said Form B in said carrier matrix.

In one embodiment of Process 2, step (i) and/or step (i) and/or step (iii) and/or step (iv) is performed under a stream of nitrogen.

In one embodiment, Process 2 further comprises adding an antioxidant in step (iii) or step (iv). In one embodiment, the antioxidant is BHT.

In one embodiment, Process 2 further comprises adding one or more release modifiers in step (iii) or (iv).

In one embodiment, Process 2 further comprises (v) transferring aliquots of said molten homogenous suspension obtained in step (iv) into capsules and allowing said suspension to cool in said capsules to provide a liquid, solid semi-solid or solid form of the suspension within the capsules.

In one embodiment of Process 2, the surfactant is a nonionic surfactant. In one embodiment, the surfactant is Vitamin E TPGS. In one embodiment, the oil is a long chain or medium chain triglyceride. In one embodiment, the oil is Labrafac® Lipophile WL 1349.

In one embodiment of Process 2, the mixture in step (iii) and/or (iv) is heated to a temperature between about 40 to 60° C. (i.e., 50° C.±10° C.). In one embodiment, the mixture in step (iii) and/or (iv) is heated to a temperature between about 45 to 50° C. (i.e., 47.5° C.±2.5° C.).

Process 3 for Preparing a Pharmaceutical Composition

In one embodiment, a process for preparing a pharmaceutical composition comprises (i) homogenizing an oil at a temperature sufficient to melt the oil; (ii) homogenizing a surfactant at a temperature sufficient to melt the surfactant; and (iii) combining said molten oil, said molten surfactant, and 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B with stirring at a temperature that maintains said combination in a molten state to provide a molten homogeneous suspension of said Form B in a carrier matrix.

In one embodiment of Process 3, the mixture in step (i) and/or (ii) and/or (iii) is performed under a stream of nitrogen.

In one embodiment, Process 3 further comprises adding an antioxidant in step (iii). In one embodiment, the antioxidant is BHT.

In one embodiment, Process 3 further comprises adding one or more release modifiers in step (iii).

In one embodiment of Process 3, the process further comprises (iv) transferring aliquots of said molten homogenous suspension obtained in step (iii) into capsules and allowing said suspension to cool in said capsules to provide a liquid, solid semi-solid or solid form of the suspension within the capsules.

In one embodiment of Process 3, the surfactant is a nonionic surfactant. In one embodiment, the surfactant is Vitamin E TPGS. In one embodiment, the oil is a long chain or medium chain triglyceride. In one embodiment, the oil is Labrafac® Lipophile WL 1349.

In one embodiment of Process 3, the mixture step (iii) is heated to a temperature between about 40 to 60° C. (i.e., 50° C.±10° C.). In one embodiment, the mixture step (iii) is heated to a temperature between about 45 to 50° C. (i.e., 47.5° C.±2.5° C.).

Each of the above described processes for preparing a pharmaceutical composition is also suitable for preparing compositions comprising two or more surfactants. Each of the above described processes for preparing a pharmaceutical composition is also suitable and adaptable for preparing compositions comprising one or more surfactants and two or more oils. Each of the above described processes is also suitable and adaptable for preparing compositions comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix comprises a surfactant but does not include an oil. Each of the above described processes is also suitable and adaptable for preparing compositions comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix that comprises an oil but does not include a surfactant.

As an alternative to transferring any of the homogenous suspensions formed in Process 1, 2 or 3 into capsules, the homogenous suspensions can be formed into microparticles, granules, beads, pellets or pastilles. The microparticles, granules, beads, or pellets can then be filled into capsules, or can be further blended with one or more excipients and then tableted or encapsulated. Pastilles can be administered to a patient as a naked unit dosage form. Microparticles, granules, beads, pellets or pastilles can be prepared by methods well known to persons skilled in the art, including but not limited to spray congealing, freeze pelletization, melt granulation (with other excipients), hot-melt-extrusion, and hot-melt-extrusion spheronization (optionally with other excipients).

Alternatively the homogenous suspension could be added to any aqueous beverage, including but not limited to, water, juices (apple, orange, etc.), carbonated beverages, etc., to be administered as a drinkable liquid oral formulation.

Also provided herein is a pharmaceutical composition prepared by the method comprising (i) stirring a mixture of a surfactant and an oil at a temperature sufficient to provide a liquefied homogeneous carrier matrix optionally in a nitrogen atmosphere; and (ii) adding 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B to the carrier matrix with stirring at a temperature sufficient to maintain said carrier matrix in a liquefied state and optionally under a nitrogen atmosphere, thereby providing said pharmaceutical composition comprising a liquefied homogeneous suspension of said Form B in said carrier matrix. In one embodiment said composition is prepared by the method which further comprises (iv) transferring aliquots of said molten homogenous suspension obtained in step (iii) into capsules and allowing said suspension to cool in said capsules to provide said composition comprising a liquid, solid semi-solid or solid form of the suspension within the capsules.

Also provided herein is a pharmaceutical composition prepared by the method comprising (i) homogenizing an oil at a temperature sufficient to melt the oil optionally under a nitrogen atmosphere; (ii) homogenizing a surfactant at a temperature sufficient to melt the surfactant optionally under a nitrogen atmosphere; (iii) combining said molten oil and molten surfactant with stirring at a temperature that maintains the combination in a molten state and optionally under a nitrogen atmosphere to form a molten homogenous carrier matrix; and (iv) adding 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B to said molten homogenous carrier matrix with stirring at a temperature that maintains said carrier matrix in a molten state and optionally under a nitrogen atmosphere, thereby providing said composition comprising a molten homogeneous suspension of said Form B in said carrier matrix. In one embodiment said composition is prepared by the method which further comprises (v) transferring aliquots of said molten homogenous suspension obtained in step (iv) into capsules and allowing said suspension to cool in said capsules to provide said composition comprising a liquid, solid semi-solid or solid form of the suspension within the capsules.

Also provided herein is a pharmaceutical composition prepared by the method comprising (i) homogenizing an oil at a temperature sufficient to melt the oil; (ii) homogenizing a surfactant at a temperature sufficient to melt the surfactant; and (iii) combining said molten oil, said molten surfactant, and 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B with stirring at a temperature that maintains said combination in a molten state, thereby providing said composition comprising a molten homogeneous suspension of said Form B in a carrier matrix. In one embodiment said composition is prepared by the method which further comprises (iv) transferring aliquots of said molten homogenous suspension obtained in step (iii) into capsules and allowing said suspension to cool in said capsules to provide said composition comprising a liquid, solid semi-solid or solid form of the suspension within the capsules.

Drug Loads

In one embodiment, certain pharmaceutical composition described herein comprising novel physical forms of 1-(3-tert-butyl-1-p-tolyl-1H-pyrazol-5-yl)-3-(5-fluoro-2-(1-(2-hydroxyethyl)-1H-indazol-5-yloxy)benzyl)urea have unexpectedly high drug loads.

It is known that it can be difficult to achieve suitable bioavailability with an orally administered formulation containing a BCS Class II compound at a high drug load and high dose, even when solubilized in a carrier matrix. The increased oral bioavailability of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B when formulated as certain compositions as described herein is even more unexpected due to the fact that said Form B is a crystalline suspension in the carrier matrix (rather than solubilized in the carrier matrix), which adds an additional thermodynamic barrier to increased bioavailability.

Pharmaceutical compositions having high drug loads are advantageous in that larger amounts of a drug per unit dosage (e.g., per pill or capsule) are capable of being administered to a patient in need thereof. This can significantly reduce burdens on the patient. For example, larger amounts of a drug per unit dosage means that the number of pills needed per dose in order to administer an effective amount of the drug can be reduced, which can increase patient compliance.

In one embodiment, provided herein is a pharmaceutical composition comprising about 1279 mg of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B (which is equivalent to about 1200 mg of 1-(3-tert-butyl-1-p-tolyl-1H-pyrazol-5-yl)-3-(5-fluoro-2-(1-(2-hydroxyethyl)-1H-indazol-5-yloxy)benzyl)urea as the free base), wherein the composition comprises about 20-50% w/w of Form B suspended in a carrier matrix comprising an oil and a surfactant. In one embodiment, the carrier matrix comprises an oil and surfactant in a ratio selected from 10:90, 15:85, 20:80, 25:75, 30:70 and 33:67. In one embodiment, the ratio of the oil to the surfactant is 15:85. In one embodiment, the composition comprises about 25% w/w of Form B. In one embodiment, the surfactant is a non-ionic surfactant. In one embodiment, the surfactant is Vitamin E TPGS. In one embodiment, the oil is a long chain or medium chain triglyceride. In one embodiment, the oil is Labrafac® Lipophile WL 1349. In one embodiment, the composition further comprises an antioxidant. In one embodiment, the antioxidant is BHT.

In one embodiment, provided herein is a pharmaceutical composition comprising about 1066 mg of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B (which is equivalent to about 1000 mg of 1-(3-tert-butyl-1-p-tolyl-1H-pyrazol-5-yl)-3-(5-fluoro-2-(1-(2-hydroxyethyl)-1H-indazol-5-yloxy)benzyl)urea as the free base), wherein the composition comprises about 20-50% w/w of Form B suspended in a carrier matrix comprising an oil and a surfactant. In one embodiment, the carrier matrix comprises an oil and surfactant in a ratio selected from 10:90, 15:85, 20:80, 25:75, 30:70 and 33:67. In one embodiment, the ratio of the oil to the surfactant is 15:85. In one embodiment, the composition comprises about 25% w/w of said Form B. In one embodiment, the surfactant is a non-ionic surfactant. In one embodiment, the surfactant is Vitamin E TPGS. In one embodiment, the oil is a long chain or medium chain triglyceride. In one embodiment, the oil is Labrafac® Lipophile WL 1349. In one embodiment, the composition further comprises an antioxidant. In one embodiment, the antioxidant is BHT.

In one embodiment, provided herein is a pharmaceutical composition comprising about 853 mg of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B (which is equivalent to about 800 mg of 1-(3-tert-butyl-1-p-tolyl-1H-pyrazol-5-yl)-3-(5-fluoro-2-(1-(2-hydroxyethyl)-1H-indazol-5-yloxy)benzyl)urea as the free base), wherein the composition comprises about 20-50% w/w of Form B suspended in a carrier matrix comprising an oil and a surfactant. In one embodiment, the carrier matrix comprises an oil and surfactant in a ratio selected from 10:90, 15:85, 20:80, 25:75, 30:70 and 33:67. In one embodiment, the ratio of the oil to the surfactant is 15:85. In one embodiment, the composition comprises about 25% w/w of said Form B. In one embodiment, the surfactant is a non-ionic surfactant. In one embodiment, the surfactant is Vitamin E TPGS. In one embodiment, the oil is a long chain or medium chain triglyceride. In one embodiment, the oil is Labrafac® Lipophile WL 1349. In one embodiment, the composition further comprises an antioxidant. In one embodiment, the antioxidant is BHT.

In one embodiment, provided herein is a pharmaceutical composition comprising about 640 mg of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B (which is equivalent to about 600 mg of 1-(3-tert-butyl-1-p-tolyl-1H-pyrazol-5-yl)-3-(5-fluoro-2-(1-(2-hydroxyethyl)-1H-indazol-5-yloxy)benzyl)urea as the free base), wherein the composition comprises about 20-50% w/w of Form B suspended in a carrier matrix comprising an oil and a surfactant. In one embodiment, the carrier matrix comprises an oil and surfactant in a ratio selected from 10:90, 15:85, 20:80, 25:75, 30:70 and 33:67. In one embodiment, the ratio of the oil to the surfactant is 15:85. In one embodiment, the composition comprises about 25% w/w of said Form B. In one embodiment, the surfactant is a non-ionic surfactant. In one embodiment, the surfactant is Vitamin E TPGS. In one embodiment, the oil is a long chain or medium chain triglyceride. In one embodiment, the oil is Labrafac® Lipophile WL 1349. In one embodiment, the composition further comprises an antioxidant. In one embodiment, the antioxidant is BHT.

In one embodiment, provided herein is a pharmaceutical composition comprising about 426 mg of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B (which is equivalent to about 400 mg of 1-(3-tert-butyl-1-p-tolyl-1H-pyrazol-5-yl)-3-(5-fluoro-2-(1-(2-hydroxyethyl)-1H-indazol-5-yloxy)benzyl)urea as the free base), wherein the composition comprises about 20-50% w/w of Form B suspended in a carrier matrix comprising an oil and a surfactant. In one embodiment, the carrier matrix comprises an oil and surfactant in a ratio selected from 10:90, 15:85, 20:80, 25:75, 30:70 and 33:67. In one embodiment, the ratio of the oil to the surfactant is 15:85. In one embodiment, the composition comprises about 25% w/w of said Form B. In one embodiment, the surfactant is a non-ionic surfactant. In one embodiment, the surfactant is Vitamin E TPGS. In one embodiment, the oil is a long chain or medium chain triglyceride. In one embodiment, the oil is Labrafac® Lipophile WL 1349. In one embodiment, the composition further comprises an antioxidant. In one embodiment, the antioxidant is BHT.

In one embodiment, provided herein is a pharmaceutical composition comprising about 213 mg of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B (which is equivalent to about 200 mg of 1-(3-tert-butyl-1-p-tolyl-1H-pyrazol-5-yl)-3-(5-fluoro-2-(1-(2-hydroxyethyl)-1H-indazol-5-yloxy)benzyl)urea as the free base), wherein the composition comprises about 20-50% w/w of Form B suspended in a carrier matrix comprising an oil and a surfactant. In one embodiment, the carrier matrix comprises an oil and surfactant in a ratio selected from 10:90, 15:85, 20:80, 25:75, 30:70 and 33:67. In one embodiment, the ratio of the oil to the surfactant is 15:85. In one embodiment, the composition comprises about 25% w/w of said Form B. In one embodiment, the surfactant is a non-ionic surfactant. In one embodiment, the surfactant is Vitamin E TPGS. In one embodiment, the oil is a long chain or medium chain triglyceride. In one embodiment, the oil is Labrafac® Lipophile WL 1349. In one embodiment, the composition further comprises an antioxidant. In one embodiment, the antioxidant is BHT.

In one embodiment, provided herein is a pharmaceutical composition comprising about 53 mg of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B (which is equivalent to about 50 mg of 1-(3-tert-butyl-1-p-tolyl-1H-pyrazol-5-yl)-3-(5-fluoro-2-(1-(2-hydroxyethyl)-1H-indazol-5-yloxy)benzyl)urea as the free base), wherein the composition comprises about 20-50% w/w of Form B suspended in a carrier matrix comprising an oil and a surfactant. In one embodiment, the carrier matrix comprises an oil and surfactant in a ratio selected from 10:90, 15:85, 20:80, 25:75, 30:70 and 33:67. In one embodiment, the ratio of the oil to the surfactant is 15:85. In one embodiment, the composition comprises about 25% w/w of said Form B. In one embodiment, the surfactant is a non-ionic surfactant. In one embodiment, the surfactant is Vitamin E TPGS. In one embodiment, the oil is a long chain or medium chain triglyceride. In one embodiment, the oil is Labrafac® Lipophile WL 1349. In one embodiment, the composition further comprises an antioxidant. In one embodiment, the antioxidant is BHT.

In one embodiment, any of the pharmaceutical compositions described herein is formulated in single or multiple unit dosage form suitable for once daily oral administration.

In one embodiment, any of the pharmaceutical compositions described herein is formulated in single or multiple unit dosage form suitable for twice daily oral administration.

The phrase "once daily administration" means a single dose of a composition disclosed herein is administered once within a 24 hour period, ±1 hour.

The phrase "twice daily administration" means a single dose of a composition disclosed herein is administered twice within a 24 hour period, ±1 hour.

Stability Studies

Pharmaceutical compositions described herein comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix, wherein the carrier matrix comprises a surfactant and an oil and said composition optionally further comprises an antioxidant, are chemically and physically stable under the conditions in which they are processed, handled and stored.

As used herein, the term "chemically stable" means that there is minimal amount of degradation of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B and/or any other components of the composition (including the carrier matrix). That is, the formulation meets the criteria regarding the stability of these components required in order for the composition to be approved for administration to humans.

As used herein, the terms "physically stable" means that there is no change in the polymorphic form of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B, and there is no change in the particle size of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B, and 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B remains as a well-dispersed suspension in the carrier matrix.

One advantage of compositions described herein which are chemically and physically stable during processing and storage is that acceptable absorption and/or bioavailability of 1-(3-tert-butyl-1-p-tolyl-1H-pyrazol-5-yl)-3-(5-fluoro-2-(1-(2-hydroxyethyl)-1H-indazol-5-yloxy)benzyl)urea can be achieved upon dosing. Another advantage is that compositions described herein can be reproducibly manufactured on various manufacturing scales, including commercial scales. A further advantage is that compositions described herein can have shelf lives greater than or equal to two years.

A primary degradant of 1-(3-tert-butyl-1-p-tolyl-1H-pyrazol-5-yl)-3-(5-fluoro-2-(1-(2-hydroxyethyl)-1H-indazol-5-yloxy)benzyl)urea (either as the free base or the HCl salt) has been found to be 3-(tert-butyl)-1-(p-tolyl)-1H-pyrazol-5-amine, which results from cleavage of the urea bond as shown below.

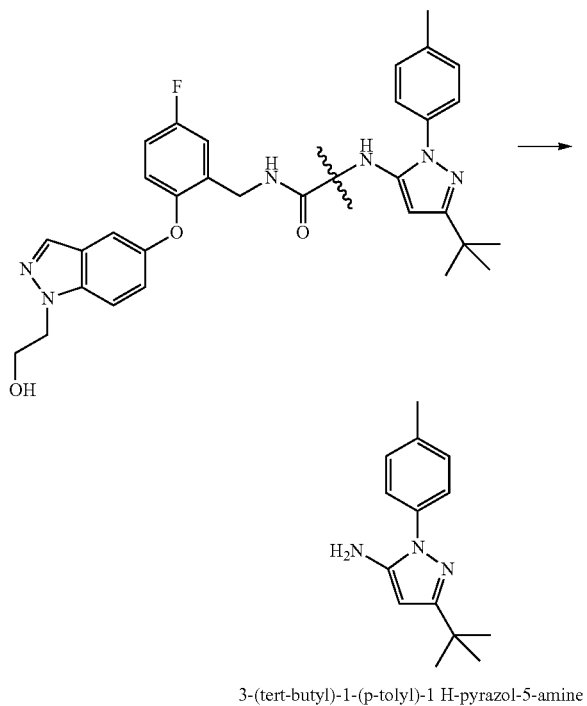

3-(tert-butyl)-1-(p-tolyl)-1 H-pyrazol-5-amine

Pharmaceutical compositions described herein comprising a 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix comprising a surfactant and an oil, wherein the composition optionally further comprises an antioxidant, were found to have lower amounts of 3-(tert-butyl)-1-(p-tolyl)-1H-pyrazol-5-amine when compared to compositions comprising amorphous 1-(3-tert-butyl-1-p-tolyl-1H-pyrazol-5-yl)-3-(5-fluoro-2-(1-(2-hydroxyethyl)-1H-indazol-5-yloxy)benzyl) urea formulated in the same carrier matrix.

Accordingly, in one embodiment provided herein is a pharmaceutical composition comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix comprising a surfactant and an oil, wherein said composition comprises less than or equal to 300 parts-per-million (ppm) of 3-(tert-butyl)-1-(p-tolyl)-1H-pyrazol-5-amine after storage at 40° C./75% relative humidity for 4 weeks. In one embodiment, said composition comprises less than or equal to 150 ppm of 3-(tert-butyl)-1-(p-tolyl)-1H-pyrazol-5-amine after storage at 40° C./75% relative humidity for 4 weeks. In one embodiment, said composition comprises less than or equal to 100 ppm of 3-(tert-butyl)-1-(p-tolyl)-1H-pyrazol-5-amine after storage at 40° C./75% relative humidity for 4 weeks. In one embodiment, said composition comprises less than or equal to 55 ppm of 3-(tert-butyl)-1-(p-tolyl)-1H-pyrazol-5-amine after storage at 40° C./75% relative humidity for 4 weeks. In one embodiment, the surfactant is a non-ionic surfactant. In one embodiment, the surfactant is Vitamin E TPGS. In one embodiment, the oil is a long chain or medium chain triglyceride. In one embodiment, the oil is Labrafac® Lipophile WL 1349. In one embodiment, the ratio of oil:surfactant is selected from 10:90, 15:85, 30:70 and 33:67. In one embodiment, the ratio of oil:surfactant is 15:85. In one embodiment, the composition further comprises an antioxidant. In one embodiment, the antioxidant is BHT.

In one embodiment, provided herein is a pharmaceutical composition comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix, wherein said carrier matrix comprises a medium chain triglyceride and a non-ionic surfactant in a ratio selected from 10:90, 15:85 30:70 and 33:67 and said Form B is present in a range from about 20-50% w/w relative to the weight of said composition, wherein said composition optionally further comprises an antioxidant, wherein said composition comprises less than or equal to 300 ppm of 3-(tert-butyl)-1-(p-tolyl)-1H-pyrazol-5-amine after storage at 40° C./75% relative humidity for 4 weeks. In one embodiment, said composition comprises less than or equal to 100 ppm of 3-(tert-butyl)-1-(p-tolyl)-1H-pyrazol-5-amine after storage at 40° C./75% relative humidity for 4 weeks. In one embodiment, said composition comprises less than or equal to 55 ppm of 3-(tert-butyl)-1-(p-tolyl)-1H-pyrazol-5-amine after storage at 40° C./75% relative humidity for 4 weeks. In one embodiment, said surfactant is Vitamin E TPGS and said oil is Labrafac® Lipophile WL 1349. In one embodiment, the composition further comprises an antioxidant. In one embodiment, the antioxidant is BHT.

In one embodiment provided herein is a pharmaceutical composition comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix comprising a surfactant and an oil, wherein said composition comprises less than or equal to 300 ppm of 3-(tert-butyl)-1-(p-tolyl)-1H-pyrazol-5-amine after storage at 25° C./60% relative humidity for one year. In one embodiment, the composition comprises less than or equal to 100 ppm of 3-(tert-butyl)-1-(p-tolyl)-1H-pyrazol-5-amine after storage at 25° C./60% relative humidity for one year. In one embodiment, the composition comprises less than or equal to 70 ppm of 3-(tert-butyl)-1-(p-tolyl)-1H-pyrazol-5-amine after storage at 25° C./60% relative humidity for one year. In one embodiment, the surfactant is a non-ionic surfactant. In one embodiment, the surfactant is Vitamin E TPGS. In one embodiment, the oil is a long chain or medium chain triglyceride. In one embodiment, the oil is Labrafac® Lipophile WL 1349. In one embodiment, the ratio of the oil to surfactant is 15:85. In one embodiment, the composition further comprises an antioxidant. In one embodiment, the antioxidant is BHT.

In one embodiment, provided herein is a composition comprising 1-(3-tert-butyl-1-p-tolyl-1H-pyrazol-5-yl)-3-(5-fluoro-2-(1-(2-hydroxyethyl)-1H-indazol-5-yloxy)benzyl) urea hydrochloride Form B suspended in a carrier matrix, wherein said carrier matrix comprises a medium chain triglyceride and a non-ionic surfactant in a ratio selected from 10:90, 15:85 30:70 and 33:67 and said Form B is present in a range from about 20-50% w/w relative to the weight of said composition, wherein said composition comprises less than or equal to 100 ppm of 3-(tert-butyl)-1-(p-tolyl)-1H-pyrazol-5-amine after storage at 25° C./60% relative humidity for 1 year. In one embodiment, said composition comprises less than or equal to 70 ppm of 3-(tert-butyl)-1-(p-tolyl)-1H-pyrazol-5-amine after storage at 25° C./60% relative humidity for 1 year. In one embodiment, said surfactant is Vitamin E TPGS and said oil is Labrafac® Lipophile WL 1349. In one embodiment, the composition further comprises an antioxidant. In one embodiment, the antioxidant is BHT.

Also provided herein is a method comprising storing 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B under conditions such that said composition contains less than 300 ppm of 3-(tert-butyl)-1-(p-tolyl)-1H-pyrazol-5-amine after storage at 40° C./75% relative humidity for 4 weeks, said method comprising formulating Form B as a suspension in carrier matrix comprising a surfactant and an oil. In one embodiment, the surfactant is a non-ionic surfactant. In one embodiment, the surfactant is Vitamin E TPGS. In one embodiment, the oil is a long chain or medium chain triglyceride. In one embodiment, the oil is Labrafac® Lipophile WL 1349. In one embodiment, the ratio of the oil to surfactant is 15:85. In one embodiment, the composition further comprises an antioxidant. In one embodiment, the antioxidant is BHT.

Also provided herein is a method comprising storing 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B under conditions such that said composition contains less than 300 ppm of 3-(tert-butyl)-1-(p-tolyl)-1H-pyrazol-5-amine after storage at 25° C./60% relative humidity for 1 year, said method comprising formulating Form B as a suspension in carrier matrix comprising a surfactant and an oil. In one embodiment, the surfactant is a non-ionic surfactant. In one embodiment, the surfactant is Vitamin E TPGS. In one embodiment, the oil is a long chain or medium chain triglyceride. In one embodiment, the oil is Labrafac® Lipophile WL 1349. In one embodiment, the ratio of the oil to surfactant is 15:85. In one embodiment, the composition further comprises an antioxidant. In one embodiment, the antioxidant is BHT. In one embodiment, the composition comprises about 20-50% w/w of said Form B.

The stability of pharmaceutical compositions comprising one or more release modifiers was also investigated (Example 6A). In this study, the amount of the degradant 2-(5-(2-(aminomethyl)-4-fluorophenoxy)-1H-indazol-1-yl)ethanol present in the composition was measured after storage for 6 months at 30° C./75% RH. This degradant results from cleavage of the urea bond as shown below.

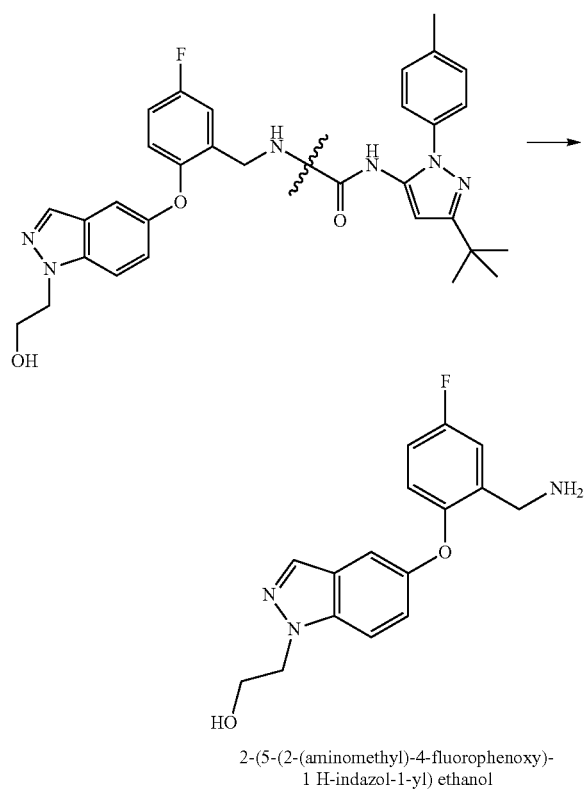

2-(5-(2-(aminomethyl)-4-fluorophenoxy)-1H-indazol-1-yl) ethanol

Pharmaceutical compositions described herein comprising a 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix comprising a surfactant and an oil, wherein the composition further comprises one or two release modifiers and optionally further comprises antioxidant, were found to have similar amounts of 2-(5-(2-(aminomethyl)-4-fluorophenoxy)-1H-indazol-1-yl)ethanol when compared to similar compositions which do not comprise release modifier(s). Accordingly, release modifier(s) do not appear to affect the stability of compositions described herein.

Dissolution Profiles

The absorption of drugs from pharmaceutical compositions after oral administration depends, among other factors, on the liberation of the drug from the pharmaceutical composition, its dissolution or solubility of the drug in physiological conditions, and the drug's permeability through the gastrointestinal tract. Due to the critical nature of the two initial stages, dissolution tests in vitro can be relevant to predict the performance of the drug in vivo. Rapid dissolution of an orally administered active agent is desirable, as faster dissolution generally leads to faster onset of action and greater bioavailability. To improve the dissolution profile and bioavailability of a drug such as 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B, it is useful to formulate the drug in a manner that increases the drug's solubility so that it can attain a dissolution level close to 100%. It was discovered that compositions described herein have an improved in vitro dissolution profile when compared to amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea formulated as a powder in capsule.

Dissolution is typically measured in a medium which shows discrimination between formulations. An exemplary dissolution media is 0.1 M HCl aqueous solution at pH 1 containing between about 0.05%-0.1% cetyl trimethylammonium bromide (CTAB).

Any suitable method well known to persons skilled in the art can be used for measuring dissolution, such as the rotating blade method or the USP Apparatus II (paddle) method. Determination of the amount of material dissolved can be carried out, for example by spectrophotometry.

In one embodiment, the dissolution is measured by Dissolution Method 1, which comprises placing said composition in about 900 mL of a dissolution media comprising a mixture of 0.1 M HCl and 0.1% CTAB at pH 1 at 37° C., optionally using spiral wire capsule sinkers for compositions in capsule form, and using a USP II apparatus with a 75 rpm paddle speed. In one embodiment of Dissolution Method 1, the dissolution is measured by UV spectrophotometry.

In one embodiment, the dissolution is measured by Dissolution Method 2, which comprises placing said composition in about 900 mL of a dissolution media comprising a mixture of 0.1 M HCl and 0.05% CTAB at pH 1 at 37° C., optionally using spiral wire capsule sinkers for compositions in capsule form, and stirring the mixture at 75 rpm using a USP II apparatus. Dissolution Method 2 is a more discriminating media for 1-(3-tert-butyl-1-p-tolyl-1H-pyrazol-5-yl)-3-(5-fluoro-2-(1-(2-hydroxyethyl)-1H-indazol-5-yloxy)benzyl) urea hydrochloride Form B and will result in an equivalent or lower overall percent dissolution of the compound relative to Dissolution Method 1. In one embodiment of Dissolution Method 2, the dissolution is measured by UV spectrophotometry.

In one embodiment, provided herein is a pharmaceutical composition comprising about 1 to 213 mg of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix, wherein said carrier matrix comprises 0-60% w/w of an oil and 40-100% w/w of a surfactant, wherein said Form B is present in a range from about 1-50% w/w, said composition having a dissolution profile in which within 30 minutes about 30-100% of said Form B is dissolved when said dissolution is measured by Dissolution Method 2. In one embodiment, said composition has a dissolution profile in which within 45 minutes about 40-100% of said Form B is dissolved when said dissolution is measured by Dissolution Method 2. In one embodiment, said composition has a dissolution profile in which within 60 minutes about 50-100% of said Form B is dissolved when said dissolution is measured by Dissolution Method 2. In one embodiment, said oil is a long chain or medium chain triglyceride and said surfactant is a non-ionic surfactant. In one embodiment, the composition comprises about 1-40% w/w of said Form B. In one embodiment, the composition comprises about 20-40% w/w of said Form B. In one embodiment, said Form B is micronized.

In one embodiment, provided herein is a pharmaceutical composition comprising about 1 to about 213 mg of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix, wherein said carrier matrix comprises either Vitamin E TPGS or a mixture of Labrafac® Lipophile WL 1349 and Vitamin E TPGS in a ratio selected from 10:90, 15:85, 30:70 and 33:67 and wherein said Form B is present in a range from about 20-40% w/w, said composition having a dissolution profile in which within about 30 minutes about 45-100% of said Form B is dissolved when said dissolution is measured by Dissolution Method 2. In one embodiment, said composition has a dissolution profile in which within 45 minutes about 70-100% of said Form B is dissolved when said dissolution is measured by Dissolution Method 2. In one embodiment, said composition has a dissolution profile in which within about 60 minutes about 80-100% of said Form B is dissolved when said dissolution is measured by Dissolution Method 2. In one embodiment, the composition comprises about 213 mg of said Form B. In one embodiment, said Form B is micronized.

In one embodiment, provided herein is a pharmaceutical composition comprising about 213 mg of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix, wherein said carrier matrix comprises Vitamin E TPGS or a mixture of Labrafac® Lipophile WL 1349 and Vitamin E TPGS in a ratio selected from 10:90, 15:85 and 30:70, wherein Form B is present in a range from about 20-40% w/w, said composition having the dissolution profile as shown in Table A when said dissolution is measured by Dissolution Method 2. In one embodiment, said Form B is micronized.

TABLE A

| Time (minutes) | Average % of Form B dissolved | Range of Form B dissolved |
| --- | --- | --- |
| 30 | 79 | 44-96 |
| 45 | 87 | 69-102 |
| 60 | 91 | 82-104 |

Delayed Release Dissolution Profiles

In certain embodiments, it is desirable to delay the dissolution of an orally administered active agent such as 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B. Modified release may offer several advantages over immediate release dosage forms. Some of the potential benefits of a modified release profile include improved patient compliance due to a reduction of the dosing frequency, reduction of the dose required for maintain therapeutic plasma concentrations over an extended period of time, reduction in potential adverse side effects which could be related to plasma $C_{max}$, reduction in potential adverse side effects which could be related to plasma concentrations above the therapeutic levels, minimize local side effects due to the route of administration, minimize accumulation of plasma drug levels with chronic dosing, and potential improved bioavailability.

Accordingly, in one embodiment pharmaceutical compositions and carrier matrices described herein further comprise one or more release modifiers. Example 5A describes dissolution studies and provides dissolution profiles of various pharmaceutical compositions comprising one or more release modifiers. A comparison of the dissolution profiles of formulations not comprising a release modifier (see formulations I and M in Example 5) with formulations comprising one or two release modifiers (Example 5A) illustrates that 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B is released at a slower rate from formulations comprising one or more release modifiers compared to the amount released for formulations I and M.

Reduced Variability in Pharmacokinetic Profiles

Also provided herein are compositions having reduced inter-patient variability in pharmacokinetic profiles and pharmacokinetic parameters when administered to healthy human subjects. In particular, certain compositions described herein have:

(1) reduced variability in $C_{max}$ of 1-(3-tert-butyl-1-p-tolyl-1H-pyrazol-5-yl)-3-(5-fluoro-2-(1-(2-hydroxyethyl)-1H-indazol-5-yloxy)benzyl)urea when assayed in the plasma of a human subject following oral administration of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B relative to that for amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea when orally administered at the same dosage as a powder in capsule; and/or (2) reduced variability in $AUC_{inf}$ of 1-(3-tert-butyl-1-p-tolyl-1H-pyrazol-5-yl)-3-(5-fluoro-2-(1-(2-hydroxyethyl)-1H-indazol-5-yloxy)benzyl)urea when assayed in the plasma of a human subject following oral administration of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B relative to that for amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea when orally administered at the same dosage as a powder in capsule; and/or (3) reduced variability in $T_{max}$ of 1-(3-tert-butyl-1-p-tolyl-1H-pyrazol-5-yl)-3-(5-fluoro-2-(1-(2-hydroxyethyl)-1H-indazol-5-yloxy)benzyl)urea when assayed in the plasma of a human subject following oral administration of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B relative to that for amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea when orally administered at the same dosage as a powder in capsule; and/or (4) a $C_{max}$ of 1-(3-tert-butyl-1-p-tolyl-1H-pyrazol-5-yl)-3-(5-fluoro-2-(1-(2-hydroxyethyl)-1H-indazol-5-yloxy)benzyl)urea when assayed in the plasma of a human subject following oral administration of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B that is greater than the $C_{max}$ for amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea orally administered at the same dosage as a powder in capsule; and/or (5) an $AUC_{inf}$ of 1-(3-tert-butyl-1-p-tolyl-1H-pyrazol-5-yl)-3-(5-fluoro-2-(1-(2-hydroxyethyl)-1H-indazol-5-yloxy)benzyl)urea when assayed in the plasma of a human subject following oral administration of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B that is greater than the $AUC_{inf}$ for amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea, orally administered at the same dosage as a powder in capsule.

In one embodiment, provided herein is a pharmaceutical composition comprising about 213 mg of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B, wherein said composition comprises about 20-50% w/w of said Form B suspended in a carrier matrix comprising Labrafac® Lipophile WL 1349 and Vitamin E TPGS in a ratio selected from 10:90, 15:85, 30:70 and 33:67, wherein a single dose of the pharmaceutical composition when orally administered to a healthy human subject in the fasted state has less variability in $C_{max}$ relative to a single dose of amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea when orally administered to a healthy human subject as a powder in capsule in the fasted state, wherein a single dose of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B is about 426 mg (which is equivalent to 400 mg of the freebase form), and a single dose of amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea is about 400 mg. In one embodiment, the composition is administered as two unit dosages. In one embodiment, the composition comprises Labrafac® Lipophile WL 1349 and Vitamin E TPGS in a ratio of 15:85. In one embodiment, the composition comprises about 20-40% w/w of said Form B. In one embodiment, the composition comprises about 25% w/w of said Form B. In one embodiment, the composition further comprises about 0.1% w/w of an antioxidant. In one embodiment, the antioxidant is BHT. In one embodiment, said Form B is micronized.

As an example, reduction in $C_{max}$ variability is demonstrated in Example 10 (Table 13), which shows that the geometric mean coefficient of variation (CV) for the $C_{max}$ after administration of a novel formulation comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B was 31.1%, whereas the geometric mean CV for the $C_{max}$ after administration of amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea as a powder in capsule was 49.6%.

In one embodiment, provided herein is a pharmaceutical composition comprising about 213 mg of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B, wherein said composition comprises about 20-50% w/w of said Form B suspended in a carrier matrix comprising Labrafac® Lipophile WL 1349 and Vitamin E TPGS in a ratio selected from 10:90, 15:85, 30:70 and 33:67, wherein a single dose of the pharmaceutical composition when orally administered to a healthy human subject in the fasted state has less variability in $AUC_{inf}$ relative to a single dose of amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea when orally administered to a healthy human subject as a powder in capsule in the fasted state, wherein a single dose of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B is about 426 mg (which is equivalent to 400 mg of the freebase form), and a single dose of amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea is about 400 mg. In one embodiment, the composition comprises Labrafac® Lipophile WL 1349 and Vitamin E TPGS in a ratio of 15:85. In one embodiment, the composition comprises about 20-40% w/w of said Form B. In one embodiment, the composition comprises about 25% w/w of said Form B. In one embodiment, the composition further comprises about 0.1% w/w of an antioxidant. In one embodiment, the antioxidant is BHT. In one embodiment, said Form B is micronized.

As an example, reduction in $AUC_{inf}$ variability is demonstrated in Example 10 (Table 13), which shows that the geometric mean coefficient of variation (CV) for the $AUC_{inf}$ after administration of a novel formulation comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B was 37.2%, whereas the mean CV for the $AUC_{inf}$ after administration of amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea as a powder in capsule was 71.9%.

In one embodiment, provided herein is a pharmaceutical composition comprising about 213 mg of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B, wherein said composition comprises about 20-50% w/w of said Form B suspended in a carrier matrix comprising Labrafac® Lipophile WL 1349 and Vitamin E TPGS in a ratio selected from 10:90, 15:85, 30:70 and 33:67, wherein a single dose of the pharmaceutical composition when orally administered to a healthy human subject in the fasted state has less variability in $T_{max}$ relative to a single dose of amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea when orally administered to a healthy human subject as a powder in capsule in the fasted state, wherein a single dose of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B is about 426 mg (which is equivalent to 400 mg of the freebase form), and a single dose of amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea is about 400 mg. In one embodiment, the composition comprises Labrafac® Lipophile WL 1349 and Vitamin E TPGS in a ratio of 15:85. In one embodiment, the composition comprises about 20-40% w/w of said Form B. In one embodiment, the composition comprises about 25% w/w of said Form B. In one embodiment, the composition further comprises about 0.1% w/w of an antioxidant. In one embodiment, the antioxidant is BHT. In one embodiment, said Form B is micronized.

As an example, reduction in $T_{max}$ variability is demonstrated in Example 10 (Table 13), which shows that the range in $T_{max}$ after administration of a novel formulation comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B was about 1 to 3 hours, whereas the range in $T_{max}$ after administration of amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea as a powder in capsule was about 2 to 12 hours.

In one embodiment, provided herein is a pharmaceutical composition comprising about 213 mg of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B, wherein said composition comprises about 20-50% w/w of said Form B suspended in a carrier matrix comprising Labrafac® Lipophile WL 1349 and Vitamin E TPGS in a ratio selected from 10:90, 15:85, 30:70 and 33:67, wherein a single dose of the pharmaceutical composition when orally administered to a healthy human subject in the fasted state has increased exposure (AUC and $C_{max}$) and increased relative bioavailability compared to a single dose of amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea when orally administered to a healthy human subject as a powder in capsule in the fasted state, wherein a single dose of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B is about 426 mg (which is equivalent to 400 mg of the freebase form), and a single dose of amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea is about 400 mg. In one embodiment, the composition is administered as two unit dosages. In one embodiment, the composition comprises Labrafac® Lipophile WL 1349 and Vitamin E TPGS in a ratio of 15:85. In one embodiment, the composition comprises about 20-40% w/w of said Form B. In one embodiment, the composition comprises about 25% w/w of said Form B. In one embodiment, the composition further comprises about 0.1% w/w of an antioxidant. In one embodiment, the antioxidant is BHT. In one embodiment, said Form B is micronized.

As an example, increased exposure and relative bioavailability for a novel composition comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B is demonstrated in Example 10 (Tables 13 and 14), where said composition provided an $AUC_{inf}$ that was about 4-fold greater than the $AUC_{inf}$ for the powder in capsule formulation of amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea.

As a further example, increased exposure and relative bioavailability for a novel composition comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B is demonstrated in Example 10 (Tables 13 and 14), where said composition provided a $C_{max}$ that was about 8-fold greater than the $C_{max}$ for the powder in capsule formulation of amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea.

In one embodiment, provided herein is a pharmaceutical composition comprising about 213 mg of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B, wherein said composition comprises about 20-50% w/w of said Form B suspended in a carrier matrix comprising Labrafac® Lipophile WL 1349 and Vitamin E TPGS in a ratio selected from 10:90, 15:85, 30:70 and 33:67, wherein a single dose of the pharmaceutical composition provides a $C_{max}$ that is about 3000 ng/mL when orally administered to a healthy human subject in the fasted state, wherein a single dose comprises about 426 mg of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B. In one embodiment, the composition is administered as two unit dosages. In one embodiment, the carrier matrix comprises Labrafac® Lipophile WL 1349 and Vitamin E TPGS in a ratio of 15:85. In one embodiment, the composition comprises about 20-40% w/w of said Form B. In one embodiment, the composition comprises about 25% w/w of said Form B. In one embodiment, the composition further comprises about 0.1% w/w of an antioxidant. In one embodiment, the antioxidant is BHT. In one embodiment, said Form B is micronized.

In one embodiment, provided herein is a pharmaceutical composition comprising about 213 mg of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B, wherein said composition comprises about 20-50% w/w of said Form B suspended in a carrier matrix comprising Labrafac® Lipophile WL 1349 and Vitamin E TPGS in a ratio selected from 10:90, 15:85, 30:70 and 33:67, wherein a single dose of the pharmaceutical composition provides an $AUC_{0-inf}$ that is about 15,000 ng·hr/mL when orally administered to a healthy human subject in the fasted state, wherein a single dose comprises about 426 mg of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B. In one embodiment, the composition is administered as two unit dosages. In one embodiment, the carrier matrix comprises Labrafac® Lipophile WL 1349 and Vitamin E TPGS in a ratio of 15:85. In one embodiment, the composition comprises about 20-40% w/w of said Form B. In one embodiment, the composition comprises about 25% w/w of said Form B. In one embodiment, the composition further comprises about 0.1% w/w of an antioxidant. In one embodiment, the antioxidant is BHT. In one embodiment, said Form B is micronized.

In one embodiment, provided herein is a pharmaceutical composition comprising about 213 mg of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B, wherein said composition comprises about 20-50% w/w of said Form B suspended in a carrier matrix comprising Labrafac® Lipophile WL 1349 and Vitamin E TPGS in a ratio selected from 10:90, 15:85 30:70, and 33:67, wherein a single dose of the pharmaceutical composition provides a $T_{max}$ of about 2 hours when orally administered to a healthy human subject in the fasted state, wherein a single dose comprises about 426 mg of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B. In one embodiment, the composition is administered as two unit dosages. In one embodiment, the carrier matrix comprises Labrafac® Lipophile WL 1349 and Vitamin E TPGS in a ratio of 15:85. In one embodiment, the composition comprises about 20-40% w/w of said Form B. In one embodiment, the composition comprises about 25% w/w of said Form B. In one embodiment, the composition further comprises about 0.1% w/w of an antioxidant. In one embodiment, the antioxidant is BHT. In one embodiment, said Form B is micronized.

In one embodiment, provided herein is a pharmaceutical composition comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in an aqueous media, wherein a single dose of the pharmaceutical composition provides a $C_{max}$ that is about 1040 ng/mL when orally administered to a healthy human subject in the fasted state, wherein a single dose is equivalent to a about 426 mg of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B. In one embodiment, said Form B is micronized.

As used herein, the phrase "aqueous media" refers to a carrier that provides a well-dispersed and wetted polymorph but does not contain any excipients that are used to solubilize the compound. The aqueous media can be buffered or unbuffered.

In one embodiment, provided herein is a pharmaceutical composition comprising 213 mg of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in an aqueous media, wherein a single dose of the pharmaceutical composition provides a $AUC_{inf}$ that is about 9460 ng/mL when orally administered to a healthy human subject in the fasted state, wherein a single dose comprises 426 mg of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B.

Also provided herein is a method of administering 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B to a healthy human subject such that the bioavailability of 1-(3-tert-butyl-1-p-tolyl-1H-pyrazol-5-yl)-3-(5-fluoro-2-(1-(2-hydroxyethyl)-1H-indazol-5-yloxy)benzyl)urea is increased, said method comprising orally administering said composition to said subject that comprises about 20 to 50% w/w of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B which is suspended in a carrier matrix comprising Labrafac® Lipophile WL 1349 and Vitamin E TPGS in a ratio selected from 10:90, 15:85, 30:70 and 33:67. In one embodiment, the composition contacts the biological fluids of the gastro-intestinal tract and dissolves said 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B, thereby increasing the bioavailability of 1-(3-tert-butyl-1-p-tolyl-1H-pyrazol-5-yl)-3-(5-fluoro-2-(1-(2-hydroxyethyl)-1H-indazol-5-yloxy)benzyl)urea. In one embodiment, the carrier matrix comprises Labrafac® Lipophile WL 1349 and Vitamin E TPGS in a ratio of 15:85. In one embodiment, the composition comprises about 20-40% w/w of said Form B. In one embodiment, the composition comprises about 25% w/w of said Form B. In one embodiment, the composition further comprises about 0.1% w/w of an antioxidant. In one embodiment, the antioxidant is BHT. In one embodiment, said Form B is micronized.

Food Effect

It is known that food can impact the bioavailability of orally administered drugs, that is, the pharmacokinetic profile of a drug administered to a mammal in the fed state can differ from the pharmacokinetic profile of a drug administered to a mammal in the fasted state. Accordingly, it is desirable to formulate a drug such that the drug can be administered in either the fed or fasted state.

Benefits of a dosage form or composition which substantially eliminates the effect of food include an increase in subject convenience, thereby increasing subject compliance, as the subject does not need to ensure that they are taking a dose either with or without food. This is significant, as with poor subject compliance an increase in the medical condition for which the drug is being prescribed may be observed. In addition, the variability in pharmacokinetic properties can be reduced or minimized.

It was further discovered that pharmacokinetic profiles were consistent for healthy human subject following oral administration in either the fed or fasted state with a single dose of a pharmaceutical composition to said subject, said composition comprising 1-50% w/w of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix, said carrier matrix comprising Labrafac® Lipophile WL 1349 and Vitamin E TPGS in a ratio selected from 10:90, 15:85, 30:70 and 33:67. That is, no clinically significant food effect was observed for this composition. In one embodiment, the ratio of Labrafac® Lipophile WL 1349 to Vitamin E TPGS is 15:85. In one embodiment, the composition comprises about 20-40% w/w of said Form B. In one embodiment, the composition comprises about 25% w/w of said Form B. In one embodiment, the composition further comprises about 0.1% w/w of said antioxidant. In one embodiment, the antioxidant is BHT. In one embodiment, said Form B is micronized.

Methods of Treatment with Pharmaceutical Compositions of the Invention

Also provided are methods of treating a disease or condition by administering the pharmaceutical composition described herein. In one embodiment, a human patient is treated with a pharmaceutical composition described herein in an amount to detectably inhibit p38 kinase activity.

In one embodiment, provided herein is a method of treating a proliferative disorder in a mammal in need of such treatment, wherein the process comprises administering to said mammal a pharmaceutical composition described herein.

Proliferative diseases which may be treated include, but are not limited to, myelodysplastic syndromes, acute myelogenous leukemia, chronic myelogenous leukemia, metastatic melanoma, Kaposi's sarcoma, multiple myeloma, astrocytoma, bone cancer, brain cancer, breast cancer, colorectal cancer, gastric cancer, glioma, glioblastoma, multiforme, head and neck cancer, hematological cancer, hematopoiesis disorders, interstitial lung diseases, lymphocytic leukemia, melanoma, myeloid leukemia, non-small cell lung cancer, ovarian cancer, prostate cancer, sarcoma, skin cancer, small cell lung cancer, and stomach cancer. Other patients which can be treated include those undergoing bone marrow transplantation.

In certain embodiments, the proliferative disease is a myelodysplastic syndrome. The myelodysplastic syndromes (MDS) comprise a heterogeneous group of malignant stem cell disorders characterized by dysplastic and ineffective blood cell production and a variable risk of transformation to acute leukemia. The myelodysplastic syndromes include all disorders of the stem cell in the bone marrow.

Accordingly, provided herein is a method of treating a proliferative disorder in a mammal in need of such treatment, wherein the process comprises administering to said mammal a pharmaceutical composition described herein. In one embodiment, a method for treating a proliferative disorder comprises administering to a mammal in need thereof a therapeutically effective amount of a pharmaceutical composition comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix comprising a surfactant and an oil. In one embodiment, the surfactant is a non-ionic surfactant. In one embodiment, the surfactant is Vitamin E TPGS. In one embodiment, the oil is a long chain or medium chain triglyceride. In one embodiment, the oil is Labrafac® Lipophile WL 1349. In one embodiment, the carrier matrix comprises the oil to surfactant in a ratio of 15:85. In one embodiment, said Form B is present in an amount in the range of 20-50% w/w. In one embodiment, the pharmaceutical composition comprises less than or equal to 1279 mg of said Form B. In one embodiment, the pharmaceutical composition comprises less than or equal to 1066 mg of said Form B. In one embodiment, the pharmaceutical composition comprises less than or equal to 853 mg of said Form B. In one embodiment, the pharmaceutical composition comprises less than or equal to 640 mg of said Form B. In one embodiment, the pharmaceutical composition comprises less than or equal to 213 mg of said Form B. In one embodiment, the pharmaceutical composition comprises less than or equal to 53 mg of said Form B. In one embodiment, the composition comprises about 25% w/w of said Form B. In one embodiment, the proliferative disorder is a myelodysplastic syndrome. In one embodiment, the composition is formulated for once daily oral dosing. In one embodiment, the composition is formulated for twice daily oral dosing.

In another embodiment, the pharmaceutical compositions described herein may be useful for treating a disease or disorder in a mammal in need thereof, wherein the disease or disorder is selected from inflammatory diseases, autoimmune diseases, destructive bone disorders, fibrotic diseases, infectious diseases, viral diseases, degenerative conditions or diseases, wherein the process comprises administering to said mammal a pharmaceutical composition described herein.

Inflammatory diseases which may be treated with the pharmaceutical compositions described herein include, but are not limited to, acute pancreatitis, chronic pancreatitis, asthma, allergies, and adult respiratory distress syndrome.

Autoimmune diseases which may be treated include, but are not limited to, glomeralonephritis, rheumatoid arthritis, systemic lupus erythematosus, scleroderma, chronic thyroiditis, Graves' disease, autoimmune gastritis, insulin-dependent diabetes mellitus (Type I), autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, or graft vs. host disease.

Destructive bone disorders which may be treated include, but are not limited to, osteoporosis, osteoarthritis and multiple myeloma-related bone disorder.

Fibrotic diseases which may be treated include, but are not limited to, idiopathic pulmonary fibrosis, kidney and liver fibrosis.

Infectious diseases which may be treated include, but are not limited to, sepsis, septic shock, and Shigellosis.

Viral diseases which may be treated include, but are not limited to, acute hepatitis infection (including hepatitis A, hepatitis B and hepatitis C), HIV infection and CMV retinitis.

Degenerative conditions or diseases which may be treated by the pharmaceutical compositions of this invention include, but are not limited to, Alzheimer's disease, Parkinson's disease, cerebral ischemia and other neurodegenerative diseases.

In addition, the pharmaceutical compositions described herein may be useful for inhibiting the expression of inducible pro-inflammatory proteins such as prostaglandin endoperoxide synthase-2 (PGHS-2), also referred to as cyclooxygenase-2 (COX-2). Diseases and disorders which may be treated include edema, analgesia, fever and pain, such as neuromuscular pain, headache, cancer pain, dental pain and arthritis pain.

The conditions and diseases that may be treated by the pharmaceutical compositions of this invention may also be conveniently grouped by the cytokine (e.g., IL-1, TNF, IL-6, IL-8) that is believed to be responsible for the disease.

Thus, an IL-1-mediated disease or condition includes rheumatoid arthritis, osteoarthritis, stroke, endotoxemia and/or toxic shock syndrome, inflammatory reaction induced by endotoxin, inflammatory bowel disease, tuberculosis, atherosclerosis, muscle degeneration, cachexia, psoriatic arthritis, Reiter's syndrome, gout, traumatic arthritis, *rubella* arthritis, acute synovitis, diabetes, pancreatic β-cell disease and Alzheimer's disease.

TNF-mediated diseases or conditions include, but are not limited to, rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, reperfusion injury, graft vs. host reaction, allograft rejections, fever and myalgias due to infection, cachexia secondary to infection, AIDS, ARC or malignancy, keloid formation, scar tissue formation, Crohn's disease, ulcerative colitis or pyresis. TNF-mediated diseases also include viral infections, such as HIV, CMV, influenza and herpes; and veterinary viral infections, such as lentivirus infections, including, but not limited to equine infectious anaemia virus, caprine arthritis virus, visna virus or maedi virus; or retrovirus infections, including feline immunodeficiency virus, bovine immunodeficiency virus, or canine immunodeficiency virus.

IL-8 mediated diseases or conditions include, but are not limited to, diseases characterized by massive neutrophil infiltration, such as psoriasis, inflammatory bowel disease, asthma, cardiac and renal reperfusion injury, adult respiratory distress syndrome, thrombosis and glomerulonephritis.

In addition, the compounds of this infection may be used topically to treat conditions caused or exacerbated by IL-1 or TNF. Such conditions include, but are not limited to, inflamed joints, eczema, psoriasis, inflammatory skin conditions such as sunburn, inflammatory eye conditions such as conjunctivitis, pyresis, pain and other conditions associated with inflammation.

Pharmaceutical compositions described herein may be administered in any convenient administrative form, e.g., tablets, powders, capsules, dispersions, suspensions, syrups, sprays, suppositories, gels, emulsions, patches, etc.

Pharmaceutical compositions described herein may be administered by any convenient route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), ocular, vaginal, intraperitoneal, intrapulmonary and intranasal. If parenteral administration is desired, the compositions will be sterile and in a solution or suspension form suitable for injection or infusion.

Pharmaceutical compositions described herein are typically administered orally. Pharmaceutical compositions described herein for oral administration may be administered as a tablet, caplet, hard or soft gelatin capsule, hydroxypropylmethyl cellulose (HPMC) capsule, pill, granules or a suspension.

Accordingly, further provided is a pharmaceutical composition described herein wherein the composition is formulated for oral administration. In one embodiment, pharmaceutical compositions described herein is formulated as a hard gelatin, soft gelatin or HPMC capsule.

Further provided herein is the use of a pharmaceutical composition described herein, in the manufacture of a medicament for the treatment of a proliferative disorder in a mammal. In one embodiment, a method for treating a myelodysplastic syndrome comprises administering to a mammal in need thereof a therapeutically effective amount of a pharmaceutical composition comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B which is suspended in a carrier matrix comprising a surfactant and an oil. In one embodiment, the surfactant is a non-ionic surfactant. In one embodiment, the surfactant is Vitamin E TPGS. In one embodiment, the oil is a long chain or medium chain triglyceride. In one embodiment, the oil is Labrafac® Lipophile WL 1349. In one embodiment, the pharmaceutical composition comprises less than or equal to 1279 mg of said Form B. In one embodiment, the pharmaceutical composition comprises less than or equal to 1066 mg of said Form B. In one embodiment, the pharmaceutical composition comprises less than or equal to 853 mg of said Form B. In one embodiment, the pharmaceutical composition comprises less than or equal to 640 mg of said Form B. In one embodiment, the pharmaceutical composition comprises less than or equal to 426 mg of said Form B. In one embodiment, the pharmaceutical composition comprises less than or equal to 213 mg of said Form B. In one embodiment, the pharmaceutical composition comprises less than or equal to 53 mg of said Form B. In one embodiment, the composition comprises about 25% w/w of said Form B. In one embodiment, the proliferative disorder is a myelodysplastic syndrome.

Further provided herein is a pharmaceutical composition for use in treating a proliferative disorder in a mammal. In one embodiment, a method for treating a myelodysplastic syndrome comprises administering to a mammal in need thereof a therapeutically effective amount of a pharmaceutical composition comprising 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix comprising a surfactant and an oil. In one embodiment, the surfactant is a non-ionic surfactant. In one embodiment, the surfactant is Vitamin E TPGS. In one embodiment, the oil is a long chain or medium chain triglyceride. In one embodiment, the oil is Labrafac® Lipophile WL 1349. In one embodiment, the pharmaceutical composition comprises less than or equal to 1279 mg of said Form B. In one embodiment, the pharmaceutical composition comprises less than or equal to 1066 mg of said Form B. In one embodiment, the pharmaceutical composition comprises less than or equal to 853 mg of said Form B. In one embodiment, the pharmaceutical composition comprises less than or equal to 640 mg of said Form B. In one embodiment, the pharmaceutical composition comprises less than or equal to 426 mg of said Form B. In one embodiment, the pharmaceutical composition comprises less than or equal to 213 mg of said Form B. In one embodiment, the pharmaceutical composition comprises less than or equal to 53 mg of said Form B. In one embodiment, the proliferative disorder is a myelodysplastic syndrome.

EXAMPLES

For illustrative purposes, the following Examples are included. However, it is to be understood that these Examples do not limit the invention and are only meant to suggest a method of practicing the invention.

XRPD Analysis—General Method

XRPD analyses were conducted using a Rigaku X-Ray diffractometer (model Ultima III) operating with a Cu radiation source at 40 kW, 40 mA. Round standard aluminum sample holders with round zero background, and/or quartz plates were used for sample preparation. The scanning parameters were from a range of about 3-40 degree 2θ (±0.3 degrees) and a continuous scan at a rate of about 2 degrees 2θ/minute. 2θ calibration was performed using a Si standard.

Peak assignment analyses were performed using Materials Data Inc. Jade 7 (Version V5.1.2600) program, which uses a peak search algorithm that is based on the Savitzky-Golay 2nd derivatives combined with the counting statistics of intensity data. The peak search on each crystal form was performed using the following parameters: Parabolic Filter, Peak Threshold=3.0, Intensity Cutoff=0.1%, Background=3/1.0 and Peak Location=Summit.

The Tables and corresponding scans are provided with the following approximate data: 2θ (measured in degrees±0.3 degrees), d (measured in angstroms±0.2 angstroms), background (BG), Height and relative intensity using peak height (H %) in counts per second, Area and relative intensity using peak area (A %) and FWHM. The FWHM of a peak is estimated as FWHM=SF×Area/Height, where SF is a constant related to the profile shape of the peak.

The skilled person is aware that an X-ray powder diffraction pattern may be obtained which has one or more measurement errors depending on measurement conditions (such as equipment, sample preparation or instrument used). In particular, it is generally known that intensities in an X-ray powder diffraction pattern may fluctuate depending on measurement conditions and sample preparation. For example, the skilled person will realize that the relative intensity of peaks can be affected by, for example, grains above 30 microns in size and non-unitary aspect ratios, which may affect analysis of samples. The skilled person will also realize that the position of reflections can be affected by the precise height at which the sample sits in the diffractometer and the zero calibration of the diffractometer. The surface planarity of the sample may also have a small effect. Hence a person skilled in the art will appreciate that the diffraction pattern data presented herein is not to be construed as absolute (for further information see Jenkins, R & Snyder, R. L. 'Introduction to X-Ray Powder Diffractometry' John Wiley & Sons, 1996). Therefore, it shall be understood that the crystalline forms of 1-(3-tert-butyl-1-p-tolyl-1H-pyrazol-5-yl)-3-(5-fluoro-2-(1-(2-hydroxyethyl)-1H-indazol-5-yloxy)benzyl) urea hydrochloride are not limited to the crystals that provide X-ray powder diffraction patterns identical to the X-ray powder diffraction patterns described below and any crystals providing X-ray powder diffraction patterns substantially the same as the X-ray powder diffraction patterns described below fall within the scope of the present invention.

Differential Scanning Calorimetry Analysis—General Method

Differential Scanning Calorimetry (DSC) analysis was conducted on unmicronized 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form A (prepared according to Example 1) using a Q1000 DSC (TA Instruments). Samples typically contained between about 2-10 mg in hermetically sealed aluminum pans fitted with a pin-hole in the lid. Samples were heated under an inert nitrogen atmosphere over the temperature range of 25-300° C., with a heating rate of 10° C./min. A second, empty aluminum pan used as a reference.

The skilled person is aware that a DSC thermogram may be obtained which has one or more measurement errors depending on measurement conditions (such as equipment, sample preparation or instrument used). In particular, it is generally known that onset and/or peak temperatures may fluctuate depending on measurement conditions and sample preparation. Accordingly, it will be understood that the onset and/or peak temperature values of the DSC may vary slightly from one instrument to another, one method to another, from one sample preparation to another, and depending on the purity of the sample, and so the values quoted are not to be construed as absolute. Therefore, it shall be understood that the crystalline forms of 1-(3-tert-butyl-1-p-tolyl-1H-pyrazol-5-yl)-3-(5-fluoro-2-(1-(2-hydroxyethyl)-1H-indazol-5-yloxy)benzyl) urea hydrochloride are not limited to the crystals that provide DSC thermograms identical to the thermograms below and any crystals providing thermograms substantially the same as the thermograms described below fall within the scope of the present invention. As used herein, "substantially the same" when referring to a DSC thermogram means that a crystalline form provides a melt maxima that is within +5° C. of the melt maxima shown in the thermograms referenced below.

Comparative Example 1

Polymorph Screen

An extensive polymorph screen was performed on amorphous 1-(3-tert-butyl-1-p-tolyl-1H-pyrazol-5-yl)-3-(5-fluoro-2-(1-(2-hydroxyethyl)-1H-indazol-5-yloxy)benzyl) urea including, but not limited, to the following techniques: slurrying, evaporation, cooling, vapor diffusion, crash precipitation, milling, sublimation, pH modification, solvent combinations and by crash cooling/crash precipitation techniques. Many of those experiments include kinetically focused techniques, such as crash cooling and crash precipitation, in an attempt to isolate metastable forms of 1-(3-tert-butyl-1-p-tolyl-1H-pyrazol-5-yl)-3-(5-fluoro-2-(1-(2-hydroxyethyl)-1H-indazol-5-yloxy)benzyl)urea. As of the filing date of this application, no crystalline forms of 1-(3-tert-butyl-1-p-tolyl-1H-pyrazol-5-yl)-3-(5-fluoro-2-(1-(2-hydroxyethyl)-1H-indazol-5-yloxy)benzyl)urea had been discovered.

Comparative Example 2

Salt Screen

A salt screen with 1-(3-tert-butyl-1-p-tolyl-1H-pyrazol-5-yl)-3-(5-fluoro-2-(1-(2-hydroxyethyl)-1H-indazol-5-yloxy) benzyl)urea was performed with pharmaceutically accepted salts from multiple solvents. The attempted salt screen included attempts at making salts such as the beyslate, tosylate, esylate (ethanesulfonate), mesylate, phosphate, hydrobromide, hydrochloride, maleate, oxalate, nitrate, and sulfonate and mono-hydrogen sulfonate salts. Multiple solvents were utilized as were a variety of crystallization techniques that included evaporation, crash precipitation, anti-solvent addition, cooling, slurrying, vapor diffusion, and solvent combination techniques. Many of those experiments include kinetically focused techniques, such as crash cooling and crash precipitation, in an attempt to isolate metastable salt forms of 1-(3-tert-butyl-1-p-tolyl-1H-pyrazol-5-yl)-3-(5-fluoro-2-(1-(2-hydroxyethyl)-1H-indazol-5-yloxy)benzyl) urea. From this screen, only the besylate, hydrobromide and hydrochloride salts of 1-(3-tert-butyl-1-p-tolyl-1H-pyrazol-5-yl)-3-(5-fluoro-2-(1-(2-hydroxyethyl)-1H-indazol-5-yloxy)benzyl)urea were isolated.

Example 1-A

Preparation of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form A (Method 1)

Amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea (200 mg, 0.359 mmol, 1.0 equivalent) was added to a round bottom flask that had been flame dried under a nitrogen atmosphere. THF (3.0 mL) was added and the mixture was stirred at ambient temperature until the solids were dissolved. HCl in 1,4-dioxane (4M, 135 µL, 0.54 mmol, 1.5 equivalents) was added dropwise with rapid stirring, and the mixture was stirred overnight at ambient temperature. The solids were isolated by vacuum filtration. The solids were washed with methyl tert-butyl ether (MTBE) and then with ether. The solids were dried under vacuum at 40° C. overnight to yield 150 mg 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form A (0.252 mmol, 70% theoretical yield). Methods used to characterize this material are described in Examples 1-C and 1-D.

Example 1-B

Preparation of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form A (Method 2)

Amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea (4.00 g, 7.19 mmol, 1.0 equivalent) was added to a round bottom flask that had been flame dried under a nitrogen atmosphere. THF (50 mL) was added and the mixture was stirred at ambient temperature until the material was dissolved. HCl (4 M in dioxane; 6.40 mL; 25.6 mmol, 3.6 equivalents) was added dropwise with rapid stirring. The mixture was stirred overnight at ambient temperature. The resulting solids were isolated by vacuum filtration and washed with MTBE and then with ether. The solids were dried under vacuum at 50° C. overnight yielding 3.82 g 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form A (6.45 mmol, 90% theoretical yield). Methods used to characterize this material are described in Examples 1-C and 1-D.

Example 1-C

XRPD analysis of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form A 1-(3-Tert-butyl-1-p-tolyl-1H-pyrazol-5-yl)-3-(5-fluoro-2-(1-(2-hydroxyethyl)-1H-indazol-5-yloxy)benzyl)urea hydrochloride Form A (unmicronized) was analyzed according the general method. The XRPD scan is shown in FIG. 1 and the peak assignments are provided in Table 1.

TABLE 1

| Peak # | 2-Theta | d (Å) | Height | H % | Area | A % | FWHM |
|---|---|---|---|---|---|---|---|
| 1 | 6.2 | 14.2 | 50 | 2.6 | 548 | 3.2 | 0.185 |
| 2 | 6.9 | 12.8 | 1917 | 100.0 | 16983 | 100.0 | 0.151 |
| 3 | 7.8 | 11.4 | 584 | 30.5 | 5500 | 32.4 | 0.16 |
| 4 | 9.5 | 9.3 | 85 | 4.4 | 4159 | 24.5 | 0.833 |
| 5 | 10.0 | 8.9 | 127 | 6.6 | 3466 | 20.4 | 0.464 |
| 6 | 11.3 | 7.8 | 61 | 3.2 | 716 | 4.2 | 0.201 |
| 7 | 11.7 | 7.6 | 79 | 4.1 | 1046 | 6.2 | 0.226 |
| 8 | 12.2 | 7.2 | 160 | 8.3 | 1990 | 11.7 | 0.212 |
| 9 | 12.4 | 7.1 | 249 | 13.0 | 2011 | 11.8 | 0.137 |
| 10 | 13.9 | 6.4 | 560 | 29.2 | 7257 | 42.7 | 0.22 |
| 11 | 14.3 | 6.2 | 354 | 18.5 | 3534 | 20.8 | 0.17 |
| 12 | 15.4 | 5.8 | 371 | 19.4 | 4233 | 24.9 | 0.194 |

TABLE 1-continued

| Peak # | 2-Theta | d (Å) | Height | H % | Area | A % | FWHM |
|---|---|---|---|---|---|---|---|
| 13 | 15.6 | 5.7 | 625 | 32.6 | 5917 | 34.8 | 0.161 |
| 14 | 16.3 | 5.4 | 124 | 6.5 | 1399 | 8.2 | 0.191 |
| 15 | 16.8 | 5.3 | 705 | 36.8 | 8329 | 49.0 | 0.201 |
| 16 | 17.1 | 5.2 | 584 | 30.4 | 6309 | 37.2 | 0.184 |
| 17 | 18.3 | 4.9 | 161 | 8.4 | 1369 | 8.1 | 0.145 |
| 18 | 19.0 | 4.7 | 570 | 29.8 | 7853 | 46.2 | 0.234 |
| 19 | 19.2 | 4.6 | 1074 | 56.0 | 14112 | 83.1 | 0.223 |
| 20 | 19.9 | 4.5 | 571 | 29.8 | 5093 | 30.0 | 0.152 |
| 21 | 20.4 | 4.3 | 429 | 22.4 | 8106 | 47.7 | 0.321 |
| 22 | 21.0 | 4.2 | 354 | 18.5 | 3449 | 20.3 | 0.166 |
| 23 | 21.5 | 4.1 | 191 | 10.0 | 1141 | 6.7 | 0.102 |
| 24 | 22.0 | 4.0 | 832 | 43.4 | 9172 | 54.0 | 0.187 |
| 25 | 22.4 | 4.0 | 1007 | 52.5 | 10224 | 60.2 | 0.173 |
| 26 | 22.8 | 3.9 | 474 | 24.7 | 5298 | 31.2 | 0.19 |
| 27 | 23.3 | 3.8 | 324 | 16.9 | 4123 | 24.3 | 0.216 |
| 28 | 23.6 | 3.8 | 158 | 8.3 | 2291 | 13.5 | 0.246 |
| 29 | 24.5 | 3.6 | 222 | 11.6 | 2427 | 14.3 | 0.186 |
| 30 | 25.1 | 3.5 | 90 | 4.7 | 565 | 3.3 | 0.107 |
| 31 | 25.8 | 3.5 | 327 | 17.1 | 3740 | 22.0 | 0.194 |
| 32 | 26.3 | 3.4 | 463 | 24.1 | 10090 | 59.4 | 0.371 |
| 33 | 26.6 | 3.3 | 551 | 28.8 | 8615 | 50.7 | 0.266 |
| 34 | 27.5 | 3.2 | 73 | 3.8 | 900 | 5.3 | 0.208 |
| 35 | 28.0 | 3.2 | 222 | 11.6 | 4496 | 26.5 | 0.344 |
| 36 | 28.3 | 3.1 | 72 | 3.8 | 523 | 3.1 | 0.123 |
| 37 | 28.8 | 3.1 | 94 | 4.9 | 589 | 3.5 | 0.106 |
| 38 | 29.5 | 3.0 | 57 | 3.0 | 458 | 2.7 | 0.136 |
| 39 | 30.3 | 2.9 | 93 | 4.9 | 851 | 5.0 | 0.155 |
| 40 | 31.1 | 2.9 | 164 | 8.6 | 3818 | 22.5 | 0.395 |
| 41 | 31.6 | 2.8 | 144 | 7.5 | 2834 | 16.7 | 0.335 |
| 42 | 32.3 | 2.8 | 56 | 2.9 | 898 | 5.3 | 0.274 |
| 43 | 32.4 | 2.8 | 65 | 3.4 | 898 | 5.3 | 0.234 |
| 44 | 33.0 | 2.7 | 42 | 2.2 | 799 | 4.7 | 0.322 |
| 45 | 34.5 | 2.6 | 59 | 3.1 | 676 | 4.0 | 0.196 |
| 46 | 35.1 | 2.6 | 49 | 2.6 | 683 | 4.0 | 0.236 |
| 47 | 35.6 | 2.5 | 34 | 1.8 | 417 | 2.5 | 0.211 |
| 48 | 36.4 | 2.5 | 83 | 4.3 | 1167 | 6.9 | 0.24 |
| 49 | 37.0 | 2.4 | 50 | 2.6 | 664 | 3.9 | 0.225 |

Example 1-D

Differential Scanning Calorimetry Analysis of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form A Differential Scanning Calorimetry (DSC) analysis was conducted on unmicronized 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form A using the general method described herein. FIG. 2 shows the DSC analysis of unmicronized 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form A. The results show that 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form A has a melt maxima of about 131° C.

Example 2-A

Preparation of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B (Method 1)

Amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea (2.00 g, 3.59 mmol, 1.0 equivalent) was added to a round bottom flask that had been flame dried under a nitrogen atmosphere. MTBE (400 mL) was added and the mixture was stirred at ambient temperature until 1-(3-tert-butyl-1-p-tolyl-1H-pyrazol-5-yl)-3-(5-fluoro-2-(1-(2-hydroxyethyl)-1H-indazol-5-yloxy)benzyl)urea was dissolved. 4M HCl in 1,4-dioxane (1.35 mL, 5.4 mmol, 1.5 equivalents) was added dropwise with rapid stirring. A precipitate formed immediately upon addition of the 4 M HCl in 1,4-dioxane. The suspension was allowed to stir for 48 hours at ambient temperature. The solids were isolated by vacuum filtration and washed with MTBE and then with ether. The solids were dried under vacuum at 50° C. overnight yielding 1.72 g 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B (2.9 mmol, 80.9% theoretical yield).

Example 2-B

Preparation of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B (Method 2)

A round bottom was charged with 500 mL ethyl acetate and amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea (50.0 g, 89.8 mmol, 1.0 equivalent). After 10 minutes of stirring at ambient temperature a clear solution was obtained. 4 M HCl in 1,4-dioxane (23.6 mL, 94.3 mmol, 1.05 eq.) was added dropwise. A cloudy solution immediately resulted. The thick suspension was allowed to stir overnight at ambient temperature. The solids were isolated by vacuum filtration and washed with two 50 mL aliquots of ethyl acetate. The solids were suspended in 500 mL THF. The suspension was allowed to stir overnight and vacuum filtered. The solids were dried under vacuum at 50° C. overnight yielding 48.2 g 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B (81.4 mmol, 91% theoretical yield). Methods used to characterize this material are described in Examples 2-F and 2-G.

Example 2-C

Preparation of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B (Method 3)

In a glass vial, amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea (50 mg, 0.090 mmol, 1 equivalent) was dissolved in 833 μL of solvent (acetonitrile, isopropyl acetate, ethyl acetate, acetone, isopropyl alcohol or ethanol) at ambient temperature. A single 94.3 μL aliquot of 1 M HCl in acetone (0.094 mmol, 1.05 equivalents) was added to the vial. The vial was shaken for at least 24 hours at ambient temperature and allowed to evaporate. The resulting crystalline solids (birefringent under cross-polarized light microscopy) were dried under vacuum at 50° C. overnight, and the crystalline solids were recovered. The solvents used provided 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B in all cases. Methods of characterizing 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B are described in Examples 2-F and 2-G.

Example 2-D

Preparation of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B (Method 4)

A 2 L flask was charged with 50.0 g (89.8 mmol, 1.00 eq.) of amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea and 500 mL of isopropyl alcohol at ambient temperature. After 20 minutes all solids were dissolved. To the solution was added 7.7 mL of concentrated HCl (94.7 mmol, 1.05 eq.) and the solution was allowed to stir overnight at ambient temperature. Solids formed upon stirring. The resulting slurry was filtered and washed with twice with 100 mL isopropyl alcohol. The solids were dried under vacuum at 50° C. overnight yielding 49.5 g 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B (83.5 mmol, 92.9% theoretical yield). Methods used to characterize this material are described in Examples 2-F and 2-G.

Example 2-E

Preparation of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B (Method 5)

A reactor was charged with 2-(5-(2-(aminomethyl)-4-fluorophenoxy)-1H-indazol-1-yl)ethanol (12.13 kg, 40.27 mol) and phenyl 3-tert-butyl-1-p-tolyl-1H-pyrazol-5-ylcarbamate (14.00 kg, 40.07 mol). The solids were suspended in isopropanol (172.8 kg, 220 L). The suspension was heated from 20° C. to 35° C. and stirred at 35-40° C. for 5 hours to form 1-(3-tert-butyl-1-p-tolyl-1H-pyrazol-5-yl)-3-(5-fluoro-2-(1-(2-hydroxyethyl)-1H-indazol-5-yloxy)benzyl)urea. The solution was cooled to 25° C. and subsequently polish filtered. To the filtered solution of 1-(3-tert-butyl-1-p-tolyl-1H-pyrazol-5-yl)-3-(5-fluoro-2-(1-(2-hydroxyethyl)-1H-indazol-5-yloxy)benzyl)urea in isopropanol was added HCl (4.80 kg of 32% aqueous HCl, 1.05 eq.) through a polish filter at 22-23° C., and the mixture was stirred at 18-23° C. overnight (14 hours). The bulk solution was seeded with 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B by adding 20.0 g 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in 300-400 mL of isopropanol to the bulk solution. The mixture was stirred for 3 days (convenience). Analysis showed complete crystallization, at which time 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride From B was isolated by filtration. The product was washed with isopropanol (64 kg, 81.4 L) added via polish filter in portions and dried under vacuum at 55° C. for about 28 hours to provide 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B (92.3% yield). Methods used to characterize this material are described in Examples 2-F and 2-G. Form B prepared according to this method was anhydrous, as confirmed by single X-ray crystallography.

Example 2-F

XRPD analysis of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B 1-(3-Tert-butyl-1-p-tolyl-1H-pyrazol-5-yl)-3-(5-fluoro-2-(1-(2-hydroxyethyl)-1H-indazol-5-yloxy)benzyl)urea hydrochloride Form B (unmicronized) was analyzed according the general method. The XRPD scan is shown in FIG. 3 and the peak assignments are provided in Table 2.

TABLE 2

| peak # | 2-Theta | d (Å) | BG | Height | H % | Area | A % | FWHM |
|---|---|---|---|---|---|---|---|---|
| 1 | 5.456 | 16.1837 | 121 | 44 | 6.5 | 275 | 4.5 | 0.106 |
| 2 | 9.981 | 8.8553 | 80 | 231 | 34.1 | 3764 | 62.1 | 0.277 |
| 3 | 10.318 | 8.5667 | 83 | 90 | 13.3 | 2345 | 38.7 | 0.443 |
| 4 | 12.341 | 7.1663 | 63 | 410 | 60.7 | 3788 | 62.5 | 0.157 |
| 5 | 13.001 | 6.804 | 66 | 196 | 28.9 | 1417 | 23.4 | 0.123 |
| 6 | 13.62 | 6.4963 | 65 | 65 | 9.6 | 1088 | 17.9 | 0.287 |
| 7 | 14.31 | 6.1842 | 78 | 77 | 11.4 | 397 | 6.6 | 0.087 |
| 8 | 15.372 | 5.7594 | 75 | 55 | 8.1 | 359 | 5.9 | 0.111 |
| 9 | 15.92 | 5.5624 | 76 | 487 | 72.1 | 4631 | 76.4 | 0.162 |
| 10 | 16.242 | 5.4528 | 82 | 73 | 10.8 | 656 | 10.8 | 0.153 |
| 11 | 16.941 | 5.2294 | 69 | 676 | 100 | 6064 | 100 | 0.153 |
| 12 | 17.577 | 5.0416 | 70 | 238 | 35.2 | 1798 | 29.7 | 0.128 |
| 13 | 18.462 | 4.802 | 64 | 191 | 28.3 | 1646 | 27.1 | 0.146 |
| 14 | 18.958 | 4.6772 | 66 | 75 | 11.1 | 898 | 14.8 | 0.203 |
| 15 | 19.418 | 4.5675 | 70 | 75 | 11.2 | 812 | 13.4 | 0.183 |
| 16 | 19.799 | 4.4804 | 69 | 113 | 16.7 | 940 | 15.5 | 0.141 |
| 17 | 20.396 | 4.3507 | 71 | 299 | 44.3 | 2725 | 44.9 | 0.155 |
| 18 | 20.797 | 4.2678 | 73 | 116 | 17.2 | 1086 | 17.9 | 0.159 |
| 19 | 21.358 | 4.1568 | 107 | 195 | 28.8 | 2382 | 39.3 | 0.208 |
| 20 | 21.541 | 4.122 | 85 | 261 | 38.7 | 5035 | 83 | 0.328 |
| 21 | 21.939 | 4.048 | 84 | 378 | 55.9 | 3546 | 58.5 | 0.16 |
| 22 | 22.357 | 3.9734 | 116 | 474 | 70.1 | 3454 | 57 | 0.124 |
| 23 | 22.826 | 3.8927 | 89 | 38 | 5.6 | 281 | 4.6 | 0.126 |
| 24 | 23.359 | 3.8052 | 83 | 408 | 60.4 | 3921 | 64.7 | 0.163 |
| 25 | 23.935 | 3.7148 | 64 | 116 | 17.2 | 895 | 14.8 | 0.131 |
| 26 | 24.601 | 3.6158 | 66 | 184 | 27.3 | 1500 | 24.7 | 0.138 |
| 27 | 25.175 | 3.5346 | 68 | 123 | 18.1 | 952 | 15.7 | 0.132 |
| 28 | 25.921 | 3.4345 | 68 | 491 | 72.6 | 4696 | 77.4 | 0.163 |
| 29 | 26.342 | 3.3805 | 68 | 122 | 18 | 1269 | 20.9 | 0.177 |
| 30 | 27.024 | 3.2968 | 76 | 271 | 40.1 | 2933 | 48.4 | 0.184 |
| 31 | 27.299 | 3.2642 | 83 | 197 | 29.1 | 1831 | 30.2 | 0.158 |
| 32 | 27.857 | 3.2 | 79 | 100 | 14.8 | 2565 | 42.3 | 0.436 |
| 33 | 28.055 | 3.178 | 75 | 56 | 8.3 | 2639 | 43.5 | 0.802 |
| 34 | 28.281 | 3.153 | 70 | 64 | 9.5 | 1360 | 22.4 | 0.361 |
| 35 | 28.581 | 3.1207 | 54 | 132 | 19.6 | 1233 | 20.3 | 0.158 |
| 36 | 29.519 | 3.0236 | 61 | 63 | 9.3 | 1179 | 19.4 | 0.319 |
| 37 | 29.98 | 2.9781 | 68 | 95 | 14.1 | 2392 | 39.4 | 0.428 |
| 38 | 30.703 | 2.9097 | 75 | 93 | 13.7 | 684 | 11.3 | 0.125 |
| 39 | 31.54 | 2.8343 | 69 | 60 | 8.9 | 876 | 14.4 | 0.248 |
| 40 | 32.481 | 2.7543 | 64 | 50 | 7.4 | 539 | 8.9 | 0.182 |
| 41 | 33.247 | 2.6926 | 64 | 38 | 5.6 | 418 | 6.9 | 0.189 |
| 42 | 34.976 | 2.5633 | 79 | 82 | 12.1 | 1913 | 31.6 | 0.396 |
| 43 | 35.36 | 2.5364 | 91 | 61 | 9.1 | 1414 | 23.3 | 0.391 |
| 44 | 35.478 | 2.5282 | 91 | 51 | 7.6 | 1291 | 21.3 | 0.427 |
| 45 | 36.434 | 2.464 | 106 | 50 | 7.4 | 423 | 7 | 0.144 |
| 46 | 37.142 | 2.4187 | 114 | 44 | 6.5 | 225 | 3.7 | 0.087 |
| 47 | 37.617 | 2.3892 | 112 | 70 | 10.4 | 960 | 15.8 | 0.232 |
| 48 | 38.659 | 2.3272 | 115 | 48 | 7.1 | 627 | 10.3 | 0.223 |
| 49 | 38.993 | 2.308 | 121 | 52 | 7.7 | 505 | 8.3 | 0.165 |

Example 2-G

Differential Scanning Calorimetry Analysis of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B Differential Scanning Calorimetry (DSC) analysis was conducted on unmicronized 1-(3-tert-butyl-1H- pyrazol-5-yl)-3-(5-fluoro-2-(1-(2-hydroxyethyl)-1H-indazol-5-yloxy)benzyl)urea hydrochloride Form B using the general method described herein. The results are shown in FIG. 4. The results show that 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B has a melt maxima temperature at about 185° C.

Example 3

Particle size reduction of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B 1-(3-Tert-butyl-1-p-tolyl-1H-pyrazol-5-yl)-3-(5-fluoro-2-(1-(2-hydroxyethyl)-1H-indazol-5-yloxy)benzyl)urea hydrochloride Form B was micronized by the use of a jet mill. The inlet pressures, grind pressures, venturi settings, venturi setting, other mill parameters and feed rate of the crystalline material were adjusted according to methods known in the art to provide a milled crystalline material having a Dv90<10 microns.

Example 4

General Preparation of Formulations

The compositions were prepared by heating the individual excipients (surfactant and/or oil) to a temperature required to ensure all material is fully molten (25-60° C.). Individual excipients were mixed well by shaking, and then the carrier matrix was prepared by weighing into a tared container. The carrier matrix was stirred at a temperature sufficient to maintain said combination in a molten state until a homogeneous matrix was obtained, and then 0.1% w/w of BHT was added. The carrier matrix was stirred at a temperature sufficient to maintain said combination in a molten state until the BHT was dissolved. 1-(3-Tert-butyl-1-p-tolyl-1H-pyrazol-5-yl)-3-(5-fluoro-2-(1-(2-hydroxyethyl)-1H-indazol-5-yloxy)benzyl)urea hydrochloride Form B was gradually added to the molten carrier matrix on a % w/w basis and mechanically stirred into the carrier matrix. The matrix was maintained at a sufficiently high temperature to keep the mixture in a molten state during stirring, which was continued until a visibly homogeneous suspension was obtained. Stirring times varied, and were dependent upon excipient composition and drug load. The molten formulations were transferred into capsules to contain a 100 mg or 200 mg dose, respectively (where the dose strength is provided in terms of the amount of the freebase of the compound contained in the capsule).

Example 5

Dissolution Profiles

This study compared the dissolution profiles for various formulations of unmicronized or micronized 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B relative to amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea formulated as a powder in capsule.

The compositions of the formulations are summarized in Tables 3-8. All composition percentages are provided as weight % relative to the total weight of the formulation. In Tables 4-8, the content of 1-(3-tert-butyl-1-p-tolyl-1H-pyrazol-5-yl)-3-(5-fluoro-2-(1-(2-hydroxyethyl)-1H-indazol-5-yloxy)benzyl)urea is expressed both as weight % of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B (also referred to as "Form B") and as weight % of 1-(3-tert-butyl-1-p-tolyl-1H-pyrazol-5-yl)-3-(5-fluoro-2-(1-(2-hydroxyethyl)-1H-indazol-5-yloxy)benzyl)urea (i.e., "active drug load") relative to the weight of the composition. All references to "Labrafac®" in Tables 5-8 are intended to refer to Labrafac® Lipophile WL 1349. All references to "TPGS" in Tables 5-8 are intended to refer to Vitamin E TPGS.

Table 3 shows the dissolution profile for about 100 mg of amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea, formulated as a powder in size "00" HPMC capsules (n=3). In this study, the dissolution media comprised 0.1 N HCl with 0.1% CTAB.

Table 4 shows the dissolution profiles for various formulations comprising about 107 mg of unmicronized 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B (listed as "Form B" in the table) in size "0" HPMC capsules (n=3) where the formulations had a drug load of about 25% w/w of Form B suspended in a carrier matrix. The carrier matrix for the Formulations A and B in Table 4 comprised a surfactant (Gelucire® 44/14 or Solutol® HS15, respectively). The formulations also included 0.1% w/w of an antioxidant (BHT). In this study, the dissolution media comprised 0.1 N HCl with 0.1% CTAB.

Table 5 shows the dissolution profiles for various formulations comprising about 107 mg of micronized 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B in size "0" HPMC capsules (n=2) where the formulations had a drug load of about 25% w/w Form B suspended in a carrier matrix. The carrier matrix for Formulation C in Table 5 comprised a combination of an oil (Labrafac® Lipophile WL 1349) and a surfactant (Vitamin E TPGS) at a ratio of 67:33. The carrier matrix for Formulations D, E and F in Table 5 comprised a combination of two surfactants selected from Vitamin E TPGS, Labrasol®, Solutol® HS15 and Cremophor® RH40 in the ratios shown. The formulations also included 0.1% w/w of an antioxidant (BHT). In this study, the dissolution media comprised 0.1 N HCl with 0.05% CTAB.

Table 6 shows the dissolution profiles for two formulations of about 213 mg of micronized (Formulation G) or unmicronized (Formulation H) 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B in size "00" hard gelatin capsules (n=3). Both formulations comprised a drug load of about 25% w/w of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix comprising 64.1% w/w of Vitamin E TPGS and 11.3% w/w Labrafac® Lipophile WL 1349, yielding a surfactant:oil ratio of 85:15. The formulations also included 0.10% w/w of an antioxidant (BHT). In this study, the dissolution media comprised 0.1 N HCl with 0.05% CTAB.

Table 7 shows the dissolution profiles for various formulations of about 213 mg of micronized 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B (listed as "Form B" in the table) in size "00" hard gelatin capsules (n=3) where the formulations had a drug load of about 25% w/w of Form B suspended in a carrier matrix. The carrier matrix for Formulation I comprised a surfactant (Vitamin E TPGS), and the carrier matrix for Formulations J and K comprised an oil (Labrafac® Lipophile WL 1349) and a surfactant (Vitamin E TPGS) in the ratios shown. The formulations also included 0.10% w/w of an antioxidant (BHT). In this study, the dissolution media comprised 0.1 N HCl with 0.05% CTAB.

Table 8 shows the dissolution profile for various formulations of about 213 mg of micronized 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B in size "00" hard gelatin capsules (n=3) at various drug loads suspended in a carrier matrix. The carrier matrix comprised an oil (Labrafac® Lipophile WL 1349) and a surfactant (Vitamin E TPGS) at a fixed ratio of 15:85. The drug loads for Formulations L, M, N, O and P were selected from between about 21% to about 37% of Form B. In this study, the dissolution media comprised 0.1 N HCl with 0.05% CTAB.

For each study, the capsules were placed in 900 mL of the dissolution media at pH 1 at 37° C. using spiral wire capsule sinkers. The dissolution mixture containing the capsules was stirred using USP Apparatus II paddles at 75 rpm. At the designated time points, the mixture was passed through a 10 μM filter, and the UV absorbance of the filtrate was measured, using a 313 nm wavelength of detection. The measurements were compared to a standard curve generated with 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B or amorphous free base standard dissolved in equivalent dissolution media or 0.1 M HCl with 0.5% CTAB. The results are shown in Tables 3-8. Dissolution results refer to the percent compound dissolved at the indicated time.

TABLE 3

| | Amorphous Free Base, powder in capsule (PIC) | |
|---|---|---|
| | Average | StDev |
| % dissolved in 20 min. | 19.1 | 7.0 |
| % dissolved in 30 min. | 28.1 | 4.5 |
| % dissolved in 40 min. | 34.4 | 3.7 |
| % dissolved in 60 min. | 43.6 | 3.4 |

TABLE 4

| | | Formulation A Gelucire ® 44/14 | | Formulation B Solutol ® HS15 | |
|---|---|---|---|---|---|
| % Composition (total, w/w) | Active Drug Load | 23.0% | | 23.0% | |
| | Form B | 25.0% | | 25.0% | |
| | Gelucire ® 44/14 | 74.9% | | | |
| | Solutol ® HS15 | | | 74.9% | |
| | BHT | 0.1% | | 0.1% | |
| | | Avg. | StDev | Avg. | StDev |
| Dissolution results | % dissolved in 20 min. | 30.8 | 10.9 | 36.3 | 10.5 |
| | % dissolved in 30 min. | 55.4 | 13.2 | 57.2 | 7.9 |
| | % dissolved in 40 min. | 67.3 | 12.0 | 68.4 | 6.9 |
| | % dissolved in 60 min. | 81.3 | 8.8 | 81.5 | 6.2 |

TABLE 5

| | | Formulation C TPGS:Labrafac ® (67:33) | Formulation D TPGS:Labrasol ® (50:50) | Formulation E TPGS:Cremophor ® (85:15) | Formulation F TPGS:Cremophor ® (50:50) |
|---|---|---|---|---|---|
| % Composition (total, w/w) | Active Drug Load | 23.0% | 23.0% | 23.0% | 23.0% |
| | Form B | 25.0% | 25.0% | 25.0% | 25.0% |
| | Vitamin E TPGS | 50.0% | 37.5% | 63.4% | 37.5% |
| | Labrasol ® | | 37.5% | | |
| | Labrafac ® | 24.6% | | | |
| | Cremophor ® RH40 | | | 11.2% | 37.5% |
| | BHT | 0.1% | 0.1% | 0.1% | 0.1% |
| | | Avg. | Avg. | Avg. | Avg. |
| Dissolution results | % dissolved in 20 min. | 49 | 6 | 50 | 70 |
| | % dissolved in 30 min. | 83 | 14 | 85 | 95 |
| | % dissolved in 40 min. | 93 | 19 | 96 | 98 |
| | % dissolved in 60 min. | 100 | 27 | 100 | 100 |

TABLE 6

| % Composition (total, w/w) | | Formulation G (micronized) | Formulation H (unmicronized) |
|---|---|---|---|
| | Active Drug Load | 23.00% | 23.00% |
| | Unmicronized Form B | 24.52% | |
| | Micronized Form B | | 24.52% |
| | Vitamin E TPGS | 64.07% | 64.07% |
| | Labrafac ® | 11.31% | 11.31% |
| | BHT | 0.10% | 0.10% |

TABLE 6-continued

| | | Formulation G (micronized) | | Formulation H (unmicronized) | |
|---|---|---|---|---|---|
| | | Avg | StDev | Avg | StDev |
| Dissolution Results | % dissolved in 15 min. | 44.3 | 7.6 | 9.2 | 0.9 |
| | % dissolved in 30 min. | 82.6 | 6.3 | 28.6 | 2.5 |
| | % dissolved in 45 min. | 90.3 | 0.7 | 40.4 | 1.2 |
| | % dissolved in 60 min. | 92.6 | 0.4 | 45.5 | 0.4 |

TABLE 7

| | | Formulation I 0:100 Labrafac ®:TPGS | | Formulation J 10:90 Labrafac ®:TPGS | | Formulation K 30:70 Labrafac ®:TPGS | |
|---|---|---|---|---|---|---|---|
| % Composition (total, w/w) | Active Drug Load | 23.00% | | 23.00% | | 23.00% | |
| | Form B | 24.52% | | 24.52% | | 24.52% | |
| | Vitamin E TPGS | 75.38% | | 67.84% | | 52.76% | |
| | Labrafac ® | 0.00% | | 7.54% | | 22.61% | |
| | BHT | 0.10% | | 0.10% | | 0.10% | |
| | | Avg | StDev | Avg | StDev | Avg | StDev |
| Dissolution Results | % dissolved in 15 minutes | 14.6 | 2.1 | 39.1 | 6.9 | 47.8 | 9.7 |
| | % dissolved in 30 minutes | 44.5 | 4.1 | 80.6 | 6.2 | 96.1 | 2.2 |
| | % dissolved in 45 minutes | 68.7 | 5.5 | 88.7 | 1.1 | 102.2 | 0.5 |
| | % dissolved in 60 minutes | 84.1 | 5.6 | 90.9 | 0.8 | 104.0 | 0.3 |

TABLE 8

| | | Formulation L | | Formulation M | | Formulation N | | Formulation O | | Formulation P | |
|---|---|---|---|---|---|---|---|---|---|---|---|
| % Composition (total, w/w) | Active Drug Load | 20.00% | | 23.00% | | 26.00% | | 28.75% | | 34.50% | |
| | Form B | 21.32% | | 24.52% | | 27.72% | | 30.65% | | 36.78% | |
| | Vitamin E TPGS | 66.79% | | 64.07% | | 61.35% | | 58.86% | | 53.65% | |
| | Labrafac ® | 11.79% | | 11.31% | | 10.83% | | 10.39% | | 9.47% | |
| | BHT | 0.10% | | 0.10% | | 0.10% | | 0.10% | | 0.10% | |
| | | Avg | St. Dev. | Avg | St. Dev. | Avg | St. Dev. | Avg | St. Dev. | Avg | St. Dev. |
| Dissolution Results | % dissolved in 15 min. | 43.4 | 1.0 | 50.3 | 4.5 | 41.3 | 5.8 | 41.0 | 11.6 | 49.3 | 10.9 |
| | % dissolved in 30 min. | 88.1 | 0.3 | 87.5 | 1.1 | 79.6 | 3.2 | 77.5 | 5.0 | 74.7 | 4.4 |
| | % dissolved in 45 min. | 93.5 | 0.2 | 91.8 | 0.5 | 86.2 | 0.3 | 84.3 | 0.8 | 80.0 | 0.9 |
| | % dissolved in 60 min. | 95.3 | 0.6 | 93.4 | 0.5 | 88.4 | 0.1 | 86.7 | 0.5 | 82.2 | 0.5 |

Results where the dissolution is greater than 100% are due to method variability.

The solubility of amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea and 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride From B in a dissolution media comprising 0.1% of the surfactant (i.e., CTAB) is approximately double that in 0.05% of the surfactant, so the percent dissolution of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B in all formulations shown in Tables 5-8 would be expected to be increased with the additional surfactant. A lower amount of surfactant was used for the formulations shown in Tables 5-8 in order to provide a more discriminating method by decreasing the solubility of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B in the media. The method is further discriminating for the assays summarized in Tables 6-8, where the tested dose was increased to 213 mg of Form B.

Table 4 shows there is an improvement in dissolution for 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B formulated as a suspension in a non-ionic surfactant over amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea formulated as a powder in capsule (Table 3).

Table 5 shows that a carrier matrix comprising a mixture of Vitamin E TPGS and an oil or an additional surfactant provides a significant improvement in dissolution for 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B over amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea formulated as a powder in capsule, with the exception of the specific combination of 50:50 Vitamin E TPGS and Labrasol®.

The data show the improvement in dissolution rate and percent dissolved is improved with the micronized form versus the unmicronized form (Table 6). In addition, the data show that decreasing the amount of Labrafac® Lipophile WL 1349 from 22.61% to 0% results in a slower dissolution release rate and a lower overall percent dissolved at about 60 minutes (Table 7). In addition, the data show that increasing the drug load from about 21%-37% does not result in significant changes in the dissolution profile as shown (Table 8). Additionally, all of the formulations in Tables 7 and 8 show an improved dissolution profile relative to amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea formulated as a powder in capsule (Table 3).

Example 5A

Dissolution Profiles of Compositions Comprising Release Modifiers

This study compared the dissolution profiles for various formulations of micronized 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B comprising one or more release modifiers.

The compositions of the formulations are summarized in Tables X1-X5. All composition percentages are provided as weight % relative to the total weight of the formulation. In Tables X1-X5, the content of 1-(3-tert-butyl-1-p-tolyl-1H-pyrazol-5-yl)-3-(5-fluoro-2-(1-(2-hydroxyethyl)-1H-indazol-5-yloxy)benzyl)urea is expressed both as weight % of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B (also referred to as "Form B") and as weight % of 1-(3-tert-butyl-1-p-tolyl-1H-pyrazol-5-yl)-3-(5-fluoro-2-(1-(2-hydroxyethyl)-1H-indazol-5-yloxy)benzyl) urea (i.e., "active drug load") relative to the weight of the composition. All references to "Labrafac®" in Tables X1-X5 are intended to refer to Labrafac® Lipophile WL 1349.

The compositions described in each of Tables X1-X5 were prepared by heating the individual excipients (surfactant and/or oil) to a temperature required to ensure all material was fully molten (25-60° C.). Individual excipients (oil and/or surfactant) were mixed well by shaking, and then the carrier matrix was prepared by weighing into a tared container. The carrier matrix was stirred at a temperature sufficient to maintain said combination in a molten state until a homogeneous matrix was obtained, and then 0.1% w/w of BHT was added. The carrier matrix was stirred at a temperature sufficient to maintain said combination in a molten state until the BHT was dissolved, and then the release modifier(s) were added. Stirring was continued at a temperature sufficient to maintain a molten state until a homogenous matrix was obtained. 1-(3-Tert-butyl-1-p-tolyl-1H-pyrazol-5-yl)-3-(5-fluoro-2-(1-(2-hydroxyethyl)-1H-indazol-5-yloxy)benzyl)urea hydrochloride Form B was gradually added to the molten modified release carrier matrix on a % w/w basis and mechanically stirred into the carrier matrix. The matrix was maintained at a sufficiently high temperature to keep the mixture in a molten state during stirring, which was continued until a visibly homogeneous suspension was obtained. Stirring times varied, and were dependent upon excipient properties. The molten formulations were transferred into capsules to contain a 200 mg dose (where the dose strength is provided in terms of the amount of the freebase of the compound contained in the capsule).

Table X1 shows the dissolution profiles for formulations T, U and V comprising about 213 mg of micronized 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B in size "00" hard gelatin capsules (n=4 for formulations T and U; n=3 for formulation V) where the formulations comprised various loads of a release modifier (Vitamin E succinate), and had a drug load of about 25% w/w Form B suspended in a carrier matrix comprising a surfactant (Vitamin E TPGS). The formulations also included 0.1% w/w of an antioxidant (BHT).

Table X2 shows the dissolution profile for formulation W comprising about 213 mg of micronized 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B in size "00" hard gelatin (n=4) where the formulation comprised a release modifier (Compritol 888 ATO), and had a drug load of about 25% w/w Form B suspended in a carrier matrix comprising a surfactant (Vitamin E TPGS). The formulation also included 0.1% w/w of an antioxidant (BHT).

Table X3 shows the dissolution profiles for formulations X, Y and Z comprising about 213 mg of micronized 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B in size "00" hard gelatin (n=4) where the formulations comprised various loads of a release modifier (Methocel K4M), and had a drug load of about 25% w/w Form B suspended in a carrier matrix comprising various loads a surfactant (Vitamin E TPGS). The carrier matrix for formulation Z further comprised an oil ((Labrafac® Lipophile WL 1349). The formulations X, Y and Z also included 0.1% w/w of an antioxidant (BHT).

Table X4 shows the dissolution profile for formulation AA comprising about 213 mg of micronized 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B in size "00" hard gelatin (n=4) where the formulation comprised a release modifier (stearyl alcohol) and had a drug load of about 25% w/w Form B suspended in a carrier matrix comprising a surfactant (Vitamin E TPGS). Formulation AA also included 0.1% w/w of an antioxidant (BHT).

Table X5 shows the dissolution profile for formulation BB comprising about 213 mg of micronized 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B in size "0" capsules (n=4) where the formulation comprised two release modifiers (Methocel K4M and Vitamin E succinate), and had a drug load of about 25% w/w Form B suspended in a carrier matrix comprising a surfactant (Vitamin E TPGS). The formulation also included 0.1% w/w of an antioxidant (BHT).

For each study, the capsules were placed in 900 mL of the dissolution media at pH 1 at 37° C. using spiral wire capsule sinkers. The dissolution mixture containing the capsules was stirred using USP Apparatus II paddles at 75 rpm. At the designated time points, the mixture was passed through a 10 µM filter, and the UV absorbance of the filtrate was measured, using a 313 nm wavelength of detection. The measurements were compared to a standard curve generated with 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B dissolved in 0.1 N HCl with 0.05% CTAB. The results are shown in Tables X1-X5. Dissolution results refer to the percent compound dissolved at the indicated time.

TABLE X1

|  |  | Formulation T | | Formulation U | | Formulation V | |
|---|---|---|---|---|---|---|---|
| % Composition | Active Drug Load | 23.00% | | 23.00% | | 23.00% | |
| (total, w/w) | Form B | 24.52% | | 24.52% | | 24.52% | |
|  | Vitamin E TPGS | 72.38% | | 70.38% | | 65.38% | |
|  | Labrafac ® | 0.00% | | 0.00% | | 0.00% | |
|  | Vitamin E Succinate | 3.00% | | 5.00% | | 10.00% | |
|  | BHT | 0.10% | | 0.10% | | 0.10% | |
|  |  | Avg | St. Dev. | Avg | St. Dev. | Avg | St. Dev. |
| Dissolution Results | % dissolved in 30 min. | 21.4 | 4.0 | 10.3 | 2.0 | 1.2 | 0.2 |
|  | % dissolved in 60 min. | 53.0 | 8.8 | 27.3 | 3.2 | 5.3 | 0.4 |
|  | % dissolved in 2 hr | 83.8 | 4.9 | 57.7 | 5.8 | 14.5 | 0.7 |
|  | % dissolved in 3 hr | 91.5 | 1.3 | 80.6 | 4.1 | 23.5 | 0.8 |
|  | % dissolved in 4 hr | 92.7 | 1.0 | 90.4 | 1.9 | 33.5 | 0.8 |
|  | % dissolved in 12 hr | NT | NT | NT | NT | 78.5 | 2.0 |
|  | % dissolved in 18 hr | NT | NT | NT | NT | 91.9 | 1.9 |

NT = not tested

TABLE X2

|  |  | Formulation W |  |
|---|---|---|---|
| % Composition (total, w/w) | Active Drug Load | 23.00% | |
| | Form B | 24.52% | |
| | Vitamin E TPGS | 65.38% | |
| | Labrafac ® | 0.00% | |
| | Compritol 888 ATO | 10.00% | |
| | BHT | 0.10% | |
| | | Avg | St. Dev. |
| Dissolution Results | % dissolved in 30 min. | 32.7 | 7.9 |
| | % dissolved in 60 min. | 68.4 | 6.9 |
| | % dissolved in 2 hr | 84.8 | 1.9 |
| | % dissolved in 3 hr | 86.6 | 1.1 |
| | % dissolved in 4 hr | 86.6 | 1.0 |
| | % dissolved in 12 hr | NT | NT |
| | % dissolved in 18 hr | NT | NT |

NT = not tested

TABLE X3

|  |  | Formulation X | | Formulation Y | | Formulation Z | |
|---|---|---|---|---|---|---|---|
| % Composition (total, w/w) | Active Drug Load | 23.00% | | 23.00% | | 23.00% | |
| | Form B | 24.52% | | 24.52% | | 24.52% | |
| | Vitamin E TPGS | 68.38% | | 65.38% | | 55.57% | |
| | Labrafac ® | 0.00% | | 0.00% | | 9.81% | |
| | Methocel K4M | 7.00% | | 10.00% | | 10.00% | |
| | BHT | 0.10% | | 0.10% | | 0.10% | |
| | | Avg | St. Dev. | Avg | St. Dev. | Avg | St. Dev. |
| Dissolution Results | % dissolved in 30 min. | 28.6 | 4.1 | 16.3 | 2.9 | 26.0 | 5.0 |
| | % dissolved in 60 min. | 56.2 | 6.6 | 35.0 | 4.7 | 54.0 | 8.5 |
| | % dissolved in 2 hr | 81.4 | 4.9 | 60.4 | 6.1 | 82.6 | 6.8 |
| | % dissolved in 3 hr | 88.3 | 0.9 | 79.2 | 3.4 | 90.1 | 2.8 |
| | % dissolved in 4 hr | 89.2 | 1.1 | 85.8 | 0.6 | 92.4 | 1.5 |
| | % dissolved in 12 hr | NT | NT | NT | NT | NT | NT |
| | % dissolved in 18 hr | NT | NT | NT | NT | NT | NT |

NT = not tested

TABLE X4

|  |  | Formulation AA | |
|---|---|---|---|
| % Composition (total, w/w) | Active Drug Load | 23.00% | |
| | Form B | 24.52% | |
| | Vitamin E TPGS | 60.38% | |
| | Labrafac ® | 0.00% | |
| | Stearyl alcohol | 15.00% | |
| | BHT | 0.10% | |
| | | Avg | St. Dev. |
| Dissolution Results | % dissolved in 30 min. | 16.1 | 1.7 |
| | % dissolved in 60 min. | 39.7 | 2.6 |
| | % dissolved in 2 hr | 70.0 | 3.3 |
| | % dissolved in 3 hr | 85.6 | 2.4 |
| | % dissolved in 4 hr | 90.5 | 1.0 |
| | % dissolved in 12 hr | NT | NT |
| | % dissolved in 18 hr | NT | NT |

NT = not tested

TABLE X5

|  |  | Formulation BB | |
|---|---|---|---|
| % Composition (total, w/w) | Active Drug Load | 23.00% | |
| | Form B | 24.52% | |
| | Vitamin E TPGS | 60.38% | |
| | Labrafac ® | 0.00% | |
| | Methocel K4M | 10.00% | |
| | Vitamin E Succinate | 5.00% | |
| | BHT | 0.10% | |
| | | Avg | St. Dev. |
| Dissolution Results | % dissolved in 30 min. | 4.5 | 0.8 |
| | % dissolved in 60 min. | 13.6 | 1.7 |
| | % dissolved in 2 hr | 31.0 | 2.4 |
| | % dissolved in 3 hr | 46.0 | 3.7 |
| | % dissolved in 4 hr | 59.7 | 4.1 |
| | % dissolved in 18 hr | 88.6 | 1.0 |

Example 6

Stability studies of formulations of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B, and amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea These studies were conducted to compare and track the growth of 3-(tert-butyl)-1-(p-tolyl)-1H-pyrazol-5-amine in formulations of amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea and micronized 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B. Formulation Q was prepared with 100 mg of amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea at 23% active drug load in size 0 hard gelatin capsules. Formulation R was prepared with 107 mg of micronized 1-5-yloxy)benzyl)urea and 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B (which is equivalent to 100 mg of the free base) at 23% active drug load (calculated as the free base) in size 0 hard gelatin capsules. Both formulations Q and R also contained 0.1% BHT, 0.1% propyl gallate, and 1% water (to accelerate degradation). Formulation S was prepared with 213 mg of micronized 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B (equivalent to 200 mg of the free base) at 23% active drug load (calculated as the free base) in size "00" hard gelatin capsules. Formulation S also contained 0.1% BHT. Samples were held at 5° C. until time of testing. The specific compositions of each of the formulations are shown in Table 9.

TABLE 9

| Formulation | Composition |
|---|---|
| Q | 100 mg amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea as a solution at 23% active drug load in 15:85 Labrafac ® Lipophile WL 1349:Vitamin E TPGS with 0.1% BHT, 0.1% propyl gallate and 1% water |
| R | 107 mg 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B as a suspension at 23% active drug load in 15:85 Labrafac ® Lipophile WL 1349:Vitamin E TPGS with 0.1% BHT, 0.1% propyl gallate and 1% water |
| S | 213 mg 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B as a suspension at 23% active drug load in 15:85 Labrafac ® Lipophile WL 1349:Vitamin E TPGS with 0.1% BHT |

Formulations Q and R were stored at 40° C./75% relative humidity (RH) and 25° C./60% (RH) up to 4 weeks (Table 10) and Formulation S was stored at 25° C./60% RH up to one year (Table 11). The amount of 3-(tert-butyl)-1-(p-tolyl)-1H-pyrazol-5-amine present in each formulation sample was measured by HPLC with UV absorbance.

TABLE 10

| Formulation # | Amount of degradant[a] present in starting material, ppm | T = 0 Amount of degradant[a] (ppm) | 25° C. 2 wks Amount of degradant[a] (ppm) | 25° C. 4 wks Amount of degradant[a] (ppm) | 40° C. 2 wks Amount of degradant[a] (ppm) | 40° C. 4 wks Amount of degradant[a] (ppm) |
|---|---|---|---|---|---|---|
| Q | 30 | 75 | 102 | 101 | 131 | 158 |
| R | 21 | 29 | 24 | 26 | 41 | 54 |

[a]3-(tert-butyl)-1-(p-tolyl)-1H-pyrazol-5-amine

TABLE 11

| | Formulation S | | | | |
|---|---|---|---|---|---|
| | Time stored at 25° C./60% RH | | | | |
| | T = 0 | 4 weeks | 13 weeks | 7 months | 1 year |
| Amount of degradant[a] | 40 ppm | 43 ppm | 50 ppm | 73 ppm | 69 ppm |

[a]3-(tert-butyl)-1-(p-tolyl)-1H-pyrazol-5-amine

The change in the amount of degradant at the 7 month and 1 year time points can be attributed to the bounce in the assay. The levels of 3-(tert-butyl)-1-(p-tolyl)-1H-pyrazol-5-amine increased more rapidly for the free base formulation (Formulation Q) than for the HCl salt formulations (Formulations R and S) under accelerated conditions.

Example 6A

Stability studies of formulations of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B comprising one or two release modifiers These studies were conducted to compare and track the growth of 2-(5-(2-(aminomethyl)-4-fluorophenoxy)-1H-indazol-1-yl)ethanol in formulations of micronized 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B comprising one or more release modifiers (formulations V, W, Y, Z, AA and BB). A formulation not comprising a release modifier (formulation I) was used as a control. Formulations I, V, W, Y, Z, AA and BB were prepared as described in Examples 5 and 5A. Formulations I, V, W, Y, Z, AA and BB were stored at 30° C./75% RH for 6 months. The amount of 2-(5-(2-(aminomethyl)-4-fluorophenoxy)-1H-indazol-1-yl)ethanol present in each formulation sample was measured by HPLC with UV absorbance. The results are shown in Table Y1.

TABLE Y1

| | Amount of degradant[b] present in starting material, % area | Amount of degradant[b] present after 6 months stored at 30° C./75% RH |
|---|---|---|
| Formulation I | <0.05% | 0.13% |
| Formulation V | <0.05% | 0.10% |
| Formulation W | 0.11% | 0.19% |
| Formulation Y | <0.05% | 0.16% |
| Formulation Z | 0.06% | 0.17% |
| Formulation AA | <0.05% | 0.14% |
| Formulation BB | <0.05% | 0.11% |

[b]2-(5-(2-(aminomethyl)-4-fluorophenoxy)-1H-indazol-1-yl)ethanol

Example 7

Referential Pharmaceutical Composition (Powder in Capsule)

A powder in capsule (PIC) composition was prepared containing 100 mg of amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea weighed into hard gelatin or HMPC capsules.

Example 8

Preparation of Formulation 1

The contents of a fresh container of Vitamin E TPGS were melted in an incubator oven overnight at 40° C. The following day, a container of Labrafac® Lipophile WL 1349 was shaken and 22.5 g were added to a tared 500 mL glass round bottom flask. The container of melted Vitamin E TPGS was shaken and 127.3 g were transferred to the tared 500 mL containing the Labrafac®. A magnetic stir bar was inserted through a side neck and the flask was immediately placed in a reaction block seated on a magnetic hot plate stirrer, secured with a clamp. A temperature sensor was positioned against the glass a minimum of 2 cm below the surface of the contents of the flask. The temperature controller was set to 50° C. and the stir rate was set to 500 rpm. Powderized 2,6-di-tert-butyl-4-methylphenol (201.15 mg) was added to the flask and the contents were stirred under a constant stream of nitrogen for 15 minutes to achieve a homogeneous solution. Micronized 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B (50.26 g), delumped through an 8" stainless steel 20-mesh screen, was transferred into the flask through a funnel and the stir rate was reduced to about 110 to 150 rpm. A spatula was used to incorporate the powder adhered to the walls and the suspension was stirred continuously at 50° C. under nitrogen for 40 minutes to achieve a smooth, homogeneous suspension. A minimum of 150 size "00" white opaque hard gelatin capsules were separated into halves; the bases were arranged in racks for filling and the caps were stored in a sealed glass jar. The capsule bases were individually filled with 869.6 mg of formulated suspension to provide 200 mg active strength capsules (wherein "active strength" refers to the amount of 1-(3-tert-butyl-1-p-tolyl-1H-pyrazol-5-yl)-3-(5-fluoro-2-(1-(2-hydroxyethyl)-1H-indazol-5-yloxy)benzyl)urea as the freebase form contained in each capsule) using a positive displacement pipette using an experimentally determined volume setting. As the capsule filling process continued, the stir rate was slowly reduced to minimize air incorporated into the suspension and the pipette volume was adjusted as needed to compensate for increasing air content. The capsule contents were left to congeal at ambient temperature for a minimum of 1 hour. The caps were snapped securely to the capsule bases. Each of the individual filled capsule weights were confirmed to be within 5% of the target filled capsule weight; the filled capsules were bulk-packaged in a 300 cc HDPE bottle and stored at 2-8° C. for up to 28 days before dosing.

Example 9

Preparation of Formulation 2

Micronized 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B (437.2 mg) was added to a dosing bottle containing dry SyrSpend® (Gallipot® Product No. 107119; pre-weighed by the manufacturer). The bottle was vortexed on a high setting for 1 minute, then stored at 2-8° C. prior to use. To prepare the suspension, sterile water for irrigation (30 mL) was added to the dosing bottle, and the bottle was recapped and shaken vigorously for at least 2 minutes. An additional 30 mL of sterile water for irrigation was added, and the bottle was recapped and shaken vigorously for at least 60 seconds. The suspension was stored at 15-30° C. up to 6 hours prior to use.

Example 10

Study of Pharmacokinetics, Relative Bioavailability, and Potential Food Effect of Compound 1 Formulations in Healthy Subjects Following Single Oral Doses This study was performed to evaluate the plasma pharmacokinetics (PK), relative bioavailability and potential food effect of single oral doses of micronized 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B administered as two formulations in fasted and fed healthy adult subjects. A powder in capsule (PIC) formulation of amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea was included as a control. Formulations 1 and 2 as well as the control are summarized below.

| | |
|---|---|
| Control capsules | Powder in capsule (PIC): Amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea (dose = four 100 mg capsules) |
| Formulation 1 | 213 mg of micronized 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B (suspended in 15:85 Vitamin E TPGS:Labrafac ® Lipophile WL 1349), and 2,6-di-tert-butyl-4-methylphenol. (dose = two capsules, each having 200 mg drug load calculated as the free base of 1-(3-tert-butyl-1-p-tolyl-1H-pyrazol-5-yl)-3-(5-fluoro-2-(1-(2-hydroxyethyl)-1H-indazol-5-yloxy)benzyl)urea) |
| Formulation 2 | Suspension of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B (micronized) in SyrSpend ® SF Dry and sterile water for irrigation. (dose = 60 mL) |

This study design encompassed 3 parallel treatment cohorts of unique subjects evaluating the two formulations (12 subjects per cohort) and the PIC control (6 subjects) in a fasted or fed state, as shown in Table 12. A crossover food-effect assessment for the two formulations occurred with Groups 1 and 2 within Periods 1 and 2.

TABLE 12

| Cohort | Period | | N | Treatment | Dose | Fed State |
|---|---|---|---|---|---|---|
| 1[a] | 1 | Group 1 | 6 | Formulation 1 | 400 mg | Fasted |
| | | Group 2 | 6 | | 400 mg | Fed |
| | 2 | Group 1 | 6 | Formulation 1 | 400 mg | Fed |
| | | Group 2 | 6 | | 400 mg | Fasted |
| 2[b] | 1 | Group 1 | 6 | Formulation 2 | 400 mg | Fasted |
| | | Group 2 | 6 | | 400 mg | Fed |
| | 2 | Group 1 | 6 | Formulation 2 | 400 mg | Fed |
| | | Group 2 | 6 | | 400 mg | Fasted |
| 3 | — | | 6 | PIC (control) | 400 mg | Fasted |

[a]The same subjects were included in Cohort 1-Periods 1 and 2.
[b]The same subjects were included in Cohort 2-Periods 1 and 2.

For each period, subjects were divided into 2 groups of equal size to evaluate any potential period effects on the food-effect assessment. Subjects fasted for a minimum of 8 hours the night before and 4 hours following dosing for the fasted assessment. Subjects consumed a slightly modified standard high-fat meal 30 minutes before and fasted for 4 hours after dosing for the fed portion of the food-effect assessment. Following a 7-day washout after the initial dose, subjects being dosed with the novel formulations returned to the clinic for the Period 2 single dose in the fasted state or following the consumption of a high-fat meal, as appropriate. Within each cohort and period, all subjects were treated on the same day. The same subjects were utilized for Cohort 1—Periods 1 and 2, and likewise for Cohort 2—Periods 1 and 2.

Criteria for Evaluation

Blood samples for the determination of plasma concentrations of 1-(3-tert-butyl-1-p-tolyl-1H-pyrazol-5-yl)-3-(5-fluoro-2-(1-(2-hydroxyethyl)-1H-indazol-5-yloxy)benzyl)urea were collected at the following time points: before dosing and at 0.5, 1, 2, 3, 4, 6, 8, 12, 16, 24 and 48 hours after dosing on Days 1 (all cohorts) and 8 (Cohort 1 and 2 only). Both days were considered single dose for analysis purposes. Pharmacokinetic parameters calculated included the following:

| | |
|---|---|
| $AUC_{inf}$ | area under the plasma concentration-time curve from time 0 extrapolated to infinity |
| $AUC_{last}$ | area under the plasma concentration-time curve from time 0 to the time of the last quantifiable concentration |
| $C_{max}$ | maximum observed plasma concentration |
| $T_{max}$ | time to maximum observed plasma concentration |
| $C_{max}/C_{trough}$ | ratio of the peak plasma concentration to the trough plasma concentration over 24 hours, where $C_{trough}$ was the minimum concentration measured from time 0 to 24 hours after dosing, not including the predose concentration |
| $t_{1/2}$ | apparent terminal half-life |

Summary of Results

Figure 5:
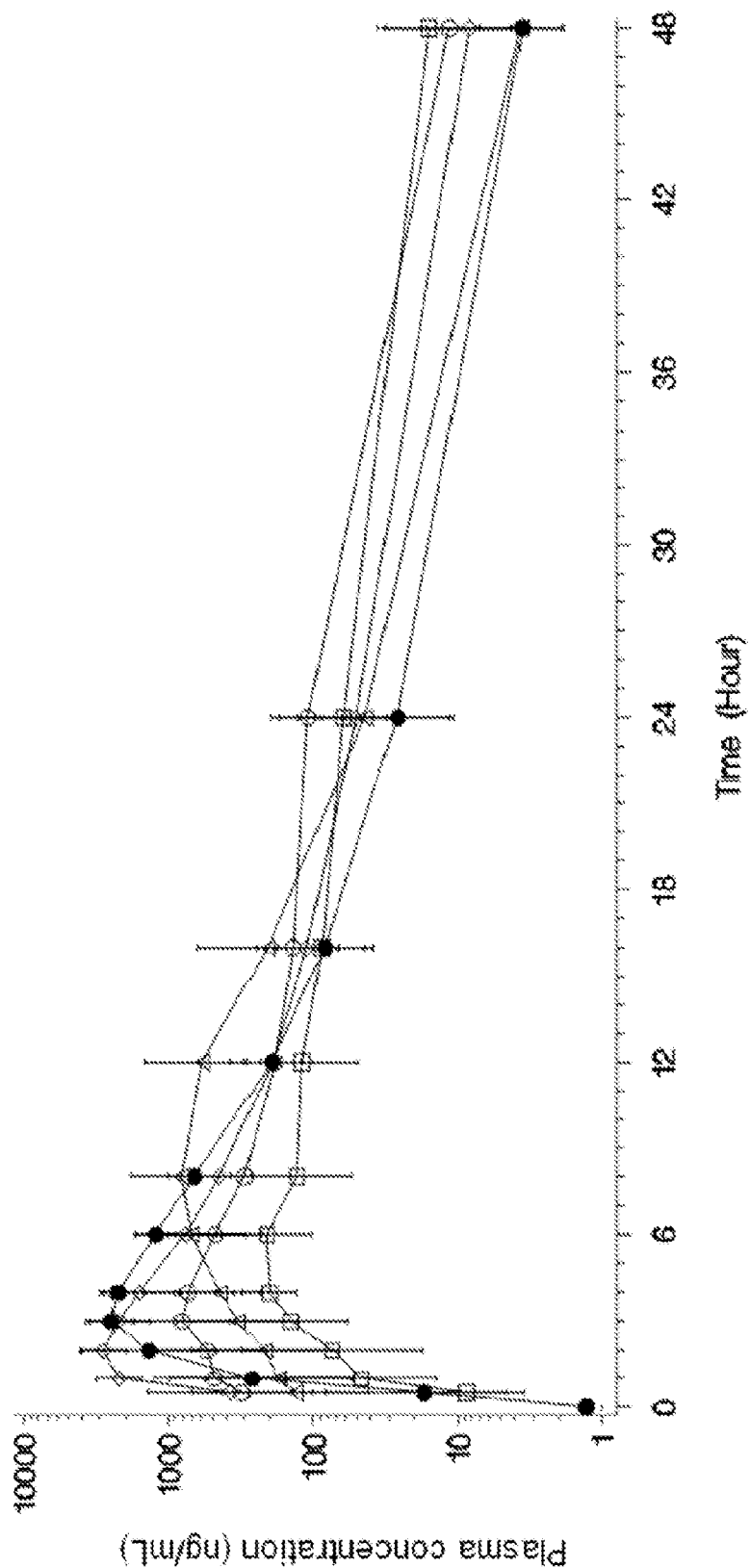
FIG. 5 shows the geometric mean plasma concentration-time profiles of 1-(3-tert-butyl-1-p-tolyl-1H-pyrazol-5-yl)-3-(5-fluoro-2-(1-(2-hydroxyethyl)-1H-indazol-5-yloxy)benzyl)urea for various formulation dosed in the fed and fasted state presented on a semilogarithmic scale as plasma concentration of 1-(3-tert-butyl-1-p-tolyl-1H-pyrazol-5-yl)-3-(5-fluoro-2-(1-(2-hydroxyethyl)-1H-indazol-5-yloxy)benzyl)urea versus time, where the open diamonds represent Formulation 1 dosed in the fasted state, open circles represent Formulation 2 dosed in the fasted state, open squares represent the amorphous PIC dosed in the fasted state, closed circles represent Formulation 1 dosed in the fed state, and open triangles represent Formulation 2 dosed in the fed state.
Figure 6:
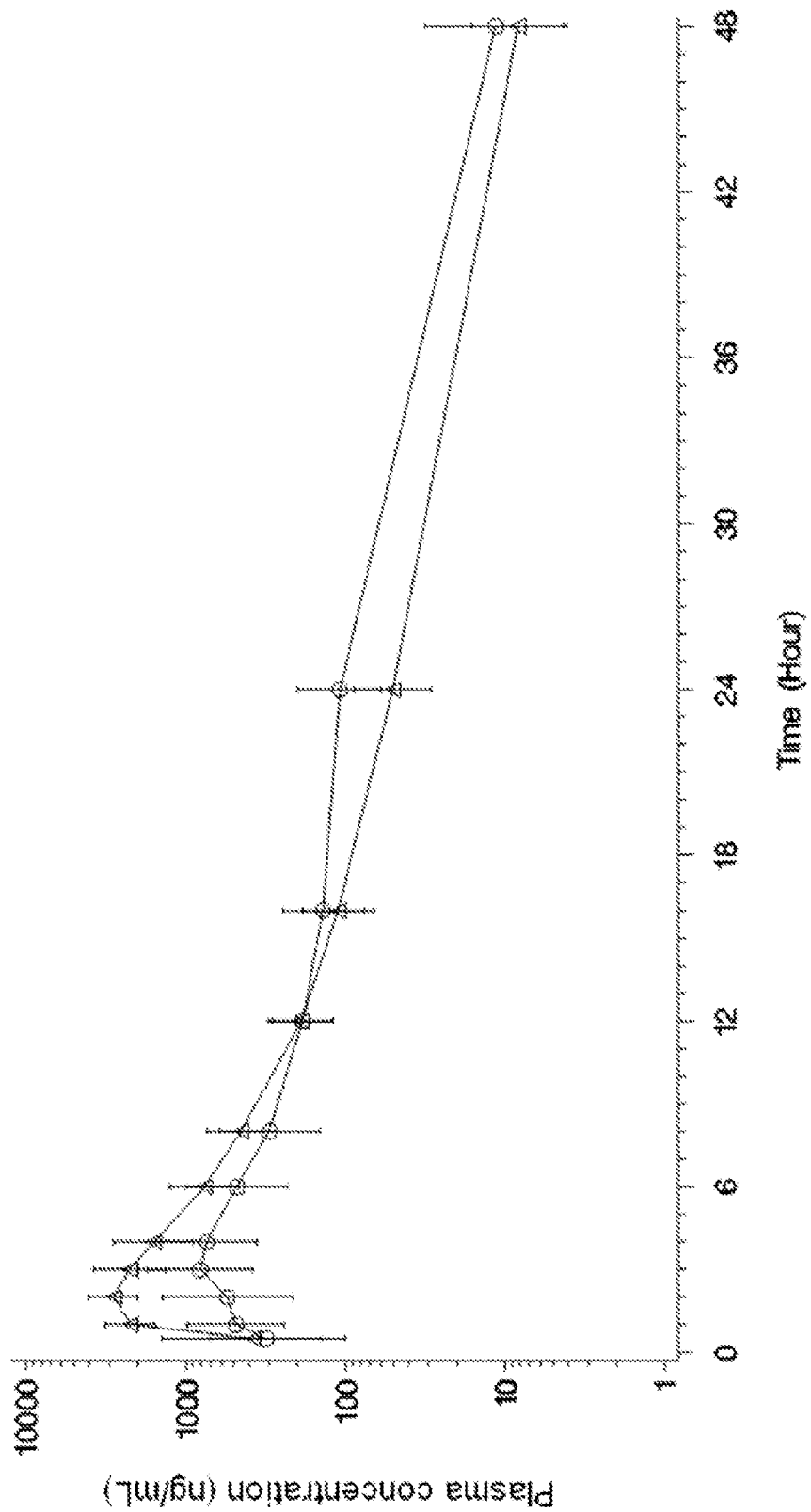
FIG. 6 shows the plasma concentration-time profiles of 1-(3-tert-butyl-1-p-tolyl-1H-pyrazol-5-yl)-3-(5-fluoro-2-(1-(2-hydroxyethyl)-1H-indazol-5-yloxy)benzyl)urea (as the freebase) by treatment formulation in the fasted state presented on a semilogarithmic scale as plasma concentration of 1-(3-tert-butyl-1-p-tolyl-1H-pyrazol-5-yl)-3-(5-fluoro-2-(1-(2-hydroxyethyl)-1H-indazol-5-yloxy)benzyl)urea versus time, where the open triangles represent Formulation 1 and the open circles represent Formulation 2.
Figure 7:
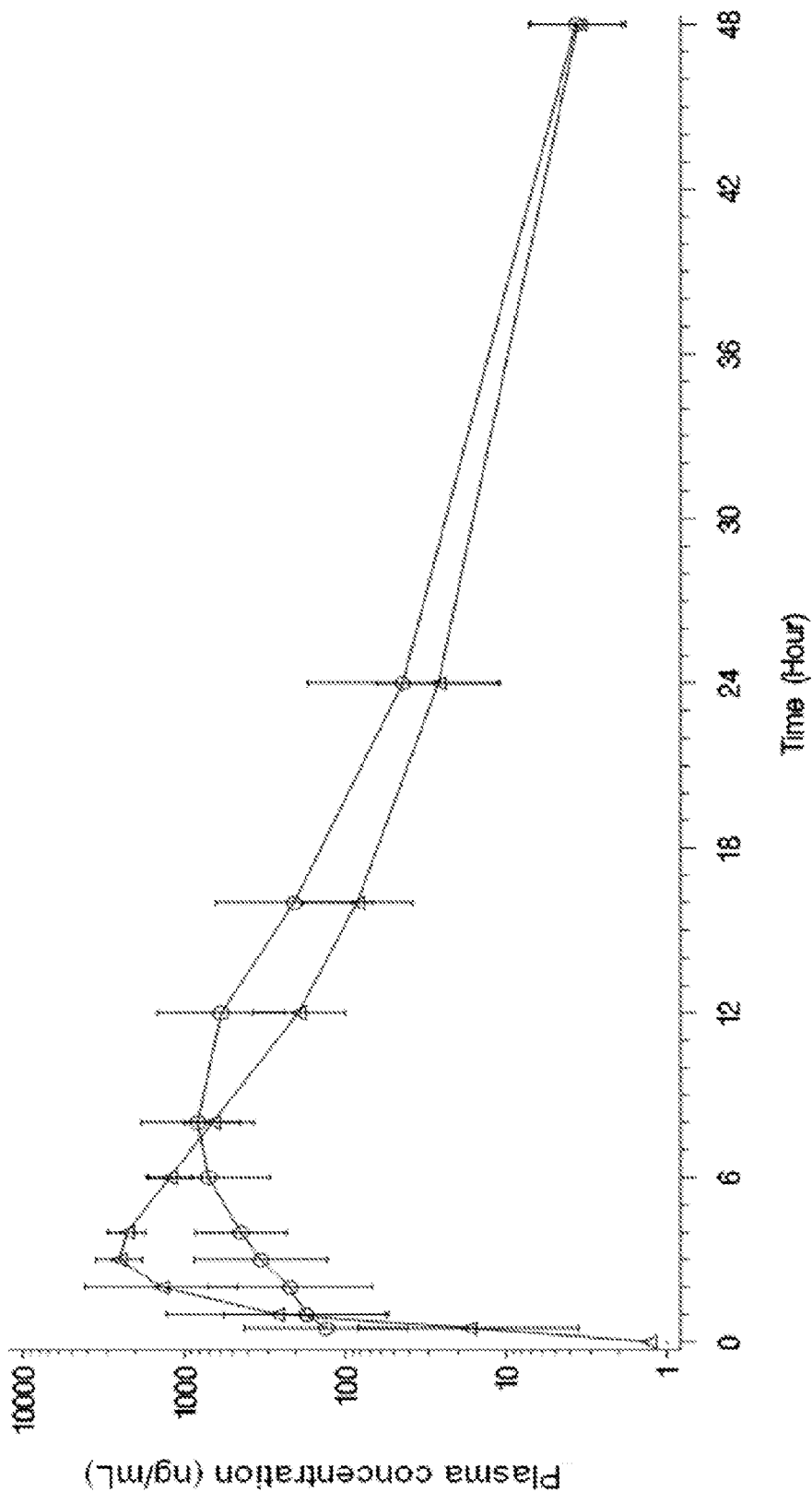
FIG. 7 shows the plasma concentration-time profiles of 1-(3-tert-butyl-1-p-tolyl-1H-pyrazol-5-yl)-3-(5-fluoro-2-(1-(2-hydroxyethyl)-1H-indazol-5-yloxy)benzyl)urea (as the freebase) by treatment formulation in the fed state presented on a semilogarithmic scale as plasma concentration of 1-(3-tert-butyl-1-p-tolyl-1H-pyrazol-5-yl)-3-(5-fluoro-2-(1-(2-hydroxyethyl)-1H-indazol-5-yloxy)benzyl)urea versus time, where the open triangles represent Formulation 1 and the open circles represent Formulation 2.

Geometric mean values and the corresponding CV (coefficient of variation) for the pharmacokinetic parameters of 1-(3-tert-butyl-1-p-tolyl-1H-pyrazol-5-yl)-3-(5-fluoro-2-(1-(2-hydroxyethyl)-1H-indazol-5-yloxy)benzyl)urea after administration of control and the two formulations are shown in Table 13, and geometric mean plasma concentration-time profiles of 1-(3-tert-butyl-1-p-tolyl-1H-pyrazol-5-yl)-3-(5-fluoro-2-(1-(2-hydroxyethyl)-1H-indazol-5-yloxy)benzyl)urea for each treatment formulation are presented on a semi-logarithmic scale in FIG. 5. Geometric mean plasma concentration-time profiles of 1-(3-tert-butyl-1-p-tolyl-1H-pyrazol-5-yl)-3-(5-fluoro-2-(1-(2-hydroxyethyl)-1H-indazol-5-yloxy)benzyl)urea by treatment formulation in the fasted state and fed state on a semilogarithmic scale are presented in FIGS. 6 and 7, respectively.

TABLE 13

Pharmacokinetic Parameters: Geometric Mean (CV)

| Formulation | Cohort | $AUC_{inf}$ (ng·h/mL) | $C_{max}$ (ng/mL) | $T_{max}$[a] (h) | $t_{1/2}$[b] (h) |
|---|---|---|---|---|---|
| Formulation 1, fasted (N = 12) | 1 | 15000 (37.2) | 3010 (31.1) | 2.00 (1.00, 3.00) | 8.50 (28.8) |
| Formulation 1, fed (N = 12) | 1 | 15200 (31.8)[c] | 2880 (30.4) | 3.00 (1.00, 4.00) | 6.53 (9.95)[c] |
| Formulation 2, fasted (N = 12) | 2 | 9460 (46.4)[d] | 1040 (59.6) | 3.00 (1.00, 6.02) | 8.93 (34.7)[d] |
| Formulation 2, fed (N = 11) | 2 | 11400 (39.4)[e] | 1550 (35.1) | 8.00 (3.17, 16.0) | 5.72 (12.5)[e] |
| PIC, fasted (N = 6) | 3 | 4220 (71.9)[f] | 370 (49.6) | 3.50 (2.00, 12.0) | 14.2 (20.5)[f] |

[a]Median (minimum, maximum)
[b]Mean (CV)
[c]n = 11
[d]n = 10
[e]n = 9
[f]n = 5

Table 14 displays the results of the statistical analysis of the relative bioavailability of 1-(3-tert-butyl-1-p-tolyl-1H-pyrazol-5-yl)-3-(5-fluoro-2-(1-(2-hydroxyethyl)-1H-indazol-5-yloxy)benzyl)urea, comparing the AUC and $C_{max}$ of 1-(3-tert-butyl-1-p-tolyl-1H-pyrazol-5-yl)-3-(5-fluoro-2-(1-(2-hydroxyethyl)-1H-indazol-5-yloxy)benzyl)urea after administration of the Formulation 1 or Formulation 2 with the PIC control when the formulations were administered in the fasted state.

TABLE 14

| Formulation | Cohort | $AUC_{inf}$ Ratio | $AUC_{last}$ Ratio | $C_{max}$ Ratio |
|---|---|---|---|---|
| Formulation 1, fasted (N = 12) | 1 | 3.55 (2.38-5.28) | 3.85 (2.63-5.66) | 8.12 (5.76-11.45) |

TABLE 14-continued

| Formulation | Cohort | $AUC_{inf}$ Ratio | $AUC_{last}$ Ratio | $C_{max}$ Ratio |
|---|---|---|---|---|
| Formulation 2, fasted (N = 12) | 2 | 2.28 (1.53-3.42)[a] | 2.26 (1.54-3.31) | 2.80 (1.99-3.95) |

TABLE 14-continued

| Formulation | Cohort | AUC$_{inf}$ Ratio | AUC$_{last}$ Ratio | C$_{max}$ Ratio |
|---|---|---|---|---|
| PIC, fasted (N = 6) | 3 | Reference[b] | Reference | Reference |

Note:
All formulations were given at the same dose (400 mg).
[a]n = 10
[b]n = 5

As shown in Table 14, the relative bioavailability based upon AUC revealed that the AUC's for Formulation 1 and Formulation 2 were 4-fold and 2-fold greater than for the PIC control, respectively, as depicted by the AUC ratios. The ratios of the geometric means and associated 90% CI of AUC$_{inf}$ for 1-(3-tert-butyl-1-p-tolyl-1H-pyrazol-5-yl)-3-(5-fluoro-2-(1-(2-hydroxyethyl)-1H-indazol-5-yloxy)benzyl) urea when administered as Formulation 1 and Formulation 2 versus the PIC control were 3.55 (2.38-5.28) and 2.28 (1.53-3.42), respectively.

More pronounced results were observed for the peak exposures (C$_{max}$) of 1-(3-tert-butyl-1-p-tolyl-1H-pyrazol-5-yl)-3-(5-fluoro-2-(1-(2-hydroxyethyl)-1H-indazol-5-yloxy)benzyl)urea. The statistical analysis results revealed that the C$_{max}$ values for Formulation 1 and Formulation 2 were at least 8-fold and 3-fold greater, with associated 90% CI of (5.76-11.45) and (1.99-3.95) respectively, than the C$_{max}$ of the PIC control.

CONCLUSIONS

Overall, the extent and rate of absorption were different among the 3 different formulations, with Formulation 1 appearing to have a greater rate and extent of absorption than Formulation 2 and the PIC control in the fasted state.

When Formulation 1 was administered in the fed state, 1-(3-tert-butyl-1-p-tolyl-1H-pyrazol-5-yl)-3-(5-fluoro-2-(1-(2-hydroxyethyl)-1H-indazol-5-yloxy)benzyl)urea exposures (AUC and C$_{max}$) decreased less than 5% compared with the fasted state. Therefore, no clinically significant food effect was observed for the Formulation 1. In contrast, after administration of Formulation 2 in the fed state, 1-(3-tert-butyl-1-p-tolyl-1H-pyrazol-5-yl)-3-(5-fluoro-2-(1-(2-hydroxyethyl)-1H-indazol-5-yloxy)benzyl)urea exposures (AUC$_{inf}$, AUC$_{last}$ and C$_{max}$) were greater (25%, 34% and 50%, respectively) than those observed in the fasted state, indicating a possibly clinically relevant food effect for Formulation 2. Median T$_{max}$ values were delayed by 1 hour for Formulation 1 and significantly delayed by 5 hours for Formulation 2 after administration in the fed state.

After administration of Formulation 1, individual concentration-time profiles for 1-(3-tert-butyl-1-p-tolyl-1H-pyrazol-5-yl)-3-(5-fluoro-2-(1-(2-hydroxyethyl)-1H-indazol-5-yloxy)benzyl)urea were similar with respect to exposure, peak exposure, time to peak exposure and apparent elimination for each subject in the fasted and fed states. However, after administration of Formulation 2, individual concentration-time profiles for 1-(3-tert-butyl-1-p-tolyl-1H-pyrazol-5-yl)-3-(5-fluoro-2-(1-(2-hydroxyethyl)-1H-indazol-5-yloxy)benzyl)urea were inconsistent with respect to peak exposure, time to peak exposure and apparent elimination for each subject in the fasted and fed states.

After dose administration, plasma concentrations of 1-(3-tert-butyl-1-p-tolyl-1H-pyrazol-5-yl)-3-(5-fluoro-2-(1-(2-hydroxyethyl)-1H-indazol-5-yloxy)benzyl)urea peaked at median values of 2 to 4 hours for all treatments in the fasted state. In the fed state, the median T$_{max}$ was 3 to 3.5 hours after administration of Formulation 1 and 8 hours after administration of Formulation 2 for 1-(3-tert-butyl-1-p-tolyl-1H-pyrazol-5-yl)-3-(5-fluoro-2-(1-(2-hydroxyethyl)-1H-indazol-5-yloxy)benzyl)urea. In general, mean plasma concentrations of 1-(3-tert-butyl-1-p-tolyl-1H-pyrazol-5-yl)-3-(5-fluoro-2-(1-(2-hydroxyethyl)-1H-indazol-5-yloxy)benzyl)urea decreased to less than 10% of the mean peak plasma concentrations by 48 hours after dosing.

It will be understood that the enumerated embodiments are not intended to limit the invention to those embodiments. On the contrary, the invention is intended to cover all alternatives, modifications and equivalents, which may be included within the scope of the present invention as defined by the claims. Thus, the foregoing description is considered as illustrative only of the principles of the invention.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. A crystalline polymorph of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B.

2. A pharmaceutical composition comprising said 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B according to claim 1.

3. The pharmaceutical composition of claim 2, wherein said 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B is suspended in a carrier matrix, wherein said carrier matrix comprises at least one surfactant.

4. The pharmaceutical composition of claim 3, wherein said carrier matrix further comprises at least one oil.

5. The pharmaceutical composition according to claim 2, comprising about 1 to about 50% w/w of said 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B.

6. The pharmaceutical composition according to claim 2, comprising about 1 to about 40% w/w of said 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B.

7. The pharmaceutical composition according to claim 2, comprising about 1 to about 30% w/w of said 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B.

8. The pharmaceutical composition according to claim 2, comprising about 20 to about 50% w/w of said 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B.

9. The pharmaceutical composition according to claim 2, comprising about 20 to about 40% w/w of said 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B.

10. The pharmaceutical composition according to claim 2, comprising about 25% w/w of said 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B.

11. The pharmaceutical composition according to claim 4, wherein the ratio of the oil to the surfactant is about 10:90.

12. The pharmaceutical composition according to claim 4, wherein the ratio of the oil to the surfactant is about 15:85.

13. The pharmaceutical composition according to claim 4, wherein the ratio of the oil to the surfactant is about 25:75.

14. The pharmaceutical composition according to claim 4, wherein the ratio of the oil to the surfactant is about 33:67.

15. The pharmaceutical composition according to claim 4, wherein the ratio of the oil to the surfactant is about 50:50.

16. The pharmaceutical composition according to claim 4, further comprising one or more release modifiers.

17. The pharmaceutical composition according to claim 16, wherein said release modifier is selected from:
Vitamin E Succinate;
Cellulose derivatives;
Polyvinylpyrrolidones having molecular weights greater than 58,000;
Long chain (C12-C28) triglycerides, long chain (C12-C28) diglycerides, long chain (C12-C28) monoglycerides, and combinations thereof;
Long chain alcohols;
Castor wax;
High molecular weight polyethylene glycols;
Poloxamers; and
Long chain (C12-C28) fatty acids.

18. The pharmaceutical composition according to claim 17, wherein said release modifier is selected from Vitamin E succinate, glyceryl behenate, hydroxypropyl methylcellulose, and stearyl alcohol.

19. The pharmaceutical composition according to claim 18, comprising from at least 0.5% up to 20% by weight of each of said one or more release modifiers.

20. The pharmaceutical composition according to claim 2, wherein said composition comprises about 1 to about 213 mg of said Form B suspended in a carrier matrix, wherein said carrier matrix comprises 0-60% w/w of an oil and 40-100% w/w of a surfactant and said Form B is present in a range from about 1-50% w/w relative to the weight of the composition, wherein said composition has a dissolution profile in a dissolution media in which within 45 minutes about 40-100% of said Form B is dissolved,
wherein said dissolution media comprises a 0.1 M HCl aqueous solution at pH 1 containing about 0.05% cetyl trimethylammonium bromide,
wherein said dissolution is measured by placing said composition in about 900 mL of said dissolution media, optionally using spiral wire capsule sinkers when said formulation is in capsule form, and using a USP II apparatus with a 75 rpm paddle speed.

21. The pharmaceutical composition according to claim 2, wherein said composition comprises about 1 to about 213 mg of said Form B suspended in a carrier matrix, wherein said carrier matrix comprising 0-60% w/w of an oil and 40-100% w/w of a surfactant and said Form B is present in a range from about 1-50% w/w relative to the weight of said composition, wherein said composition has a dissolution profile in a dissolution media in which within 60 minutes about 50-100% of said Form B is dissolved,
wherein said dissolution media comprises a 0.1 M HCl aqueous solution at pH 1 containing about 0.05% cetyl trimethylammonium bromide,
wherein said dissolution is measured by placing said composition in about 900 mL of said dissolution media, optionally using spiral wire capsule sinkers when said formulation is in capsule form, and using a USP II apparatus with a 75 rpm paddle speed.

22. The pharmaceutical composition according to claim 3, wherein said surfactant is a non-ionic surfactant.

23. The pharmaceutical composition according to claim 22, wherein said non-ionic surfactant is selected from D-α-tocopheryl polyethylene glycol 1000 succinate, polyethylene glycol-15-hydroxystearate, polyoxyl 35 castor oil, polyoxyl 40 hydrogenated castor oil, polyethylene glycol sorbitan monostearate, polyoxyethylene 20 sorbitan monooleate, caprylocaproyl polyoxylglycerides, lauroyl polyoxylglycerides, stearoyl polyoxylglycerides, polyethylene glycol hexadecyl ether, polyoxyethylene (20) oleyl ether, polyethylene glycol hexadecyl ether, sorbitan monolaurate, sorbitan monopalmitate, sorbitan monooleate, a synthetic copolymer of ethylene and propylene oxides, a synthetic copolymer of ethylene and propylene oxides, phospholipids, zwitterionic surfactants, soy lecithin, phosphatidyl choline, phosphatidyl inositol, phosphatidyl ethanolamine, and cocamidopropyl betaine, and mixtures thereof.

24. The pharmaceutical composition according to claim 23, wherein said non-ionic surfactant is selected from D-α-tocopheryl polyethylene glycol 1000 succinate, polyethylene glycol-15-hydroxystearate, polyoxyl 40 hydrogenated castor oil, caprylocaproyl polyoxylglycerides, and lauroyl polyoxylglycerides.

25. The pharmaceutical composition according to claim 24, wherein said non-ionic surfactant is D-α-tocopheryl polyethylene glycol 1000 succinate.

26. The pharmaceutical composition according to claim 4, wherein said oil is a medium chain triglyceride.

27. The pharmaceutical composition of claim 26, wherein said medium chain triglyceride is selected from caprylic acid/capric acid triglycerides and medium chain fatty acids.

28. The pharmaceutical composition according to claim 27, wherein said medium chain triglyceride is caprylic acid/capric acid triglyceride.

29. The pharmaceutical composition according to claim 4, wherein said oil is a long chain triglyceride.

30. The pharmaceutical composition of claim 29, wherein the long chain triglyceride is glyceryl behenate.

31. The pharmaceutical composition according to claim 2, wherein said composition comprises about 1 to about 213 mg of said Form B suspended in a carrier matrix, wherein said carrier matrix comprises either D-α-tocopheryl polyethylene glycol 1000 succinate or a mixture of caprylic acid/capric acid triglyceride and D-α-tocopheryl polyethylene glycol 1000 succinate in a ratio selected from 10:90, 15:85, 30:70 and 33:67 and said Form B is present in a range from about 20-40% w/w relative to the weight of said composition, wherein said composition has a dissolution profile in a dissolution media in which within 45 minutes about 70-100% of said Form B is dissolved,
wherein said dissolution media comprises a 0.1 M HCl aqueous solution at pH 1 containing about 0.05% cetyl trimethylammonium bromide,
wherein said dissolution is measured by placing said composition in about 900 mL of said dissolution media, optionally using spiral wire capsule sinkers when said formulation is in capsule form, and using a USP II apparatus with a 75 rpm paddle speed.

32. The pharmaceutical composition according to claim 2, wherein said composition comprises about 1 to about 213 mg of said Form B, wherein said carrier matrix comprises either D-α-tocopheryl polyethylene glycol 1000 succinate or a mixture of caprylic acid/capric acid triglyceride and D-α-tocopheryl polyethylene glycol 1000 succinate in a ratio selected from 10:90, 15:85, 30:70 and 33:67 and wherein said Form B is present in a range from about 20-40% w/w relative to the weight of said composition, wherein said composition has a dissolution profile in a dissolution media in which within 60 minutes about 80-100% of said Form B is dissolved,
wherein said dissolution media comprises a 0.1 M HCl aqueous solution at pH 1 containing about 0.05% cetyl trimethylammonium bromide,
wherein said dissolution is measured by placing said composition in about 900 mL of said dissolution media, optionally using spiral wire capsule sinkers when said formulation is in capsule form, and using a USP II apparatus with a 75 rpm paddle speed.

33. The pharmaceutical composition according to claim 2, wherein said composition comprises 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix, wherein said carrier matrix comprises a medium chain triglyceride and a non-ionic surfactant in a ratio selected from 10:90, 15:85 30:70 and 33:67 and said Form B is present in a range from about 20-50% w/w relative to the weight of said composition, wherein said composition optionally further comprises an antioxidant.

34. The pharmaceutical composition according claim 33, wherein said composition comprises less than or equal to 300 ppm of 3-(tert-butyl)-1-(p-tolyl)-1H-pyrazol-5-amine after storage at 40° C./75% relative humidity for 4 weeks.

35. The pharmaceutical composition according claim 33, wherein said composition comprises less than or equal to 100 ppm of 3-(tert-butyl)-1-(p-tolyl)-1H-pyrazol-5-amine after storage at 40° C./75% relative humidity for 4 weeks.

36. The pharmaceutical composition according claim 33, wherein said composition comprises less than or equal to 55 ppm of 3-(tert-butyl)-1-(p-tolyl)-1H-pyrazol-5-amine after storage at 40° C./75% relative humidity for 4 weeks.

37. The pharmaceutical composition according claim 33, wherein said composition comprises less than or equal to 100 ppm of 3-(tert-butyl)-1-(p-tolyl)-1H-pyrazol-5-amine after storage at 25° C./60% relative humidity for 1 year.

38. The pharmaceutical composition according claim 33, wherein said composition comprises less than or equal to 70 ppm of 3-(tert-butyl)-1-(p-tolyl)-1H-pyrazol-5-amine after storage at 25° C./60% relative humidity for 1 year.

39. The pharmaceutical composition according to claim 33, wherein said medium chain triglyceride is caprylic acid/capric acid triglyceride and said non-surfactant is D-α-tocopheryl polyethylene glycol 1000 succinate.

40. The pharmaceutical composition according to claim 39, wherein the ratio of said caprylic acid/capric acid triglyceride to said D-α-tocopheryl polyethylene glycol 1000 succinate is about 15:85.

41. The pharmaceutical composition according to claim 2, further comprising an anti-oxidant.

42. The pharmaceutical composition of claim 41, wherein said antioxidant is 2,6-di-tert-butyl-4-methylphenol.

43. The pharmaceutical composition according to claim 2, comprising about 213 mg of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix, wherein said carrier matrix comprises caprylic acid/capric acid triglyceride and D-α-tocopheryl polyethylene glycol 1000 succinate in a ratio selected from 10:90, 15:85, 30:70, and 33:67 and said Form B is present in a range from about 20-50% w/w relative to the weight of said composition, wherein said composition optionally further comprises an antioxidant.

44. The pharmaceutical composition according to claim 43, wherein the ratio of said caprylic acid/capric acid triglyceride to said D-α-tocopheryl polyethylene glycol 1000 succinate is about 15:85.

45. The pharmaceutical composition according to claim 43, wherein said composition comprises about 25% w/w of said Form B.

46. The pharmaceutical composition according to claim 45, wherein a single dose of the pharmaceutical composition when orally administered to a healthy human subject in the fasted state has less variability in $C_{max}$ relative to a single dose of amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea when orally administered to a healthy human subject as a powder in capsule in the fasted state, wherein a single dose of said 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B is about 426 mg and a single dose of said amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea is about 400 mg.

47. The pharmaceutical composition according to claim 45, wherein a single dose of the pharmaceutical composition when orally administered to a healthy human subject in the fasted state has less variability in $AUC_{inf}$ relative to a single dose of amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea when orally administered to a healthy human subject as a powder in capsule in the fasted state, wherein a single dose of said 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B is about 426 mg and a single dose of said amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea is about 400 mg.

48. The pharmaceutical composition according to claim 45, wherein a single dose of the pharmaceutical composition when orally administered to a healthy human subject in the fasted state has less variability in $T_{max}$ relative to a single dose of amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea when orally administered to a healthy human subject as a powder in capsule in the fasted state, wherein a single dose of said 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B is about 426 mg and a single dose of said amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea is about 400 mg.

49. The pharmaceutical composition according to claim 45, wherein a single dose of the pharmaceutical composition when orally administered to a healthy human subject in the fasted state has increased exposure and increased relative bioavailability relative to a single dose of amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea when orally administered to a healthy human subject as a powder in capsule in the fasted state, wherein a single dose of said 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B is about 426 mg and a single dose of said amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea is about 400 mg.

50. The pharmaceutical composition of claim 49, wherein said composition provides an $AUC_{inf}$ that is about 4-fold greater than the $AUC_{inf}$ for the powder in capsule formulation of amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea.

51. The pharmaceutical composition of claim 49, wherein said composition provides $C_{max}$ that is about 8-fold greater than the $C_{max}$ for the powder in capsule formulation of amorphous 1-(3-tert-butyl-1-p-tolyl-1H-pyrazol-5-yl)-3-(5-fluoro-2-(1-(2-hydroxyethyl)-1H-indazol-5-yloxy)benzyl) urea.

52. The pharmaceutical composition according to claim 4, prepared by the method comprising:
(i) stirring a mixture of said surfactant and said oil at a temperature sufficient to provide a liquefied homogeneous carrier matrix optionally in a nitrogen atmosphere; and
(ii) adding said 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B to the carrier matrix with stirring at a temperature sufficient to maintain said carrier matrix in a liquefied state and optionally under a nitrogen atmosphere, thereby providing said pharmaceutical composition comprising a liquefied homogeneous suspension of said Form B in said carrier matrix.

53. The pharmaceutical composition according to claim 52, wherein said method further comprises (iv) transferring aliquots of said molten homogenous suspension obtained in step (iii) into capsules and allowing said suspension to cool in said capsules to provide said composition comprising a liquid, solid semi-solid or solid form of the suspension within the capsules.

54. The pharmaceutical composition according to claim 4, prepared by the method comprising (i) homogenizing said oil at a temperature sufficient to melt the oil optionally under a nitrogen atmosphere; (ii) homogenizing said surfactant at a temperature sufficient to melt the surfactant optionally under a nitrogen atmosphere; (iii) combining said molten oil and molten surfactant with stirring at a temperature that maintains the combination in a molten state and optionally under a nitrogen atmosphere to form a molten homogenous carrier matrix; and (iv) adding said 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B to said molten homogenous carrier matrix with stirring at a temperature that maintains said carrier matrix in a molten state and optionally under a nitrogen atmosphere, thereby providing said composition comprising a molten homogeneous suspension of said Form B in said carrier matrix.

55. The pharmaceutical composition according to claim 54, wherein said method further comprises (v) transferring aliquots of said molten homogenous suspension obtained in step (iv) into capsules and allowing said suspension to cool in said capsules to provide said composition comprising a liquid, solid semi-solid or solid form of the suspension within the capsules.

56. The pharmaceutical composition according to claim 4, prepared by the method comprising (i) homogenizing said oil at a temperature sufficient to melt the oil; (ii) homogenizing said surfactant at a temperature sufficient to melt the surfactant; and (iii) combining said molten oil, said molten surfactant, and said 1-(3-tert-butyl-1-p-tolyl-1H-pyrazol-5-yl)-3-(5-fluoro-2-(1-(2-hydroxyethyl)-1H-indazol-5-yloxy) benzyl)urea hydrochloride Form B with stirring at a temperature that maintains said combination in a molten state, thereby providing said composition comprising a molten homogeneous suspension of said Form B in a carrier matrix.

57. The pharmaceutical composition according to claim 56, wherein said method further comprises (iv) transferring aliquots of said molten homogenous suspension obtained in step (iii) into capsules and allowing said suspension to cool in said capsules to provide said composition comprising a liquid, solid semi-solid or solid form of the suspension within the capsules.

58. The pharmaceutical composition according to claim 4, wherein said 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B is micronized.

59. The polymorph according to claim 1, characterized by having at least one specific XRPD diffraction peak (2θ degrees±0.3) at about 15.9.

60. The polymorph according to claim 1, characterized by having XRPD diffraction peaks (2θ degrees±0.3) at about 12.3, 13.0, 15.9, 16.9 and 17.6.

61. The polymorph according to claim 1, characterized by having XRPD diffraction peaks (2θ degrees±0.3) at about 10.0, 12.3, 13.0, 15.9, 16.9, 17.6, 18.5, 23.4, 27.0 and 27.3.

62. The polymorph according to claim 1, characterized by having XRPD diffraction peaks (2θ degrees±0.3) at about 10.0, 12.3, 13.0, 15.9, 16.9, 17.6, 18.5, 20.4, 21.5, 21.9, 22.4, 23.4, 25.9, 27.0 and 27.3.

63. The polymorph according to claim 1, characterized by having XRPD diffraction peaks (2θ degrees±0.3) at about 10.0, 12.3, 13.0, 15.9, 16.9, 17.6, 18.5, 19.8, 20.4, 20.8, 21.5, 21.9, 22.4, 23.4, 23.9, 24.6, 25.2, 25.9, 27.0 and 27.3.

64. The polymorph according to claim 1, characterized by having substantially the same XRPD pattern as shown in FIG. 3.

65. The polymorph according to claim 1, characterized by having an XRPD pattern that substantially includes the peaks in Table 2.

66. The polymorph according to claim 1, wherein 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B is in substantially pure form.

67. The polymorph according to claim 1, characterized by having a DSC thermogram which comprises an endothermic event having a melt maxima temperature at about 185±5° C.

68. A method for treating a myelodysplastic syndrome comprising administering to a patient in need thereof a therapeutically effective amount of a pharmaceutical composition according to claim 2.

69. A method of administering 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B to a healthy human subject such that the bioavailability of 1-(3-tert-butyl-1-p-tolyl-1H-pyrazol-5-yl)-3-(5-fluoro-2-(1-(2-hydroxyethyl)-1H-indazol-5-yloxy)benzyl)urea is increased, said method comprising orally administering a composition comprising about 20 to 50% w/w of said 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B suspended in a carrier matrix, said carrier matrix comprising caprylic acid/capric acid triglyceride and D-α-tocopheryl polyethylene glycol 1000 succinate in a ratio selected from 10:90, 15:85 30:70 and 33:67.

70. The method of claim 69, whereby said composition contacts the biological fluids of the gastro-intestinal tract and dissolves said 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B, thereby increasing the bioavailability of said 1-(3-tert-butyl-1-p-tolyl-1H-pyrazol-5-yl)-3-(5-fluoro-2-(1-(2-hydroxyethyl)-1H-indazol-5-yloxy) benzyl)urea.

71. The method according to claim 69, wherein said composition comprises 25% w/w of said Form B.

72. A process for preparing a pharmaceutical composition of claim 4, comprising:
  (i) stirring a mixture of said surfactant and said oil at a temperature sufficient to provide a liquefied homogeneous carrier matrix, optionally under a stream of nitrogen; and
  (ii) adding said 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B to the carrier matrix with stirring at a temperature sufficient to maintain said carrier matrix in a liquefied state, optionally under a stream of nitrogen, to provide a liquefied homogeneous suspension of said Form B in said carrier matrix.

73. The process of claim 72, further comprising adding an antioxidant in step (i) or step (ii).

74. The process of claim 72, further comprising adding one or more release modifiers in step (ii).

75. A process for preparing a pharmaceutical composition of claim 4, comprising:
  (i) homogenizing said oil at a temperature sufficient to melt the oil, optionally under a stream of nitrogen;
  (ii) homogenizing said surfactant at a temperature sufficient to melt the surfactant, optionally under a stream of nitrogen;
  (iii) combining said molten oil and molten surfactant with stirring at a temperature that maintains the combination in a molten state, optionally under a stream of nitrogen, to form a molten homogenous carrier matrix; and
  (iv) adding 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B to said molten homogenous carrier matrix with stirring at a temperature that maintains said carrier matrix in a molten state, optionally under a stream of nitrogen, to provide a molten homogeneous suspension of said Form B in said carrier matrix.

76. The process of claim 75, further comprising adding an antioxidant in step (iii) or step (iv).

77. The process of claim 75, further comprising adding one or more release modifiers in step (iii) or (iv).

78. A process for preparing a pharmaceutical composition of claim 4, comprising:
  (i) homogenizing said oil at a temperature sufficient to melt the oil, optionally under a stream of nitrogen;
  (ii) homogenizing said surfactant at a temperature sufficient to melt the surfactant, optionally under a stream of nitrogen; and
  (iii) combining said molten oil, said molten surfactant, and 1-(3-tert-butyl-1-p-tolyl-1H-pyrazol-5-yl)-3-(5-fluoro-2-(1-(2-hydroxyethyl)-1H-indazol-5-yloxy)benzyl) urea hydrochloride Form B with stirring at a temperature that maintains said combination in a molten state, optionally under a stream of nitrogen, to form to provide a molten homogeneous suspension of said Form B in a carrier matrix.

79. The process of claim 78, further comprising adding an antioxidant in step (iii).

80. The process of claim 78, further comprising adding one or more release modifiers in step (iii).

81. The process according to claim 72, further comprising transferring aliquots of said liquefied or molten homogenous suspension into capsules and allowing said suspension to cool in said capsules, thereby providing a liquid, solid semi-solid or solid form of the suspension within the capsules.

82. A process for preparing 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B according to claim 1, comprising:
  (a) combining a solution of amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea in MTBE with at least 1.5 equivalents of hydrochloric acid in 1,4-dioxane for a sufficient time to convert 1-(3-tert-butyl-1-p-tolyl-1H-pyrazol-5-yl)-3-(5-fluoro-2-(1-(2-hydroxyethyl)-1H-indazol-5-yloxy)benzyl)urea to 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B;
  (b) allowing said Form B to crystallize from said solution; and
  (c) isolating said Form B.

83. A process for preparing 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B according to claim 1, comprising:
  (a) combining a solution of amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea in a solvent selected from ethyl acetate, isopropyl acetate, acetonitrile, acetone, isopropyl alcohol and ethanol with at least a stoichiometric amount of (i) HCl in 1,4-dioxane, (ii) HCl in acetone, or (iii) concentrated HCl, for a sufficient time to convert said 1-(3-tert-butyl-1-p-tolyl-1H-pyrazol-5-yl)-3-(5-fluoro-2-(1-(2-hydroxyethyl)-1H-indazol-5-yloxy)benzyl)urea to 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B;
  (b) allowing said Form B to crystallize from said solution; and
  (c) isolating said Form B.

84. A process for preparing 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B according to claim 1, comprising:
  (a) combining a solution of amorphous 1-(3-tert-butyl-1-p-tolyl-1H-pyrazol-5-yl)-3-(5-fluoro-2-(1-(2-hydroxyethyl)-1H-indazol-5-yloxy)benzyl)urea in isopropanol with at least a stoichiometric amount of an aqueous solution of hydrochloric acid for a sufficient time to convert 1-(3-tert-butyl-1-p-tolyl-1H-pyrazol-5-yl)-3-(5-fluoro-2-(1-(2-hydroxyethyl)-1H-indazol-5-yloxy)benzyl)urea to 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B;
  (b) seeding said solution from step (a) with a suspension of 1-(3-tert-butyl-1-p-tolyl-1H-pyrazol-5-yl)-3-(5-fluoro-2-(1-(2-hydroxyethyl)-1H-indazol-5-yloxy)benzyl) urea hydrochloride Form B in isopropanol to allow said 1-(3-tert-butyl-1-p-tolyl-1H-pyrazol-5-yl)-3-(5-fluoro-2-(1-(2-hydroxyethyl)-1H-indazol-5-yloxy)benzyl) urea hydrochloride Form B to crystallize from said solution; and
  (c) isolating said Form B.

85. The process according to claim 83, wherein about 1.05 equivalents of HCl are added.

86. A process for preparing 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B according to claim 1, comprising:

(a) heating a mixture of 2-(5-(2-(aminomethyl)-4-fluorophenoxy)-1H-indazol-1-yl)ethanol and phenyl 3-tert-butyl-1-p-tolyl-1H-pyrazol-5-ylcarbamate in an organic solvent at 35-40° C. for 5 hours to form 1-(3-tert-butyl-1-p-tolyl-1H-pyrazol-5-yl)-3-(5-fluoro-2-(1-(2-hydroxyethyl)-1H-indazol-5-yloxy)benzyl)urea;

(b) cooling said mixture to ambient temperature;

(c) filtering said mixture;

(d) adding at least a stoichiometric amount of aqueous HCl to said mixture;

(e) allowing said Form B to crystallize from said solution; and (f) isolating said Form B.

87. The process of claim 86, further comprising (d1) seeding said mixture in step (d) with 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form B either as a solid or as a suspension in the solvent used in step (a).

88. A crystalline polymorph of 1-(3-tert-butyl-1-p-tolyl-1H-pyrazol-5-yl)-3-(5-fluoro-2-(1-(2-hydroxyethyl)-1H-indazol-5-yloxy)benzyl)urea hydrochloride Form A.

89. The crystalline polymorph of claim 88, characterized by having at least ten specific XRPD diffraction peaks (2θ degrees±0.3) at about 6.9, 7.8, 13.9, 15.6, 16.7, 17.1, 19.2, 22.4, 22.8 and 26.6.

90. The crystalline polymorph of claim 88, characterized by substantially the same XRPD pattern as shown in FIG. 1.

91. The crystalline polymorph of claim 88, characterized by having a DSC thermogram which comprises a melt maxima temperature of about 131±5° C.

92. A method for treating a myelodysplastic syndrome comprising administering to a patient in need thereof a therapeutically effective amount of a pharmaceutical composition according to claim 43.

93. A method for treating a myelodysplastic syndrome comprising administering to a patient in need thereof a therapeutically effective amount of a pharmaceutical composition according to claim 44.

94. A method for treating a myelodysplastic syndrome comprising administering to a patient in need thereof a therapeutically effective amount of a pharmaceutical composition according to claim 45.

95. The method according to claim 94, wherein said pharmaceutical composition is formulated for oral administration.

96. The pharmaceutical composition according to claim 43 formulated for oral administration.

97. The pharmaceutical composition according to claim 44 formulated for oral administration.

98. The pharmaceutical composition according to claim 45 formulated for oral administration.

* * * * *